US009884000B2

(12) United States Patent
Boyd et al.

(10) Patent No.: US 9,884,000 B2
(45) Date of Patent: Feb. 6, 2018

(54) PERACID-GENERATING COMPOSITIONS

(71) Applicants: Colgate-Palmolive Company, New York, NY (US); E.I. DU PONT DE NEMOURS AND COMPANY, Wilmington, DE (US)

(72) Inventors: Thomas J. Boyd, Metuchen, NJ (US); Guofeng Xu, Plainsboro, NJ (US); Richard Adams, Monmouth Junction, NJ (US); Robert Pierce, Basking Ridge, NJ (US); Steven Miller, Skillman, NJ (US); David Viscio, Prescott Valley, AZ (US); Kari A. Fosser, Wilmington, DE (US); Robert Dicosimo, Chadds Ford, PA (US); Hong Wang, Kennett Square, PA (US)

(73) Assignees: Colgate-Palmolive Company, New York, NY (US); E.I. Du Pont De Nemours and Company, Wilmington, DE (US)

( * ) Notice: Subject to any disclaimer, the term of this patent is extended or adjusted under 35 U.S.C. 154(b) by 0 days.

(21) Appl. No.: 14/366,436

(22) PCT Filed: Dec. 18, 2012

(86) PCT No.: PCT/US2012/070371
§ 371 (c)(1),
(2) Date: Jun. 18, 2014

(87) PCT Pub. No.: WO2013/096321
PCT Pub. Date: Jun. 27, 2013

(65) Prior Publication Data
US 2014/0314829 A1   Oct. 23, 2014

Related U.S. Application Data

(60) Provisional application No. 61/577,499, filed on Dec. 19, 2011.

(51) Int. Cl.
| A61K 8/66 | (2006.01) |
| A61Q 11/00 | (2006.01) |
| A61K 8/37 | (2006.01) |
| A61K 8/22 | (2006.01) |

(52) U.S. Cl.
CPC .............. *A61K 8/66* (2013.01); *A61K 8/22* (2013.01); *A61K 8/37* (2013.01); *A61K 8/375* (2013.01); *A61Q 11/00* (2013.01); *A61K 2800/87* (2013.01)

(58) Field of Classification Search
None
See application file for complete search history.

(56) References Cited

U.S. PATENT DOCUMENTS

| 5,279,618 A | 1/1994 | Prota et al. |
| 5,279,816 A | 1/1994 | Church et al. |
| 5,302,375 A | 4/1994 | Viscio |
| 5,403,549 A | 4/1995 | McNeil et al. |
| 5,746,598 A | 5/1998 | Fischer |
| 5,879,691 A | 3/1999 | Sagel et al. |
| 5,891,453 A | 4/1999 | Sagel et al. |
| 5,894,017 A | 4/1999 | Sagel et al. |
| 5,989,526 A | 11/1999 | Aaslyng et al. |
| 6,136,297 A | 10/2000 | Sagel et al. |
| 6,221,341 B1 | 4/2001 | Montgomery |
| 6,274,122 B1 | 8/2001 | McLaughlin et al. |
| 6,379,653 B1 | 4/2002 | Aaslyng et al. |
| 6,419,906 B1 | 7/2002 | Xu et al. |
| 6,503,485 B1 | 1/2003 | Allred et al. |
| 6,503,486 B2 | 1/2003 | Xu et al. |
| 6,551,579 B2 | 4/2003 | Sagel et al. |
| 6,669,929 B1 | 12/2003 | Boyd et al. |
| 6,682,712 B2 | 1/2004 | Angaiah et al. |
| 6,682,721 B2 | 1/2004 | Kim et al. |
| 6,689,344 B2 | 2/2004 | Chang et al. |
| 6,705,541 B2 | 3/2004 | Schuehrer et al. |
| 6,730,316 B2 | 5/2004 | Chen |
| 6,732,887 B2 | 5/2004 | Bills et al. |
| 6,780,401 B2 | 8/2004 | Kim et al. |
| 6,949,240 B2 | 9/2005 | Sagel et al. |
| 6,956,142 B2 | 10/2005 | Bedekar et al. |
| 7,128,899 B2 | 10/2006 | Chen |
| 7,189,385 B2 | 3/2007 | Montgomery |

(Continued)

FOREIGN PATENT DOCUMENTS

| CN | 1956696 A | 5/2007 |
| CN | 101394832 A | 3/2009 |

(Continued)

OTHER PUBLICATIONS

Altschul., et al., 990, "Basic Local Alignment Search Tool," J. Mol. Biol. 215:403-410.
Binz et al., 2005, "Engineering novel binding proteins from nonimmunoglobulin domains," Nature Biotechnology 23(10):1257-1268.
Chenna et al., 2003, "Multiple sequence alignment with the Clustal series of programs," Nucleic Acids Res 31(13):3497-3500.
Coutinho et al., 1999, "Carbohydrate-active enzymes:an integrated database approach" in Recent Advances in Carbohydrate Bioengineering, Gilbert et al., eds., The Royal Society of Chemistry, Cambridge, pp. 3-12.
Dinu et. al. 2010, "Enzyme-based nanoscale composites for use as active decontamination surfaces," Adv. Funct. Materials 20:392-398.

(Continued)

*Primary Examiner* — James H Alstrum Acevedo
*Assistant Examiner* — Tara Martinez

(57) ABSTRACT

Described herein are tooth whitening strips comprising an hydratable adhesive film having a granular bleaching ingredient attached thereto, wherein upon hydration, the granular bleaching ingredient releases hydrogen peroxide which is used by an enzyme catalyst having perhydrolytic activity to enzymatically produce an effective amount of peracid bleaching agent from an acyl donor substrate. Methods of making and use the tooth whitening strips are also provided.

18 Claims, No Drawings

(56) References Cited

U.S. PATENT DOCUMENTS

| | | | |
|---|---|---|---|
| 7,243,788 B2 | 7/2007 | Schmidt et al. | |
| 7,510,859 B2 | 3/2009 | Wieland et al. | |
| 7,552,823 B2 | 6/2009 | Schuehrer et al. | |
| 7,723,083 B2 | 5/2010 | DiCosimo et al. | |
| 7,754,460 B2 | 7/2010 | Amin et al. | |
| 7,763,235 B2 | 7/2010 | Boyd et al. | |
| 7,776,010 B2 | 8/2010 | Jessop et al. | |
| 7,785,572 B2 | 8/2010 | Kim et al. | |
| 7,794,378 B2 | 9/2010 | Splane et al. | |
| 7,807,141 B2 | 10/2010 | Huang et al. | |
| 7,829,315 B2 | 11/2010 | DiCosimo et al. | |
| 7,862,801 B2 | 1/2011 | Chen | |
| 7,862,802 B2 | 1/2011 | Kim et al. | |
| 7,870,952 B2 | 1/2011 | Fontana et al. | |
| 7,909,165 B2 | 3/2011 | Perrel et al. | |
| 7,951,566 B2 | 5/2011 | DiCosimo et al. | |
| 7,964,378 B2 | 6/2011 | DiCosimo et al. | |
| 8,030,038 B2 | 10/2011 | DiCosimo et al. | |
| 8,110,536 B2 | 2/2012 | Dietshe et al. | |
| 8,206,964 B2 | 6/2012 | DiCosimo et al. | |
| 8,222,012 B2 | 7/2012 | DiCosimo et al. | |
| 8,252,562 B2 | 8/2012 | DiCosimo et al. | |
| 8,389,254 B2 | 3/2013 | DiCosimo et al. | |
| 8,663,616 B2* | 3/2014 | Butterick | A61K 8/22 424/76.1 |
| 2004/0018156 A1 | 1/2004 | Szeles et al. | |
| 2004/0112769 A1 | 6/2004 | Perry et al. | |
| 2005/0038181 A1 | 2/2005 | Chopra et al. | |
| 2005/0063923 A1 | 3/2005 | Prencipe et al. | |
| 2005/0069502 A1 | 3/2005 | Chopra et al. | |
| 2005/0249678 A1 | 11/2005 | Hassan et al. | |
| 2005/0253916 A1 | 11/2005 | Poncelet et al. | |
| 2005/0260544 A1 | 11/2005 | Jones et al. | |
| 2005/0287084 A1 | 12/2005 | Ibrahim et al. | |
| 2006/0024246 A1 | 2/2006 | Maitra et al. | |
| 2006/0292092 A1 | 12/2006 | Sharma et al. | |
| 2006/0292520 A1 | 12/2006 | Dillon et al. | |
| 2007/0105740 A1 | 5/2007 | DiCosimo et al. | |
| 2007/0178055 A1 | 8/2007 | Buch et al. | |
| 2007/0231277 A1 | 10/2007 | Sharma et al. | |
| 2007/0269388 A1 | 11/2007 | Sagel et al. | |
| 2008/0152600 A1 | 6/2008 | Huang et al. | |
| 2008/0176299 A1 | 7/2008 | DiCosimo et al. | |
| 2008/0176783 A1 | 7/2008 | DiCosimo et al. | |
| 2008/0260836 A1 | 10/2008 | Boyd et al. | |
| 2009/0005590 A1 | 1/2009 | DiCosimo et al. | |
| 2009/0311198 A1 | 12/2009 | Concar et al. | |
| 2010/0041752 A1 | 2/2010 | DiCosimo et al. | |
| 2010/0059394 A1 | 3/2010 | Fontana et al. | |
| 2010/0086534 A1 | 4/2010 | DiCosimo et al. | |
| 2010/0086535 A1 | 4/2010 | DiCosimo et al. | |
| 2010/0087529 A1 | 4/2010 | DiCosimo et al. | |
| 2010/0196287 A1 | 8/2010 | O'Connell et al. | |
| 2010/0247589 A1 | 9/2010 | Fahnestock et al. | |
| 2011/0081693 A1 | 4/2011 | DiCosimo et al. | |
| 2011/0236335 A1 | 9/2011 | DiCosimo et al. | |
| 2011/0236339 A1 | 9/2011 | Dicosimo | |
| 2012/0288548 A1 | 11/2012 | Boyd et al. | |
| 2014/0105948 A1 | 4/2014 | Gebreselassie et al. | |
| 2014/0338688 A1* | 11/2014 | Boyd | A61Q 11/00 132/200 |
| 2015/0118167 A1 | 4/2015 | Boyd et al. | |
| 2015/0265511 A1 | 9/2015 | Boyd et al. | |

FOREIGN PATENT DOCUMENTS

| | | |
|---|---|---|
| DE | 102007036392 | 2/2009 |
| RU | 2288697 C2 | 12/2006 |
| RU | 2382653 C2 | 2/2010 |
| WO | WO 1992/017158 | 10/1992 |
| WO | WO 2001/004250 | 1/2001 |
| WO | WO 2001/064175 | 9/2001 |
| WO | WO 2002/074275 | 9/2002 |
| WO | WO 2003/015656 | 2/2003 |
| WO | WO 04/024104 | 3/2004 |
| WO | WO2004024104 A2 | 3/2004 |
| WO | WO 2004/028500 | 4/2004 |
| WO | WO 2004/041102 | 5/2004 |
| WO | WO 05/056782 | 6/2005 |
| WO | WO 2005/102254 | 11/2005 |
| WO | WO2005110344 | 11/2005 |
| WO | WO2005124012 | 12/2005 |
| WO | WO2006009737 A1 | 1/2006 |
| WO | WO 06/069236 | 6/2006 |
| WO | WO 2006/111803 | 10/2006 |
| WO | WO 2007/041408 | 4/2007 |
| WO | WO2007103050 | 9/2007 |
| WO | WO 2008/140988 | 11/2008 |
| WO | WO 2010/039953 | 4/2010 |
| WO | WO 2010/039956 | 4/2010 |
| WO | WO 2011/041367 | 4/2011 |
| WO | WO 2011/090980 | 7/2011 |
| WO | WO 2011/094497 | 8/2011 |
| WO | WO2012087970 | 6/2012 |
| WO | WO 2013/039495 | 3/2013 |
| WO | WO 2013/096318 | 6/2013 |
| WO | WO 2013/096321 | 6/2013 |

OTHER PUBLICATIONS

Goujon et al., 2010. "A new bioinformatics analysis tools framework at EMBL-EBI," Nucleic Acids Research (2010) 38(Suppl):W695-699.

Higgins et al., 1989. "Fast and sensitive multiple sequence alignments on a microcomputer," Cabios Communications, 5(2):151-153.

Hosse et al., 2006, "A new generation of protein display scaffolds for molecular recognition," Protein Science 15(1):14-27.

Mitsushima et al., 1995, "Gene cloninig, nucleotide sequence, and expression of a cephalosporin-C Deacetylase from *Bacillus subtilis*," Appl. Env. Microbiol. 61(6):2224-2229.

Muyldermans, 2001, "Single domain camel antibodies: current status," Reviews in Molecular Biotechnol. 74:277-302.

Nafee, 2004, "Mucoadhesive delivery systems. I. Evaluation of mucoadhesive polymers for buccal tablet formulation," Drug development and Industrial Pharmacy, 30(9):985-993.

Needleman et al., 1970, "A general method applicable to the search for similarities in the amino acid sequence of two proteins," J. Mol. Biol. 48:443-453.

Pearson, 1994, "Searching protein sequence databases—is optimal best?" Computational Methods in Genome Research, [Proc. Int. Symp.]111-120.

Pinkernell et al., 1997, "Simultaneous HPLC Determination of peroxyacetic acid and hydrogen peroxide," Analytical Chem. 69(17):3623-3627.

Pinkernell et. al., 1997, "Sepective photometric determination of peroxycarboxylic acids in the presence of hydrogen peroxide," Analyst, 122:567-571.

Rice et al., 2000, "EMBOSS: The European molecular biology open software suite," Trends in Genetics 16(6):276-277.

Shojaei et al, 2001, "Systemic drug delivery via the buccal mucosal route," Pharmaceutical Technology, Jun. 2001 issue, pp. 70-81.

Smart, 2004, "Recent developments in the use of bioadhesive systems for delivery of drugs to the oral cavity," Critical Reviews in Therapeutic Drug Carrier Systems 21(4):319-344.

Smith-Waterman, 1981, "Identification of common molecular subsequences," J. Mol. Biol. 147:195-197.

Sudhakar et al, 2006, "Buccal bioadhesive drug delivery—A promising option for orally less efficient drugs," Journal of Controlled Release 114:15-40.

Thompson et al., 1994, "CLUSTAL W: Improving the sensitivity of progressive multiple sequence alignment through sequence weighting, position-specific gap penalties and weight matrix choice," Nucleic Acids Research, 22(22):4673-4680.

Vincent et al., 2003, "Multifunctional xylooligosaccharide/cephalosporin C deacetylase revealed by the hexameric structure of the bacillus subtilis enzyme at 1.9 Å Resolution," J. Mol. Biol. 330:593-606.

(56) References Cited

OTHER PUBLICATIONS

Written Opinion in International Application No. PCT/US2012/070371, dated Jun. 20, 2014.
International Search Report and the Written Opinion issued in International Application PCT/US2012/070371 dated Feb. 13, 2014.
Grachyova, Tekhnologiya fermentnykh preparatov, 2nd issue, revised, M.: Agropromizdat, 1987, 149.
Prokhorov Bolshaya Sovetskaya Entsiklopediya, 3rd issue, vol. 7, M.: Sov. entsiklopediya, 1972, p. 254.
Dong et al., "Cosmetics Formulation Design and Production Process 1st Edition" China Textile & Apparel Press, 79-80 (2007).
International Search Report of International Application No. PCT/US2012/070367 dated Feb. 13, 2014, 5 pages.
International Search Report of International Application No. PCT/US2011/051546 dated Jul. 16, 2012, 4 pages.
International Search Report of International Application No. PCT/US2011/65827 dated Nov. 22, 2012, 4 pages.
NCBI (National Center for Biotechnology Information. PubChem Compound Database; CID=31294,<https://pubchem.ncbi.nlm.nih.gov/compound/31294> (accessed Jun. 3, 2016)).
STN Chemical Abstracts Registry Database, 1984, CAS Registry No. 25395-31-7.
STN Chemical Abstracts Registry Database, 1984, CAS Registry No. 102-76-1.
STN Chemical Abstracts Registry Database, 1984, CAS Registry No. 623-84-7.
STN Chemical Abstracts Registry Database, 1984, CAS Registry No. 111-55-7.

\* cited by examiner

SEQUENCE LISTING

<160> NUMBER OF SEQ ID NOS: 197

<210> SEQ ID NO 1
<211> LENGTH: 325
<212> TYPE: PRT
<213> ORGANISM: Thermotoga maritima

<400> SEQUENCE: 1

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

```
Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
        130                 135                 140

Met Thr Arg Gly Ile Leu Asp Pro Arg Thr Tyr Tyr Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 2
<211> LENGTH: 375
<212> TYPE: PRT
<213> ORGANISM: artificial sequence
<220> FEATURE:
<223> OTHER INFORMATION: synthetic construct
<220> FEATURE:
<221> NAME/KEY: MISC_FEATURE
<222> LOCATION: (1)..(325)
<223> OTHER INFORMATION: Thermotoma maritima C277S variant perhydrolase
<220> FEATURE:
<221> NAME/KEY: MISC_FEATURE
<222> LOCATION: (326)..(375)
<223> OTHER INFORMATION: Oral surface targeting domain

<400> SEQUENCE: 2

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80
```

```
Glu Lys Leu Pro Cys Val Val Gln Tyr Ile Gly Tyr Asn Gly Gly Arg
             85                  90                  95

Gly Phe Pro His Asp Trp Leu Phe Trp Pro Ser Met Gly Tyr Ile Cys
        100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
        130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
        180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
        210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
        260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Gly Ala Gly Ser Pro Gly
                325                 330                 335

Ser Ala Gly Gly Pro Gly Ser Thr Lys Pro Pro Arg Thr Pro Thr Ala
        340                 345                 350

Asn Thr Ser Arg Pro His His Asn Phe Gly Ser Gly Gly Gly Ser
        355                 360                 365

Pro His His His His His His
        370                 375

<210> SEQ ID NO 3
<211> LENGTH: 960
<212> TYPE: DNA
<213> ORGANISM: Bacillus subtilis
<220> FEATURE:
<221> NAME/KEY: CDS
<222> LOCATION: (1)..(960)

<400> SEQUENCE: 3 atg caa cta ttc gat ctg ccg ctc gac caa ttg caa aca tat aag cct    48
Met Gln Leu Phe Asp Leu Pro Leu Asp Gln Leu Gln Thr Tyr Lys Pro
1               5                  10                  15 gaa aaa aca gca ccg aaa gat ttt tct gag ttt tgg aaa ttg tct ttg    96
Glu Lys Thr Ala Pro Lys Asp Phe Ser Glu Phe Trp Lys Leu Ser Leu
            20                  25                  30 gag gaa ctt gca aaa gtc caa gca gaa cct gat tta cag ccg gtt gac   144
Glu Glu Leu Ala Lys Val Gln Ala Glu Pro Asp Leu Gln Pro Val Asp
        35                  40                  45
```

```
tat cct gct gac gga gta aaa gtg tac cgt ctc aca tat aaa agc ttc      192
Tyr Pro Ala Asp Gly Val Lys Val Tyr Arg Leu Thr Tyr Lys Ser Phe
     50              55                  60 gga aac gcc cgc att acc gga tgg tac gcg gtg cct gac aag caa ggc      240
Gly Asn Ala Arg Ile Thr Gly Trp Tyr Ala Val Pro Asp Lys Gln Gly
65              70                  75                  80 ccg cat ccg gcg atc gtg aaa tat cat ggc tac aat gca agc tat gat      288
Pro His Pro Ala Ile Val Lys Tyr His Gly Tyr Asn Ala Ser Tyr Asp
                 85                  90                  95 ggt gag att cat gaa atg gta aac tgg gca ctc cat ggc tac gcc gca      336
Gly Glu Ile His Glu Met Val Asn Trp Ala Leu His Gly Tyr Ala Ala
            100                 105                 110 ttc ggc atg ctt gtc cgc ggc cag cag agc agc gag gat acg agt att      384
Phe Gly Met Leu Val Arg Gly Gln Gln Ser Ser Glu Asp Thr Ser Ile
        115                 120                 125 tca ctg cac ggt cac gct ttg ggc tgg atg acg aaa gga att ctt gat      432
Ser Leu His Gly His Ala Leu Gly Trp Met Thr Lys Gly Ile Leu Asp
130                 135                 140 aaa gat aca tac tat tac cgc ggt gtt tat ttg gac gcc gtc cgc gcg      480
Lys Asp Thr Tyr Tyr Tyr Arg Gly Val Tyr Leu Asp Ala Val Arg Ala
145                 150                 155                 160 ctt gag gtc atc agc agc ttc gac gag gtt gac gaa aca agg atc ggt      528
Leu Glu Val Ile Ser Ser Phe Asp Glu Val Asp Glu Thr Arg Ile Gly
                165                 170                 175 gtg aca gga gga agc caa ggc gga ggt tta acc att gcc gca gcg gcg      576
Val Thr Gly Gly Ser Gln Gly Gly Gly Leu Thr Ile Ala Ala Ala Ala
            180                 185                 190 ctg tca gac att cca aaa gcc gcg gtt gcc gat tat cct tat tta agc      624
Leu Ser Asp Ile Pro Lys Ala Ala Val Ala Asp Tyr Pro Tyr Leu Ser
        195                 200                 205 aac ttc gaa cgg gcc att gat gtg gcg ctt gaa cag ccg tac ctt gaa      672
Asn Phe Glu Arg Ala Ile Asp Val Ala Leu Glu Gln Pro Tyr Leu Glu
210                 215                 220 atc aat tcc ttc ttc aga aga aat ggc agc ccg gaa aca gaa gtg cag      720
Ile Asn Ser Phe Phe Arg Arg Asn Gly Ser Pro Glu Thr Glu Val Gln
225                 230                 235                 240 gcg atg aag aca ctt tca tat ttc gat att atg aat ctc gct gac cga      768
Ala Met Lys Thr Leu Ser Tyr Phe Asp Ile Met Asn Leu Ala Asp Arg
                245                 250                 255 gtg aag gtg cct gtc ctg atg tca atc ggc ctg att gac aag gtc acg      816
Val Lys Val Pro Val Leu Met Ser Ile Gly Leu Ile Asp Lys Val Thr
            260                 265                 270 ccg ccg tcc acc gtg ttt gcc gcc tac aat cat ttg gaa aca gag aaa      864
Pro Pro Ser Thr Val Phe Ala Ala Tyr Asn His Leu Glu Thr Glu Lys
        275                 280                 285 gag ctg aag gtg tac cgc tac ttc gga cat gag tat atc cct gct ttt      912
Glu Leu Lys Val Tyr Arg Tyr Phe Gly His Glu Tyr Ile Pro Ala Phe
290                 295                 300 caa acg gaa aaa ctt gct ttc ttt aag cag cat ctt aaa ggc tga taa      960
Gln Thr Glu Lys Leu Ala Phe Phe Lys Gln His Leu Lys Gly
305                 310                 315

<210> SEQ ID NO 4
<211> LENGTH: 318
<212> TYPE: PRT
<213> ORGANISM: Bacillus subtilis

<400> SEQUENCE: 4

Met Gln Leu Phe Asp Leu Pro Leu Asp Gln Leu Gln Thr Tyr Lys Pro
1               5                   10                  15
```

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
50                  55                  60

Gly Asn Ala Arg Ile Thr Gly Trp Tyr Ala Val Pro Asp Lys Gln Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
            115                 120                 125

Ser Leu His Gly His Ala Leu Gly Trp Met Thr Lys Gly Ile Leu Asp
        130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Glu Gln Pro Tyr Leu Glu
        210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
            245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
        290                 295                 300

Gln Thr Glu Lys Leu Ala Phe Phe Lys Gln His Leu Lys Gly
305                 310                 315

<210> SEQ ID NO 5
<211> LENGTH: 318
<212> TYPE: PRT
<213> ORGANISM: Bacillus subtilis

<400> SEQUENCE: 5

Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45

Tyr Pro Ala Asp Gly Val Lys Val Tyr Arg Leu Thr Tyr Lys Ser Phe
50                  55                  60

Gly Asn Ala Arg Ile Thr Gly Trp Tyr Ala Val Pro Asp Lys Glu Gly

```
                65                  70                  75                  80
        Pro His Pro Ala Ile Val Lys Tyr His Gly Tyr Asn Ala Ser Tyr Asp
                        85                  90                  95

Gly Glu Ile His Glu Met Val Asn Trp Ala Leu His Gly Tyr Ala Thr
                    100                 105                 110

Phe Gly Met Leu Val Arg Gly Gln Gln Ser Ser Glu Asp Thr Ser Ile
                115                 120                 125

Ser Pro His Gly His Ala Leu Gly Trp Met Thr Lys Gly Ile Leu Asp
            130                 135                 140

Lys Asp Thr Tyr Tyr Arg Gly Val Tyr Leu Asp Ala Val Arg Ala
        145                 150                 155                 160

Leu Glu Val Ile Ser Ser Phe Asp Glu Val Asp Thr Arg Ile Gly
                        165                 170                 175

Val Thr Gly Gly Ser Gln Gly Gly Leu Thr Ile Ala Ala Ala
                    180                 185                 190

Leu Ser Asp Ile Pro Lys Ala Ala Val Ala Asp Tyr Pro Tyr Leu Ser
                195                 200                 205

Asn Phe Glu Arg Ala Ile Asp Val Ala Leu Glu Gln Pro Tyr Leu Glu
            210                 215                 220

Ile Asn Ser Phe Phe Arg Arg Asn Gly Ser Pro Glu Thr Glu Val Gln
        225                 230                 235                 240

Ala Met Lys Thr Leu Ser Tyr Phe Asp Ile Met Asn Leu Ala Asp Arg
                        245                 250                 255

Val Lys Val Pro Val Leu Met Ser Ile Gly Leu Ile Asp Lys Val Thr
                    260                 265                 270

Pro Pro Ser Thr Val Phe Ala Ala Tyr Asn His Leu Glu Thr Lys Lys
                275                 280                 285

Glu Leu Lys Val Tyr Arg Tyr Phe Gly His Glu Tyr Ile Pro Ala Phe
            290                 295                 300

Gln Thr Glu Lys Leu Ala Phe Phe Lys Gln His Leu Lys Gly
        305                 310                 315

<210> SEQ ID NO 6
<211> LENGTH: 318
<212> TYPE: PRT
<213> ORGANISM: Bacillus subtilis

<400> SEQUENCE: 6

Met Gln Leu Phe Asp Leu Pro Leu Asp Gln Leu Gln Thr Tyr Lys Pro
1               5                   10                  15

Glu Lys Thr Thr Pro Asn Asp Phe Ser Glu Phe Trp Lys Ser Ser Leu
                20                  25                  30

Asp Glu Leu Ala Lys Val Lys Ala Ala Pro Asp Leu Gln Leu Val Asp
            35                  40                  45

Tyr Pro Ala Asp Gly Val Lys Val Tyr Arg Leu Thr Tyr Lys Ser Phe
        50                  55                  60

Gly Asn Ala Arg Ile Thr Gly Trp Tyr Ala Val Pro Asp Lys Glu Gly
65                  70                  75                  80

Pro His Pro Ala Ile Val Lys Tyr His Gly Tyr Asn Ala Ser Tyr Asp
                85                  90                  95

Gly Glu Ile His Glu Met Val Asn Trp Ala Leu His Gly Tyr Ala Ala
            100                 105                 110

Phe Gly Met Leu Val Arg Gly Gln Gln Ser Ser Glu Asp Thr Ser Ile
        115                 120                 125
```

```
Ser Pro His Gly His Ala Leu Gly Trp Met Thr Lys Gly Ile Leu Asp
    130                 135                 140

Lys Asp Thr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Leu Thr Ile Ala Ala Ala Ala
            180                 185                 190

Leu Ser Asp Ile Pro Lys Ala Ala Val Ala Asp Tyr Pro Tyr Leu Ser
        195                 200                 205

Asn Phe Glu Arg Ala Ile Asp Val Ala Leu Gln Pro Tyr Leu Glu
    210                 215                 220

Ile Asn Ser Phe Phe Arg Arg Asn Gly Ser Pro Glu Thr Glu Glu Lys
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
            260                 265                 270

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 7
<211> LENGTH: 318
<212> TYPE: PRT
<213> ORGANISM: Bacillus licheniformis

<400> SEQUENCE: 7

Met Gln Gln Pro Tyr Asp Met Pro Leu Glu Gln Leu Tyr Gln Tyr Lys
1               5                   10                  15

Pro Glu Arg Thr Ala Pro Ala Asp Phe Lys Glu Phe Trp Lys Gly Ser
            20                  25                  30

Leu Glu Glu Leu Ala Asn Glu Lys Ala Gly Pro Gln Leu Glu Pro His
        35                  40                  45

Glu Tyr Pro Ala Asp Gly Val Lys Val Tyr Trp Leu Thr Tyr Arg Ser
    50                  55                  60

Ile Gly Gly Ala Arg Ile Lys Gly Trp Tyr Ala Val Pro Asp Arg Gln
65                  70                  75                  80

Gly Pro His Pro Ala Ile Val Lys Tyr His Gly Tyr Asn Ala Ser Tyr
                85                  90                  95

Asp Gly Asp Ile His Asp Ile Val Asn Trp Ala Leu His Gly Tyr Ala
            100                 105                 110

Ala Phe Gly Met Leu Val Arg Gly Gln Asn Ser Ser Glu Asp Thr Glu
        115                 120                 125

Ile Ser His His Gly His Val Pro Gly Trp Met Thr Lys Gly Ile Leu
    130                 135                 140

Asp Pro Lys Thr Tyr Tyr Tyr Arg Gly Val Tyr Leu Asp Ala Val Arg
145                 150                 155                 160

Ala Val Glu Val Val Ser Gly Phe Ala Glu Val Asp Glu Lys Arg Ile
                165                 170                 175

Gly Val Ile Gly Ala Ser Gln Gly Gly Gly Leu Ala Val Ala Val Ser
            180                 185                 190
```

Ala Leu Ser Asp Ile Pro Lys Ala Val Ser Glu Tyr Pro Tyr Leu
            195                 200                 205

Ser Asn Phe Gln Arg Ala Ile Asp Thr Ala Ile Asp Gln Pro Tyr Leu
210                 215                 220

Glu Ile Asn Ser Phe Phe Arg Arg Asn Thr Ser Pro Asp Ile Glu Gln
225                 230                 235                 240

Ala Ala Met His Thr Leu Ser Tyr Phe Asp Val Met Asn Leu Ala Gln
                245                 250                 255

Leu Val Lys Ala Thr Val Leu Met Ser Ile Gly Leu Val Asp Thr Ile
                260                 265                 270

Thr Pro Pro Ser Thr Val Phe Ala Ala Tyr Asn His Leu Glu Thr Asp
                275                 280                 285

Lys Glu Ile Lys Val Tyr Arg Tyr Phe Gly His Glu Tyr Ile Pro Pro
                290                 295                 300

Phe Gln Thr Glu Lys Leu Ala Phe Leu Arg Lys His Leu Lys
305                 310                 315

<210> SEQ ID NO 8
<211> LENGTH: 320
<212> TYPE: PRT
<213> ORGANISM: Bacillus pumilus

<400> SEQUENCE: 8

Met Gln Leu Phe Asp Leu Ser Leu Glu Glu Leu Lys Lys Tyr Lys Pro
1               5                   10                  15

Lys Lys Thr Ala Arg Pro Asp Phe Ser Asp Phe Trp Lys Lys Ser Leu
                20                  25                  30

Glu Glu Leu Arg Gln Val Glu Ala Glu Pro Thr Leu Glu Ser Tyr Asp
            35                  40                  45

Tyr Pro Val Lys Gly Val Lys Val Tyr Arg Leu Thr Tyr Gln Ser Phe
        50                  55                  60

Gly His Ser Lys Ile Glu Gly Phe Tyr Ala Val Pro Asp Gln Thr Gly
65                  70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
                100                 105                 110

Phe Gly Met Leu Val Arg Gly Gln Gly Gly Ser Glu Asp Thr Ser Val
            115                 120                 125

Thr Pro Gly Gly His Ala Leu Gly Trp Met Thr Lys Gly Ile Leu Ser
        130                 135                 140

Lys Asp Thr Tyr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
                165                 170                 175

Val Ile Gly Gly Ser Gln Gly Gly Ala Leu Ala Ile Ala Ala Ala Ala
                180                 185                 190

Leu Ser Asp Ile Pro Lys Val Val Ala Asp Tyr Pro Tyr Leu Ser
            195                 200                 205

Asn Phe Glu Arg Ala Val Asp Val Ala Leu Glu Gln Pro Tyr Leu Glu
        210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp

```
                     245                 250                 255
Val Lys Gln Pro Thr Leu Met Ala Ile Gly Leu Ile Asp Lys Ile Thr
                 260                 265                 270

Pro Pro Ser Thr Val Phe Ala Ala Tyr Asn His Leu Glu Thr Asp Lys
             275                 280                 285

Asp Leu Lys Val Tyr Arg Tyr Phe Gly His Glu Phe Ile Pro Ala Phe
         290                 295                 300

Gln Thr Glu Lys Leu Ser Phe Leu Gln Lys His Leu Leu Leu Ser Thr
305                 310                 315                 320

<210> SEQ ID NO 9
<211> LENGTH: 320
<212> TYPE: PRT
<213> ORGANISM: Clostridium thermocellum

<400> SEQUENCE: 9

Met Ala Gln Leu Tyr Asp Met Pro Leu Glu Glu Leu Lys Lys Tyr Lys
1               5                   10                  15

Pro Ala Leu Thr Lys Gln Lys Asp Phe Asp Glu Phe Trp Glu Lys Ser
            20                  25                  30

Leu Lys Glu Leu Ala Glu Ile Pro Leu Lys Tyr Gln Leu Ile Pro Tyr
        35                  40                  45

Asp Phe Pro Ala Arg Arg Val Lys Val Phe Arg Val Glu Tyr Leu Gly
    50                  55                  60

Phe Lys Gly Ala Asn Ile Glu Gly Trp Leu Ala Val Pro Glu Gly Glu
65                  70                  75                  80

Gly Leu Tyr Pro Gly Leu Val Gln Phe His Gly Tyr Asn Trp Ala Met
                85                  90                  95

Asp Gly Cys Val Pro Asp Val Val Asn Trp Ala Leu Asn Gly Tyr Ala
            100                 105                 110

Ala Phe Leu Met Leu Val Arg Gly Gln Gln Gly Arg Ser Val Asp Asn
        115                 120                 125

Ile Val Pro Gly Ser Gly His Ala Leu Gly Trp Met Ser Lys Gly Ile
    130                 135                 140

Leu Ser Pro Glu Glu Tyr Tyr Tyr Arg Gly Val Tyr Met Asp Ala Val
145                 150                 155                 160

Arg Ala Val Glu Ile Leu Ala Ser Leu Pro Cys Val Asp Glu Ser Arg
                165                 170                 175

Ile Gly Val Thr Gly Gly Ser Gln Gly Gly Leu Ala Leu Ala Val
            180                 185                 190

Ala Ala Leu Ser Gly Ile Pro Lys Val Ala Ala Val His Tyr Pro Phe
        195                 200                 205

Leu Ala His Phe Glu Arg Ala Ile Asp Val Ala Pro Asp Gly Pro Tyr
    210                 215                 220

Leu Glu Ile Asn Glu Tyr Leu Arg Arg Asn Ser Gly Glu Glu Ile Glu
225                 230                 235                 240

Arg Gln Val Lys Lys Thr Leu Ser Tyr Phe Asp Ile Met Asn Leu Ala
                245                 250                 255

Pro Arg Ile Lys Cys Arg Thr Trp Ile Cys Thr Gly Leu Val Asp Glu
            260                 265                 270

Ile Thr Pro Pro Ser Thr Val Phe Ala Val Tyr Asn His Leu Lys Cys
        275                 280                 285

Pro Lys Glu Ile Ser Val Phe Arg Tyr Phe Gly His Glu His Met Pro
    290                 295                 300
```

```
Gly Ser Val Glu Ile Lys Leu Arg Ile Leu Met Asp Glu Leu Asn Pro
305                 310                 315                 320

<210> SEQ ID NO 10
<211> LENGTH: 325
<212> TYPE: PRT
<213> ORGANISM: Thermotoga neapolitana

<400> SEQUENCE: 10

Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Val Ala Gly Gly Ser Gln Gly Gly Gly
            180                 185                 190

Ile Ala Leu Ala Val Ser Ala Leu Ser Asn Arg Val Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Glu Gly
                325

<210> SEQ ID NO 11
<211> LENGTH: 325
<212> TYPE: PRT
<213> ORGANISM: Thermotoga maritima
```

<400> SEQUENCE: 11

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Cys Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
            325

<210> SEQ ID NO 12
<211> LENGTH: 320
<212> TYPE: PRT
<213> ORGANISM: Thermoanaerobacterium sp.

<400> SEQUENCE: 12

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asn Arg Ala Leu
            20                  25                  30

-continued

```
Asp Glu Met Arg Ser Val Asp Pro Lys Ile Glu Leu Lys Glu Ser Ser
             35                  40                  45
Phe Gln Val Ser Phe Ala Glu Cys Tyr Asp Leu Tyr Phe Thr Gly Val
         50                  55                  60
Arg Gly Ala Arg Ile His Ala Lys Tyr Ile Lys Pro Lys Thr Glu Gly
 65                  70                  75                  80
Lys His Pro Ala Leu Ile Arg Phe His Gly Tyr Ser Ser Asn Ser Gly
                 85                  90                  95
Asp Trp Asn Asp Lys Leu Asn Tyr Val Ala Ala Gly Phe Thr Val Val
            100                 105                 110
Ala Met Asp Val Arg Gly Gln Gly Gln Ser Gln Asp Val Gly Gly
            115                 120                 125
Val Thr Gly Asn Thr Leu Asn Gly His Ile Ile Arg Gly Leu Asp Asp
        130                 135                 140
Asp Ala Asp Asn Met Leu Phe Arg His Ile Phe Leu Asp Thr Ala Gln
145                 150                 155                 160
Leu Ala Gly Ile Val Met Asn Met Pro Glu Val Asp Glu Asp Arg Val
                165                 170                 175
Gly Val Met Gly Pro Ser Gln Gly Gly Leu Ser Leu Ala Cys Ala
            180                 185                 190
Ala Leu Glu Pro Arg Val Arg Lys Val Val Ser Glu Tyr Pro Phe Leu
        195                 200                 205
Ser Asp Tyr Lys Arg Val Trp Asp Leu Asp Leu Ala Lys Asn Ala Tyr
    210                 215                 220
Gln Glu Ile Thr Asp Tyr Phe Arg Leu Phe Asp Pro Arg His Glu Arg
225                 230                 235                 240
Glu Asn Glu Val Phe Thr Lys Leu Gly Tyr Ile Asp Val Lys Asn Leu
                245                 250                 255
Ala Lys Arg Ile Lys Gly Asp Val Leu Met Cys Val Gly Leu Met Asp
            260                 265                 270
Gln Val Cys Pro Pro Ser Thr Val Phe Ala Ala Tyr Asn Asn Ile Gln
        275                 280                 285
Ser Lys Lys Asp Ile Lys Val Tyr Pro Asp Tyr Gly His Glu Pro Met
    290                 295                 300
Arg Gly Phe Gly Asp Leu Ala Met Gln Phe Met Leu Glu Leu Tyr Ser
305                 310                 315                 320

<210> SEQ ID NO 13
<211> LENGTH: 319
<212> TYPE: PRT
<213> ORGANISM: Bacillus halodurans

<400> SEQUENCE: 13

Met Pro Leu Ile Asp Met Pro Leu Thr Glu Leu Lys Glu Tyr Met Gly
 1               5                  10                  15
Arg Asn Pro Lys Pro Asp Asp Phe Thr Glu Tyr Trp Arg Ala Leu
             20                  25                  30
Gln Glu Met Arg Lys Val Asn Pro Asn Val Glu Leu Ile Pro Ser Asp
             35                  40                  45
Phe Gln Thr Thr Tyr Ala Glu Cys Phe His Leu Tyr Phe Thr Gly Val
         50                  55                  60
Arg Gly Ala Arg Ile His Ala Lys Tyr Val Arg Pro Arg His Thr Ser
 65                  70                  75                  80
Gly Thr His Pro Ala Val Ile His Phe His Gly Tyr Thr Met Asn Ala
```

```
                    85                  90                  95
Gly Glu Trp Thr Gly Leu Leu His Tyr Ala Ala Leu Gly Tyr Ser Val
            100                 105                 110

Leu Ala Met Asp Val Arg Gly Gln Gly Gly Leu Ser Glu Asp Thr Gly
            115                 120                 125

Gly Val Lys Gly Asn Thr His Ser Gly His Ile Ile Arg Gly Leu Asp
            130                 135                 140

Asp Asn Ala Asp Gln Leu Leu Phe Arg His Val Phe Leu Asp Thr Ala
145                 150                 155                 160

Gln Leu Ala Asn Ile Val Met Asn Leu Pro Glu Val Asp Glu Glu Arg
                165                 170                 175

Val Ala Val Thr Gly Trp Ser Gln Gly Gly Ala Leu Ala Ile Ala Cys
            180                 185                 190

Ala Ala Leu Glu Pro Lys Ile Lys Lys Val Ala Pro Val Tyr Pro Phe
            195                 200                 205

Leu Ser Asp Tyr Gln Arg Val Trp Glu Met Asp Leu Ala Glu Lys Ala
            210                 215                 220

Tyr Asp Glu Leu Gln Thr Tyr Phe Arg Arg Phe Asp Pro Gln His Arg
225                 230                 235                 240

Arg Glu Ala Glu Ile Phe Thr Lys Leu Gly Tyr Ile Asp Ile Gln His
                245                 250                 255

Leu Ala Pro Leu Val Lys Gly Glu Val Leu Ala Val Gly Leu Met
            260                 265                 270

Asp Thr Val Cys Pro Pro Ser Thr Gln Phe Ala Met Tyr Asn Lys Leu
            275                 280                 285

Thr Thr Thr Lys Ser Ile Glu Leu Tyr Pro Asp Phe Ala His Glu Asp
            290                 295                 300

Leu Pro Gly His Arg Asp Arg Ile Phe Gln Phe Leu Ser Asp Leu
305                 310                 315

<210> SEQ ID NO 14
<211> LENGTH: 317
<212> TYPE: PRT
<213> ORGANISM: Bacillus clausii

<400> SEQUENCE: 14

Met Pro Leu Val Asp Met Pro Leu Arg Glu Leu Leu Ala Tyr Glu Gly
1               5                   10                  15

Ile Asn Pro Lys Pro Ala Asp Phe Asp Gln Tyr Trp Asn Arg Ala Lys
                20                  25                  30

Thr Glu Ile Glu Ala Ile Asp Pro Glu Val Thr Leu Val Glu Ser Ser
            35                  40                  45

Phe Gln Cys Ser Phe Ala Asn Cys Tyr His Phe Tyr Tyr Arg Ser Ala
            50                  55                  60

Gly Asn Ala Lys Ile His Ala Lys Tyr Val Gln Pro Lys Ala Gly Glu
65                  70                  75                  80

Lys Thr Pro Ala Val Phe Met Phe His Gly Tyr Gly Gly Arg Ser Ala
                85                  90                  95

Glu Trp Ser Ser Leu Leu Asn Tyr Val Ala Ala Gly Phe Ser Val Phe
            100                 105                 110

Tyr Met Asp Val Arg Gly Gln Gly Gly Thr Ser Glu Asp Pro Gly Gly
            115                 120                 125

Val Arg Gly Asn Thr Tyr Arg Gly His Ile Ile Arg Gly Leu Asp Ala
            130                 135                 140
```

```
Gly Pro Asp Ala Leu Phe Tyr Arg Ser Val Phe Leu Asp Thr Val Gln
145                 150                 155                 160

Leu Val Arg Ala Ala Lys Thr Leu Pro His Ile Asp Lys Thr Arg Leu
                165                 170                 175

Met Ala Thr Gly Trp Ser Gln Gly Gly Ala Leu Thr Leu Ala Cys Ala
            180                 185                 190

Ala Leu Val Pro Glu Ile Lys Arg Leu Ala Pro Val Tyr Pro Phe Leu
        195                 200                 205

Ser Asp Tyr Lys Arg Val Trp Gln Met Asp Leu Ala Val Arg Ser Tyr
    210                 215                 220

Lys Glu Leu Ala Asp Tyr Phe Arg Ser Tyr Asp Pro Gln His Lys Arg
225                 230                 235                 240

His Gly Glu Ile Phe Glu Arg Leu Gly Tyr Ile Asp Val Gln His Leu
                245                 250                 255

Ala Asp Arg Ile Gln Gly Asp Val Leu Met Gly Val Gly Leu Met Asp
            260                 265                 270

Thr Glu Cys Pro Pro Ser Thr Gln Phe Ala Ala Tyr Asn Lys Ile Lys
        275                 280                 285

Ala Lys Lys Ser Tyr Glu Leu Tyr Pro Asp Phe Gly His Glu His Leu
    290                 295                 300

Pro Gly Met Asn Asp His Ile Phe Arg Phe Thr Ser
305                 310                 315

<210> SEQ ID NO 15
<211> LENGTH: 325
<212> TYPE: PRT
<213> ORGANISM: Thermotoga neapolitana
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 15

Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Val Ala Gly Gly Ser Gln Gly Gly Gly
```

```
                180                 185                 190
Ile Ala Leu Ala Val Ser Ala Leu Ser Asn Arg Val Lys Ala Leu Leu
            195                 200                 205

Cys Asp Val Pro Phe Leu Cys His Phe Arg Arg Ala Val Gln Leu Val
210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Ala Arg Ala Lys Val Pro Ala Leu Phe Ser Val Gly Leu
        260                 265                 270

Met Asp Thr Ile Xaa Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
        290                 295                 300

Gly Gly Gly Ser Phe Gln Ala Ile Glu Gln Val Lys Phe Leu Lys Arg
305                 310                 315                 320

Leu Phe Glu Glu Gly
            325

<210> SEQ ID NO 16
<211> LENGTH: 325
<212> TYPE: PRT
<213> ORGANISM: Thermotoga maritima
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 16

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
            195                 200                 205
```

```
Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly
                325

<210> SEQ ID NO 17
<211> LENGTH: 326
<212> TYPE: PRT
<213> ORGANISM: Thermotoga lettingae
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 17

Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Ser Phe Arg Asn
65                  70                  75                  80

Gly Lys Leu Pro Cys Val Val Glu Phe Val Gly Tyr Gly Gly Arg
                85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
        115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
        195                 200                 205

Cys Asp Val Pro Phe Leu Cys His Tyr Lys Arg Ala Val Gln Ile Thr
    210                 215                 220
```

```
Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
            245                 250                 255

Asn Phe Ala Ala Arg Ala Lys Cys Pro Ala Leu Phe Ser Val Gly Leu
        260                 265                 270

Met Asp Asp Ile Xaa Pro Pro Ser Thr Val Phe Ala Ala Tyr Asn Tyr
            275                 280                 285

Tyr Ala Gly Glu Lys Asp Ile Arg Ile Tyr Pro Tyr Asn Asn His Glu
        290                 295                 300

Gly Gly Gly Ser Phe His Thr Leu Glu Lys Leu Lys Phe Val Lys Lys
305                 310                 315                 320

Thr Ile Ser Met Arg Glu
                325

<210> SEQ ID NO 18
<211> LENGTH: 325
<212> TYPE: PRT
<213> ORGANISM: Thermotoga petrophilia
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 18

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
```

```
                        245                 250                 255
Asn Phe Ala Val Arg Ala Lys Ile Pro Ala Leu Phe Ser Val Gly Leu
                260                 265                 270

Met Asp Asn Ile Xaa Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
        290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 19
<211> LENGTH: 325
<212> TYPE: PRT
<213> ORGANISM: Thermotoga sp. RQ2a
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 19

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270
```

```
Met Asp Asn Ile Xaa Pro Pro Ser Thr Val Phe Ala Ala Tyr Asn His
        275             280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305             310                 315                 320

Leu Phe Glu Lys Gly
            325

<210> SEQ ID NO 20
<211> LENGTH: 329
<212> TYPE: PRT
<213> ORGANISM: Thermotoga sp. RQ2b
<220> FEATURE:
<221> NAME/KEY: MISC_FEATURE
<222> LOCATION: (278)..(278)
<223> OTHER INFORMATION: Xaa is Ala, Val, Ser, or Thr.

<400> SEQUENCE: 20

Met Ala Leu Phe Asp Met Pro Leu Glu Lys Leu Arg Ser Tyr Leu Pro
1               5                   10                  15

Asp Arg Tyr Glu Glu Asp Phe Asp Leu Phe Trp Lys Glu Thr Leu
        20                  25                  30

Glu Glu Ser Arg Lys Phe Pro Leu Asp Pro Ile Phe Glu Arg Val Asp
        35                  40                  45

Tyr Leu Leu Glu Asn Val Glu Val Tyr Asp Val Thr Phe Ser Gly Tyr
    50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95

Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
        115                 120                 125

Asp Thr Pro Asp Tyr Cys Asp Glu Pro Ile Asn Pro Gln Phe Pro Gly
    130                 135                 140

Phe Met Thr Arg Gly Ile Leu Asp Pro Arg Thr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
        195                 200                 205

Val Ser Asn Val Pro Phe Leu Cys His Phe Arg Arg Ala Val Gln Ile
    210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Xaa Pro Pro Ser Thr Val Phe Ala Ala Tyr Asn
        275                 280                 285
```

His Tyr Ala Gly Pro Lys Glu Ile Lys Val Tyr Pro Phe Asn Glu His
    290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
                325

<210> SEQ ID NO 21
<211> LENGTH: 326
<212> TYPE: PRT
<213> ORGANISM: Thermotoga lettingae

<400> SEQUENCE: 21

Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
                20                  25                  30

His Glu Thr Arg Gly Tyr Phe Gln Glu Pro Ile Leu Lys Lys Val Asp
            35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Arg
                85                  90                  95

Gly Phe Pro Tyr Asp Trp Leu Leu Trp Ser Ala Ala Gly Tyr Ala His
                100                 105                 110

Phe Ile Met Asp Thr Arg Gly Gln Gly Ser Asn Trp Met Lys Gly Asp
            115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
    195                 200                 205

Cys Asp Val Pro Phe Leu Cys His Tyr Lys Arg Ala Val Gln Ile Thr
210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                245                 250                 255

Asn Phe Ala Ala Arg Ala Lys Cys Pro Ala Leu Phe Ser Val Gly Leu
            260                 265                 270

Met Asp Asp Ile Cys Pro Pro Ser Thr Val Phe Ala Ala Tyr Asn Tyr
    275                 280                 285

Tyr Ala Gly Glu Lys Asp Ile Arg Ile Tyr Pro Tyr Asn Asn His Glu
290                 295                 300

Gly Gly Gly Ser Phe His Thr Leu Glu Lys Leu Lys Phe Val Lys Lys
305                 310                 315                 320

Thr Ile Ser Met Arg Glu
                325

<210> SEQ ID NO 22
<211> LENGTH: 325
<212> TYPE: PRT
<213> ORGANISM: Thermotoga petrophilia

<400> SEQUENCE: 22

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu
            20                  25                  30

Ala Glu Asn Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Ser Gln Gly Gly Gly
            180                 185                 190

Ile Ala Leu Ala Val Ser Ala Leu Ser Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Lys Gly
                325
```

<210> SEQ ID NO 23
<211> LENGTH: 325
<212> TYPE: PRT
<213> ORGANISM: Thermotoga sp. RQ2

<400> SEQUENCE: 23

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Val Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Lys Gly
            325

<210> SEQ ID NO 24
<211> LENGTH: 329
<212> TYPE: PRT
<213> ORGANISM: Thermotoga sp. RQ2

<400> SEQUENCE: 24

Met Ala Leu Phe Asp Met Pro Leu Glu Lys Leu Arg Ser Tyr Leu Pro
1               5                   10                  15

Asp Arg Tyr Glu Glu Glu Asp Phe Asp Leu Phe Trp Lys Glu Thr Leu
            20                  25                  30

Glu Glu Ser Arg Lys Phe Pro Leu Asp Pro Ile Phe Glu Arg Val Asp

Tyr Leu Leu Glu Asn Val Glu Val Tyr Asp Val Thr Phe Ser Gly Tyr
            50                  55                  60

Arg Gly Gln Arg Ile Lys Ala Trp Leu Ile Leu Pro Val Val Lys Lys
 65                  70                  75                  80

Glu Glu Arg Leu Pro Cys Ile Val Glu Ile Gly Tyr Arg Gly Gly
                    85                  90                  95

Arg Gly Phe Pro Phe Asp Trp Leu Phe Trp Ser Ser Ala Gly Tyr Ala
                    100                 105                 110

His Phe Val Met Asp Thr Arg Gly Gln Gly Thr Ser Arg Val Lys Gly
                115                 120                 125

Asp Thr Pro Asp Tyr Cys Asp Glu Pro Ile Asn Pro Gln Phe Pro Gly
                130                 135                 140

Phe Met Thr Arg Gly Ile Leu Asp Pro Arg Thr Tyr Tyr Arg Arg
145                 150                 155                 160

Val Phe Thr Asp Ala Val Arg Ala Val Glu Thr Ala Ser Ser Phe Pro
                    165                 170                 175

Gly Ile Asp Pro Glu Arg Ile Ala Val Val Gly Thr Ser Gln Gly Gly
                180                 185                 190

Gly Ile Ala Leu Ala Val Ala Ala Leu Ser Glu Ile Pro Lys Ala Leu
                195                 200                 205

Val Ser Asn Val Pro Phe Leu Cys His Phe Arg Arg Ala Val Gln Ile
                210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
                260                 265                 270

Leu Met Asp Lys Thr Cys Pro Pro Ser Thr Val Phe Ala Ala Tyr Asn
                275                 280                 285

His Tyr Ala Gly Pro Lys Glu Ile Lys Val Tyr Pro Phe Asn Glu His
                290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
                325

<210> SEQ ID NO 25
<211> LENGTH: 320
<212> TYPE: PRT
<213> ORGANISM: Thermoanaerobacterium saccharolyticum

<400> SEQUENCE: 25

Met Gly Leu Phe Asp Met Pro Leu Gln Lys Leu Arg Glu Tyr Thr Gly
 1                   5                  10                  15

Thr Asn Pro Cys Pro Glu Asp Phe Asp Glu Tyr Trp Asp Arg Ala Leu
                    20                  25                  30

Asp Glu Met Arg Ser Val Asp Pro Lys Ile Lys Met Lys Lys Ser Ser
                35                  40                  45

Phe Gln Val Pro Phe Ala Glu Cys Tyr Asp Leu Tyr Phe Thr Gly Val
            50                  55                  60

Arg Gly Ala Arg Ile His Ala Lys Tyr Ile Arg Pro Lys Thr Glu Gly
 65                  70                  75                  80

```
Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110

Ala Met Asp Ala Arg Gly Gln Gly Gly Gln Ser Gln Asp Val Gly Gly
        115                 120                 125

Val Asn Gly Asn Thr Leu Asn Gly His Ile Ile Arg Gly Leu Asp Asp
    130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Ile Asp Glu Asp Arg Val
                165                 170                 175

Ala Val Met Gly Pro Ser Gln Gly Gly Leu Ser Leu Ala Cys Ala
            180                 185                 190

Ala Leu Glu Pro Lys Ile Arg Lys Val Val Ser Glu Tyr Pro Phe Leu
        195                 200                 205

Ser Asp Tyr Lys Arg Val Trp Asp Leu Asp Leu Ala Lys Asn Ala Tyr
    210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
            260                 265                 270

Gln Val Cys Pro Pro Ser Thr Val Phe Ala Ala Tyr Asn Asn Ile Gln
        275                 280                 285

Ser Lys Lys Asp Ile Lys Val Tyr Pro Asp Tyr Gly His Glu Pro Met
    290                 295                 300

Arg Gly Phe Gly Asp Leu Ala Met Gln Phe Met Leu Glu Leu Tyr Ser
305                 310                 315                 320

<210> SEQ ID NO 26
<211> LENGTH: 312
<212> TYPE: PRT
<213> ORGANISM: Lactococcus lactis

<400> SEQUENCE: 26

Met Thr Lys Ile Asn Asn Trp Gln Asp Tyr Gln Gly Ser Ser Leu Lys
1               5                   10                  15

Pro Glu Asp Phe Asp Lys Phe Trp Asp Glu Lys Ile Asn Leu Val Ser
            20                  25                  30

Asn His Gln Phe Glu Phe Glu Leu Ile Glu Lys Asn Leu Ser Ser Lys
        35                  40                  45

Val Val Asn Phe Tyr His Leu Trp Phe Thr Ala Ile Asp Gly Ala Lys
    50                  55                  60

Ile His Ala Gln Leu Ile Val Pro Lys Asn Leu Lys Glu Lys Tyr Pro
65                  70                  75                  80

Ala Ile Leu Gln Phe His Gly Tyr His Cys Asp Ser Gly Asp Trp Val
                85                  90                  95

Asp Lys Ile Gly Ile Val Ala Glu Gly Asn Val Val Leu Ala Leu Asp
            100                 105                 110

Cys Arg Gly Gln Gly Gly Leu Ser Gln Asp Asn Ile Gln Thr Met Gly
        115                 120                 125

Met Thr Met Lys Gly Leu Ile Val Arg Gly Ile Asp Glu Gly Tyr Glu
    130                 135                 140
```

-continued

```
Asn Leu Tyr Tyr Val Arg Gln Phe Met Asp Leu Ile Thr Ala Thr Lys
145                 150                 155                 160

Ile Leu Ser Glu Phe Asp Phe Val Asp Glu Thr Asn Ile Ser Ala Gln
                165                 170                 175

Gly Ala Ser Gln Gly Gly Ala Leu Ala Val Ala Cys Ala Ala Leu Ser
            180                 185                 190

Pro Leu Ile Lys Lys Val Thr Ala Thr Tyr Pro Phe Leu Ser Asp Tyr
                195                 200                 205

Arg Lys Ala Tyr Glu Leu Gly Ala Glu Ser Ala Phe Glu Glu Leu
            210                 215                 220

Pro Tyr Trp Phe Gln Phe Lys Asp Pro Leu His Leu Arg Glu Asp Trp
225                 230                 235                 240

Phe Phe Asn Gln Leu Glu Tyr Ile Asp Ile Gln Asn Leu Ala Pro Arg
                245                 250                 255

Ile Lys Ala Glu Val Ile Trp Ile Leu Gly Gly Lys Asp Thr Val Val
            260                 265                 270

Pro Pro Ile Thr Gln Met Ala Ala Tyr Asn Lys Ile Gln Ser Lys Lys
                275                 280                 285

Ser Leu Tyr Val Leu Pro Glu Tyr Gly His Glu Tyr Leu Pro Lys Ile
            290                 295                 300

Ser Asp Trp Leu Arg Glu Asn Gln
305                 310

<210> SEQ ID NO 27
<211> LENGTH: 323
<212> TYPE: PRT
<213> ORGANISM: Mesorhizobium loit

<400> SEQUENCE: 27

Met Pro Phe Pro Asp Leu Ile Gln Pro Glu Leu Gly Ala Tyr Val Ser
1               5                   10                  15

Ser Val Gly Met Pro Asp Asp Phe Ala Gln Phe Trp Thr Ser Thr Ile
            20                  25                  30

Ala Glu Ala Arg Gln Ala Gly Gly Glu Val Ser Ile Val Gln Ala Gln
        35                  40                  45

Thr Thr Leu Lys Ala Val Gln Ser Phe Asp Val Thr Phe Pro Gly Tyr
    50                  55                  60

Gly Gly His Pro Ile Lys Gly Trp Leu Ile Leu Pro Thr His His Lys
65                  70                  75                  80

Gly Arg Leu Pro Leu Val Val Gln Tyr Ile Gly Tyr Gly Gly Arg
                85                  90                  95

Gly Leu Ala His Glu Gln Leu His Trp Ala Ala Ser Gly Phe Ala Tyr
            100                 105                 110

Phe Arg Met Asp Thr Arg Gly Gln Gly Ser Asp Trp Ser Val Gly Glu
        115                 120                 125

Thr Ala Asp Pro Val Gly Ser Thr Ser Ser Ile Pro Gly Phe Met Thr
    130                 135                 140

Arg Gly Val Leu Asp Lys Asn Asp Tyr Tyr Arg Arg Leu Phe Thr
145                 150                 155                 160

Asp Ala Val Arg Ala Ile Asp Ala Leu Leu Gly Leu Asp Phe Val Asp
                165                 170                 175

Pro Glu Arg Ile Ala Val Cys Gly Asp Ser Gln Gly Gly Gly Ile Ser
            180                 185                 190

Leu Ala Val Gly Gly Ile Asp Pro Arg Val Lys Ala Val Met Pro Asp
```

```
                195                 200                 205
Val Pro Phe Leu Cys Asp Phe Pro Arg Ala Val Gln Thr Ala Val Arg
    210                 215                 220
Asp Pro Tyr Leu Glu Ile Val Arg Phe Leu Ala Gln His Arg Glu Lys
225                 230                 235                 240
Lys Ala Ala Val Phe Glu Thr Leu Asn Tyr Phe Asp Cys Val Asn Phe
                245                 250                 255
Ala Arg Arg Ser Lys Ala Pro Ala Leu Phe Ser Val Ala Leu Met Asp
            260                 265                 270
Glu Val Cys Pro Pro Ser Thr Val Tyr Gly Ala Phe Asn Ala Tyr Ala
        275                 280                 285
Gly Glu Lys Thr Ile Thr Glu Tyr Glu Phe Asn Asn His Glu Gly Gly
    290                 295                 300
Gln Gly Tyr Gln Glu Arg Gln Gln Met Thr Trp Leu Ser Arg Leu Phe
305                 310                 315                 320
Gly Val Gly

<210> SEQ ID NO 28
<211> LENGTH: 329
<212> TYPE: PRT
<213> ORGANISM: Geobacillus stearothermophilus

<400> SEQUENCE: 28

Met Phe Asp Met Pro Leu Ala Gln Leu Gln Lys Tyr Met Gly Thr Asn
1               5                   10                  15
Pro Lys Pro Ala Asp Phe Ala Asp Phe Trp Ser Arg Ala Leu Glu Glu
            20                  25                  30
Leu Ser Ala Gln Ser Leu His Tyr Glu Leu Ile Pro Ala Thr Phe Gln
        35                  40                  45
Thr Thr Val Ala Ser Cys Tyr His Leu Tyr Phe Thr Gly Val Gly Gly
    50                  55                  60
Ala Arg Val His Cys Gln Leu Val Lys Pro Arg Glu Gln Lys Gln Lys
65                  70                  75                  80
Gly Pro Gly Leu Val Trp Phe His Gly Tyr His Thr Asn Ser Gly Asp
                85                  90                  95
Trp Val Asp Lys Leu Ala Tyr Ala Ala Ala Gly Phe Thr Val Leu Ala
            100                 105                 110
Met Asp Cys Arg Gly Gln Gly Gly Lys Ser Glu Asp Asn Leu Gln Val
        115                 120                 125
Lys Gly Pro Thr Leu Lys Gly His Ile Ile Arg Gly Ile Glu Asp Pro
    130                 135                 140
Asn Pro His His Leu Tyr Tyr Arg Asn Val Phe Leu Asp Thr Val Gln
145                 150                 155                 160
Ala Val Arg Ile Leu Cys Ser Met Asp His Ile Asp Arg Glu Arg Ile
                165                 170                 175
Gly Val Tyr Gly Ala Ser Gln Gly Gly Ala Leu Ala Leu Ala Cys Ala
            180                 185                 190
Ala Leu Glu Pro Ser Val Val Lys Lys Ala Val Val Leu Tyr Pro Phe
        195                 200                 205
Leu Ser Asp Tyr Lys Arg Ala Gln Glu Leu Asp Met Lys Asn Thr Ala
    210                 215                 220
Tyr Glu Glu Ile His Tyr Tyr Phe Arg Phe Leu Asp Pro Thr His Glu
225                 230                 235                 240
Arg Glu Glu Glu Val Phe Tyr Lys Leu Gly Tyr Ile Asp Ile Gln Leu
```

245                 250                 255

Leu Ala Asp Arg Ile Cys Ala Asp Val Leu Trp Ala Val Ala Leu Glu
            260                 265                 270

Asp His Ile Cys Pro Pro Ser Thr Gln Phe Ala Val Tyr Asn Lys Ile
        275                 280                 285

Lys Ser Lys Lys Asp Met Val Leu Phe Tyr Glu Tyr Gly His Glu Tyr
    290                 295                 300

Leu Pro Thr Met Gly Asp Arg Ala Tyr Leu Phe Phe Cys Pro Ile Phe
305                 310                 315                 320

Phe Pro Ile Gln Lys Arg Asn Val Lys
                325

<210> SEQ ID NO 29
<211> LENGTH: 20
<212> TYPE: PRT
<213> ORGANISM: artificial sequence
<220> FEATURE:
<223> OTHER INFORMATION: Synthetic construct

<400> SEQUENCE: 29

Ala His Pro Glu Ser Leu Gly Ile Lys Tyr Ala Leu Asp Gly Asn Ser
1               5                   10                  15

Asp Pro His Ala
            20

<210> SEQ ID NO 30
<211> LENGTH: 20
<212> TYPE: PRT
<213> ORGANISM: artificial sequence
<220> FEATURE:
<223> OTHER INFORMATION: Synthetic construct

<400> SEQUENCE: 30

Ala Ser Val Ser Asn Tyr Pro Pro Ile His His Leu Ala Thr Ser Asn
1               5                   10                  15

Thr Thr Val Asn
            20

<210> SEQ ID NO 31
<211> LENGTH: 14
<212> TYPE: PRT
<213> ORGANISM: artificial sequence
<220> FEATURE:
<223> OTHER INFORMATION: Synthetic construct

<400> SEQUENCE: 31

Asp Glu Cys Met Glu Pro Leu Asn Ala Ala His Cys Trp Arg
1               5                   10

<210> SEQ ID NO 32
<211> LENGTH: 14
<212> TYPE: PRT
<213> ORGANISM: artificial sequence
<220> FEATURE:
<223> OTHER INFORMATION: Synthetic construct

<400> SEQUENCE: 32

Asp Glu Cys Met His Gly Ser Asp Val Glu Phe Cys Thr Ser
1               5                   10

<210> SEQ ID NO 33
<211> LENGTH: 14
<212> TYPE: PRT

```
<213> ORGANISM: artificial sequence
<220> FEATURE:
<223> OTHER INFORMATION: Synthetic construct

<400> SEQUENCE: 33

Asp Leu Cys Ser Met Gln Met Met Asn Thr Gly Cys His Tyr
1               5                   10

<210> SEQ ID NO 34
<211> LENGTH: 14
<212> TYPE: PRT
<213> ORGANISM: artificial sequence
<220> FEATURE:
<223> OTHER INFORMATION: Synthetic construct

<400> SEQUENCE: 34

Asp Leu Cys Ser Ser Pro Ser Thr Trp Gly Ser Cys Ile Arg
1               5                   10

<210> SEQ ID NO 35
<211> LENGTH: 20
<212> TYPE: PRT
<213> ORGANISM: artificial sequence
<220> FEATURE:
<223> OTHER INFORMATION: Synthetic construct

<400> SEQUENCE: 35

Asp Pro Asn Glu Ser Asn Tyr Glu Asn Ala Thr Thr Val Ser Gln Pro
1               5                   10                  15

Thr Arg His Leu
            20

<210> SEQ ID NO 36
<211> LENGTH: 20
<212> TYPE: PRT
<213> ORGANISM: artificial sequence
<220> FEATURE:
<223> OTHER INFORMATION: Synthetic construct

<400> SEQUENCE: 36

Glu Pro Thr His Pro Thr Met Arg Ala Gln Met His Gln Ser Leu Arg
1               5                   10                  15

Ser Ser Ser Pro
            20

<210> SEQ ID NO 37
<211> LENGTH: 20
<212> TYPE: PRT
<213> ORGANISM: artificial sequence
<220> FEATURE:
<223> OTHER INFORMATION: Synthetic construct

<400> SEQUENCE: 37

Gly Asn Thr Asp Thr Thr Pro Pro Asn Ala Val Met Glu Pro Thr Val
1               5                   10                  15

Gln His Lys Trp
            20

<210> SEQ ID NO 38
<211> LENGTH: 15
<212> TYPE: PRT
<213> ORGANISM: artificial sequence
<220> FEATURE:
<223> OTHER INFORMATION: Synthetic construct

<400> SEQUENCE: 38
```

```
Asn Gly Pro Asp Met Val Gln Ser Val Gly Lys His Lys Asn Ser
1               5                   10                  15
```

<210> SEQ ID NO 39
<211> LENGTH: 15
<212> TYPE: PRT
<213> ORGANISM: artificial sequence
<220> FEATURE:
<223> OTHER INFORMATION: Synthetic construct

<400> SEQUENCE: 39

```
Asn Gly Pro Glu Val Arg Gln Ile Pro Ala Asn Phe Glu Lys Leu
1               5                   10                  15
```

<210> SEQ ID NO 40
<211> LENGTH: 20
<212> TYPE: PRT
<213> ORGANISM: artificial sequence
<220> FEATURE:
<223> OTHER INFORMATION: Synthetic construct

<400> SEQUENCE: 40

```
Asn Asn Thr Ser Ala Asp Asn Pro Pro Glu Thr Asp Ser Lys His His
1               5                   10                  15

Leu Ser Met Ser
            20
```

<210> SEQ ID NO 41
<211> LENGTH: 20
<212> TYPE: PRT
<213> ORGANISM: artificial sequence
<220> FEATURE:
<223> OTHER INFORMATION: Synthetic construct

<400> SEQUENCE: 41

```
Asn Asn Thr Trp Pro Glu Gly Ala Gly His Thr Met Pro Ser Thr Asn
1               5                   10                  15

Ile Arg Gln Ala
            20
```

<210> SEQ ID NO 42
<211> LENGTH: 20
<212> TYPE: PRT
<213> ORGANISM: artificial sequence
<220> FEATURE:
<223> OTHER INFORMATION: Synthetic construct

<400> SEQUENCE: 42

```
Asn Pro Thr Ala Thr Pro His Met Lys Asp Pro Met His Ser Asn Ala
1               5                   10                  15

His Ser Ser Ala
            20
```

<210> SEQ ID NO 43
<211> LENGTH: 20
<212> TYPE: PRT
<213> ORGANISM: artificial sequence
<220> FEATURE:
<223> OTHER INFORMATION: Synthetic construct

<400> SEQUENCE: 43

```
Asn Pro Thr Asp His Ile Pro Ala Asn Ser Thr Asn Ser Arg Val Ser
1               5                   10                  15

Lys Gly Asn Thr
```

-continued

```
                    20

<210> SEQ ID NO 44
<211> LENGTH: 15
<212> TYPE: PRT
<213> ORGANISM: artificial sequence
<220> FEATURE:
<223> OTHER INFORMATION: Synthetic construct

<400> SEQUENCE: 44

Asn Pro Thr Asp Ser Thr His Met Met His Ala Arg Asn His Glu
1               5                   10                  15

<210> SEQ ID NO 45
<211> LENGTH: 14
<212> TYPE: PRT
<213> ORGANISM: artificial sequence
<220> FEATURE:
<223> OTHER INFORMATION: Synthetic construct

<400> SEQUENCE: 45

Gln His Cys Ile Thr Glu Arg Leu His Pro Pro Cys Thr Lys
1               5                   10

<210> SEQ ID NO 46
<211> LENGTH: 14
<212> TYPE: PRT
<213> ORGANISM: artificial sequence
<220> FEATURE:
<223> OTHER INFORMATION: Synthetic construct

<400> SEQUENCE: 46

Thr Pro Cys Ala Pro Ala Ser Phe Asn Pro His Cys Ser Arg
1               5                   10

<210> SEQ ID NO 47
<211> LENGTH: 14
<212> TYPE: PRT
<213> ORGANISM: artificial sequence
<220> FEATURE:
<223> OTHER INFORMATION: Synthetic construct

<400> SEQUENCE: 47

Thr Pro Cys Ala Thr Tyr Pro His Phe Ser Gly Cys Arg Ala
1               5                   10

<210> SEQ ID NO 48
<211> LENGTH: 20
<212> TYPE: PRT
<213> ORGANISM: artificial sequence
<220> FEATURE:
<223> OTHER INFORMATION: Synthetic construct

<400> SEQUENCE: 48

Trp Cys Thr Asp Phe Cys Thr Arg Ser Thr Pro Thr Ser Thr Arg
1               5                   10                  15

Ser Thr Thr Ser
            20

<210> SEQ ID NO 49
<211> LENGTH: 20
<212> TYPE: PRT
<213> ORGANISM: artificial sequence
<220> FEATURE:
<223> OTHER INFORMATION: Synthetic construct

<400> SEQUENCE: 49
```

```
Ala Pro Pro Leu Lys Thr Tyr Met Gln Glu Arg Glu Leu Thr Met Ser
1               5                   10                  15

Gln Asn Lys Asp
            20
```

<210> SEQ ID NO 50
<211> LENGTH: 20
<212> TYPE: PRT
<213> ORGANISM: artificial sequence
<220> FEATURE:
<223> OTHER INFORMATION: Synthetic construct

<400> SEQUENCE: 50

```
Glu Pro Pro Thr Arg Thr Arg Val Asn Asn His Thr Val Thr Val Gln
1               5                   10                  15

Ala Gln Gln His
            20
```

<210> SEQ ID NO 51
<211> LENGTH: 14
<212> TYPE: PRT
<213> ORGANISM: artificial sequence
<220> FEATURE:
<223> OTHER INFORMATION: Synthetic construct

<400> SEQUENCE: 51

```
Gly Tyr Cys Leu Arg Gly Asp Glu Pro Ala Val Cys Ser Gly
1               5                   10
```

<210> SEQ ID NO 52
<211> LENGTH: 20
<212> TYPE: PRT
<213> ORGANISM: artificial sequence
<220> FEATURE:
<223> OTHER INFORMATION: Synthetic construct

<400> SEQUENCE: 52

```
Leu Ser Ser Lys Asp Phe Gly Val Thr Asn Thr Asp Gln Arg Thr Tyr
1               5                   10                  15

Asp Tyr Thr Thr
            20
```

<210> SEQ ID NO 53
<211> LENGTH: 14
<212> TYPE: PRT
<213> ORGANISM: artificial sequence
<220> FEATURE:
<223> OTHER INFORMATION: Synthetic construct

<400> SEQUENCE: 53

```
Asn Phe Cys Glu Thr Gln Leu Asp Leu Ser Val Cys Thr Val
1               5                   10
```

<210> SEQ ID NO 54
<211> LENGTH: 14
<212> TYPE: PRT
<213> ORGANISM: artificial sequence
<220> FEATURE:
<223> OTHER INFORMATION: Synthetic construct

<400> SEQUENCE: 54

```
Asn Thr Cys Gln Pro Thr Lys Asn Ala Thr Pro Cys Ser Ala
1               5                   10
```

-continued

```
<210> SEQ ID NO 55
<211> LENGTH: 20
<212> TYPE: PRT
<213> ORGANISM: artificial sequence
<220> FEATURE:
<223> OTHER INFORMATION: Synthetic construct

<400> SEQUENCE: 55

Pro Ser Glu Pro Glu Arg Arg Asp Arg Asn Ile Ala Ala Asn Ala Gly
1               5                   10                  15

Arg Phe Asn Thr
            20

<210> SEQ ID NO 56
<211> LENGTH: 18
<212> TYPE: PRT
<213> ORGANISM: artificial sequence
<220> FEATURE:
<223> OTHER INFORMATION: Synthetic construct

<400> SEQUENCE: 56

Thr His Asn Met Ser His Phe Pro Pro Ser Gly His Pro Lys Arg Thr
1               5                   10                  15

Ala Thr

<210> SEQ ID NO 57
<211> LENGTH: 14
<212> TYPE: PRT
<213> ORGANISM: artificial sequence
<220> FEATURE:
<223> OTHER INFORMATION: Synthetic construct

<400> SEQUENCE: 57

Thr Thr Cys Pro Thr Met Gly Thr Tyr His Val Cys Trp Leu
1               5                   10

<210> SEQ ID NO 58
<211> LENGTH: 20
<212> TYPE: PRT
<213> ORGANISM: artificial sequence
<220> FEATURE:
<223> OTHER INFORMATION: Synthetic construct

<400> SEQUENCE: 58

Tyr Cys Ala Asp His Thr Pro Asp Pro Ala Asn Pro Asn Lys Ile Cys
1               5                   10                  15

Gly Tyr Ser His
            20

<210> SEQ ID NO 59
<211> LENGTH: 20
<212> TYPE: PRT
<213> ORGANISM: artificial sequence
<220> FEATURE:
<223> OTHER INFORMATION: Synthetic construct

<400> SEQUENCE: 59

Ala Ala Asn Pro His Thr Glu Trp Asp Arg Asp Ala Phe Gln Leu Ala
1               5                   10                  15

Met Pro Pro Lys
            20

<210> SEQ ID NO 60
<211> LENGTH: 20
<212> TYPE: PRT
```

```
<213> ORGANISM: artificial sequence
<220> FEATURE:
<223> OTHER INFORMATION: Synthetic construct

<400> SEQUENCE: 60

Asp Leu His Pro Met Asp Pro Ser Asn Lys Arg Pro Asp Asn Pro Ser
1               5                   10                  15

Asp Leu His Thr
            20

<210> SEQ ID NO 61
<211> LENGTH: 14
<212> TYPE: PRT
<213> ORGANISM: artificial sequence
<220> FEATURE:
<223> OTHER INFORMATION: Synthetic construct

<400> SEQUENCE: 61

Glu Ser Cys Val Ser Asn Ala Leu Met Asn Gln Cys Ile Tyr
1               5                   10

<210> SEQ ID NO 62
<211> LENGTH: 20
<212> TYPE: PRT
<213> ORGANISM: artificial sequence
<220> FEATURE:
<223> OTHER INFORMATION: Synthetic construct

<400> SEQUENCE: 62

His Asn Lys Ala Asp Ser Trp Asp Pro Asp Leu Pro Pro His Ala Gly
1               5                   10                  15

Met Ser Leu Gly
            20

<210> SEQ ID NO 63
<211> LENGTH: 20
<212> TYPE: PRT
<213> ORGANISM: artificial sequence
<220> FEATURE:
<223> OTHER INFORMATION: Synthetic construct

<400> SEQUENCE: 63

Leu Asn Asp Gln Arg Lys Pro Gly Pro Pro Thr Met Pro Thr His Ser
1               5                   10                  15

Pro Ala Val Gly
            20

<210> SEQ ID NO 64
<211> LENGTH: 14
<212> TYPE: PRT
<213> ORGANISM: artificial sequence
<220> FEATURE:
<223> OTHER INFORMATION: Synthetic construct

<400> SEQUENCE: 64

Asn Thr Cys Ala Thr Ser Pro Asn Ser Tyr Thr Cys Ser Asn
1               5                   10

<210> SEQ ID NO 65
<211> LENGTH: 14
<212> TYPE: PRT
<213> ORGANISM: artificial sequence
<220> FEATURE:
<223> OTHER INFORMATION: Synthetic construct

<400> SEQUENCE: 65
```

```
Ser Asp Cys Thr Ala Gly Leu Val Pro Pro Leu Cys Ala Thr
1               5                  10
```

<210> SEQ ID NO 66
<211> LENGTH: 20
<212> TYPE: PRT
<213> ORGANISM: artificial sequence
<220> FEATURE:
<223> OTHER INFORMATION: Synthetic construct

<400> SEQUENCE: 66

```
Thr Ile Glu Ser Ser Gln His Ser Arg Thr His Gln Gln Asn Tyr Gly
1               5                  10                  15

Ser Thr Lys Thr
            20
```

<210> SEQ ID NO 67
<211> LENGTH: 20
<212> TYPE: PRT
<213> ORGANISM: artificial sequence
<220> FEATURE:
<223> OTHER INFORMATION: Synthetic construct

<400> SEQUENCE: 67

```
Val Gly Thr Met Lys Gln His Pro Thr Thr Thr Gln Pro Pro Arg Val
1               5                  10                  15

Ser Ala Thr Asn
            20
```

<210> SEQ ID NO 68
<211> LENGTH: 20
<212> TYPE: PRT
<213> ORGANISM: artificial sequence
<220> FEATURE:
<223> OTHER INFORMATION: Synthetic construct

<400> SEQUENCE: 68

```
Tyr Ser Glu Thr Pro Asn Asp Gln Lys Pro Asn Pro His Tyr Lys Val
1               5                  10                  15

Ser Gly Thr Lys
            20
```

<210> SEQ ID NO 69
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 69

```
Asn Gly Asn Asn His Thr Asp Ile Pro Asn Arg Ser Ser Tyr Thr Gly
1               5                  10                  15

Gly Ser Phe Ala
            20
```

<210> SEQ ID NO 70
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 70

```
Thr Met Thr Asn His Val Tyr Asn Ser Tyr Thr Glu Lys His Ser Ser
```

```
Thr His Arg Ser
            20

<210> SEQ ID NO 71
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 71

Thr Thr Tyr His Tyr Lys Asn Ile Tyr Gln Glu Ser Tyr Gln Gln Arg
1               5                   10                  15

Asn Pro Ala Val
            20

<210> SEQ ID NO 72
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 72

Val Glu Pro Ala Thr Lys Asn Met Arg Glu Ala Arg Ser Ser Thr Gln
1               5                   10                  15

Met Arg Arg Ile
            20

<210> SEQ ID NO 73
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 73

Tyr Leu Leu Pro Lys Asp Gln Thr Thr Ala Pro Gln Val Thr Pro Ile
1               5                   10                  15

Val Gln His Lys
            20

<210> SEQ ID NO 74
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 74

Ala Ser Asn Leu Asp Ser Thr Phe Thr Ala Ile Asn Thr Pro Ala Cys
1               5                   10                  15

Cys Thr

<210> SEQ ID NO 75
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 75

Glu Phe Pro Tyr Tyr Asn Asp Asn Pro Pro Asn Pro Glu Arg His Thr
```

```
1               5                   10                  15

Leu Arg

<210> SEQ ID NO 76
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 76

Gly Met Pro Thr Arg Tyr Tyr His Asn Thr Pro Pro His Leu Thr Pro
1               5                   10                  15

Lys Phe

<210> SEQ ID NO 77
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 77

His Lys Asn Ala Ile Gln Pro Val Asn Asp Ala Thr Thr Leu Asp Thr
1               5                   10                  15

Thr Met

<210> SEQ ID NO 78
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 78

Ala Val Val Pro Ala Asp Leu Asn Asp His Ala Asn His Leu Ser
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 79

Asp Leu Gly Thr Phe Pro Asn Arg Thr Leu Lys Met Ala Ala His
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 80

Phe Asp Gly Ile Gly Leu Gly Thr Ala Thr Arg His Gln Asn Arg
1               5                   10                  15

<210> SEQ ID NO 81
<211> LENGTH: 15
<212> TYPE: PRT
<213> ORGANISM: Artificial Sequence
<220> FEATURE:
```

```
<223> OTHER INFORMATION: Synthetic oral-surface binding peptide

<400> SEQUENCE: 81

Gln Ala Ala Gln Val His Met Met Gln His Ser Arg Pro Thr Thr
1               5                   10                  15

<210> SEQ ID NO 82
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 82

Ser Glu Ala Arg Ala Arg Thr Phe Asn Asp His Thr Thr Pro Met Pro
1               5                   10                  15

Ile Ile

<210> SEQ ID NO 83
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 83

Glu Leu Asp His Asp Ser Arg His Tyr Met Asn Gly Leu Gln Arg Lys
1               5                   10                  15

Val Thr

<210> SEQ ID NO 84
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 84

Gly Pro Gln His Val Leu Met Gln Asp Thr His Gln Gly Tyr Ala Phe
1               5                   10                  15

Asp Asn

<210> SEQ ID NO 85
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 85

Thr Thr Gly Ser Ser Ser Gln Ala Asp Thr Ser Ala Ser Met Ser Ile
1               5                   10                  15

Val Pro Ala His
            20

<210> SEQ ID NO 86
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 86

Lys Ala Pro Ile Ala Asn Met Leu Gln Pro His Ser Tyr Gln Tyr Ser
```

Val Ala

<210> SEQ ID NO 87
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 87

Thr Tyr Gln Gly Val Pro Ser Trp Pro Ala Val Ile Asp Asp Ala Ile
1               5                   10                  15

Arg Arg

<210> SEQ ID NO 88
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 88

Val Asn Pro Asn Trp Val Glu Thr Gln Ala Leu His Gln Pro Pro Gly
1               5                   10                  15

Asn Thr

<210> SEQ ID NO 89
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 89

Asp His Asn Asn Arg Gln His Ala Val Glu Val Arg Glu Asn Lys Thr
1               5                   10                  15

His Thr Ala Arg
            20

<210> SEQ ID NO 90
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 90

Ile Tyr Pro Asn Glu Ser Met Ser Thr Ser Asn Val Arg Gly Pro Tyr
1               5                   10                  15

His Pro

<210> SEQ ID NO 91
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 91

His Asp Pro Asn His Leu Thr His Gln Ala Arg Thr Ile Tyr Arg Asn
1               5                   10                  15

Ala Asn His Thr

20

<210> SEQ ID NO 92
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 92

Ser Asn Ala Thr Met Tyr Asn Ile Gln Ser His Ser His His Gln
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 93

Ala Asn Glu Leu Ser Thr Tyr Ala Gln Thr Asn Pro Gly Ser Gly
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Synthetic oral-surface binding peptide

<400> SEQUENCE: 94

Asp Thr Ile His Pro Asn Lys Met Lys Ser Pro Ser Ser Pro Leu
1               5                   10                  15

<210> SEQ ID NO 95
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 95

Ala Pro Pro Thr Tyr Gln Thr Ala Ser Tyr Pro His Asn Leu Pro Ser
1               5                   10                  15

Lys Arg Lys Met
            20

<210> SEQ ID NO 96
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 96

Gln Val Pro Asp Tyr Leu Ser Pro Thr His Gln Lys Lys Ala Phe Leu
1               5                   10                  15

Glu Ile Pro Thr
            20

<210> SEQ ID NO 97
<211> LENGTH: 20
<212> TYPE: PRT
<213> ORGANISM: Artificial Sequence
<220> FEATURE:

<223> OTHER INFORMATION: Synthetic oral-surface binding peptide

<400> SEQUENCE: 97

Thr Asn Asp Leu His Ala Asn Pro Phe Thr Gly Thr Tyr Ile Ala Pro
1               5                   10                  15

Asp Pro Thr Ser
            20

<210> SEQ ID NO 98
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 98

His Lys Asn Glu Asn Ile Met Gln Tyr Asn Val Asn Asp Arg Trp His
1               5                   10                  15

Ile Thr Pro Ala
            20

<210> SEQ ID NO 99
<211> LENGTH: 18
<212> TYPE: PRT
<213> ORGANISM: Artificial Sequence
<220> FEATURE:
<223> OTHER INFORMATION: Synthetic oral-surface binding peptide

<400> SEQUENCE: 99

Ile Asp Gly Pro His His Ser Pro Val His Arg Tyr His Thr Pro Ser
1               5                   10                  15

Ile Thr

<210> SEQ ID NO 100
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 100

Ala Ile Glu Tyr Gln His Ser Ala Thr Thr Pro Trp Thr Met Arg Thr
1               5                   10                  15

Arg Leu Pro Pro
            20

<210> SEQ ID NO 101
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 101

Glu Phe Tyr Pro Phe Ala Glu Val Pro Pro Glu Lys Ser Gly Ile Gly
1               5                   10                  15

Arg Gln Val Phe
            20

<210> SEQ ID NO 102
<211> LENGTH: 20
<212> TYPE: PRT
<213> ORGANISM: Artificial Sequence
<220> FEATURE:

<223> OTHER INFORMATION: Synthetic oral-surface binding peptide

<400> SEQUENCE: 102

Gly Val His Gln Tyr Ser Arg Pro Thr Val Pro Ser Tyr Leu Trp Thr
1               5                   10                  15

Ser Gly Gln His
            20

<210> SEQ ID NO 103
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 103

Gly Tyr Gln Pro His Tyr Val Asp His Thr Ile Gly Trp Gln Pro Met
1               5                   10                  15

Ile Arg Pro Asn
            20

<210> SEQ ID NO 104
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 104

Gln Phe Asn Gln Thr Ser His Ser Phe Met His Gly Thr Ser Gly Tyr
1               5                   10                  15

Val Pro Gly Lys
            20

<210> SEQ ID NO 105
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 105

Ser Phe Ser Trp His Arg Gly Asp Trp Glu Leu Gly His Gln Ser Lys
1               5                   10                  15

Thr Met Gly Met
            20

<210> SEQ ID NO 106
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 106

Ser Met Trp His Asp Ile Thr Lys Arg Tyr Arg Asn Pro Ser Glu Met
1               5                   10                  15

Val Ser Ala Tyr
            20

<210> SEQ ID NO 107
<211> LENGTH: 20
<212> TYPE: PRT
<213> ORGANISM: Artificial Sequence -continued

```
<220> FEATURE:
<223> OTHER INFORMATION: Synthetic oral-surface binding peptide

<400> SEQUENCE: 107

Thr His Gly Asn Lys His Gln Ser Trp Thr Tyr Pro Ser Glu Ile Asn
1               5                   10                  15

His Lys Asn Tyr
            20

<210> SEQ ID NO 108
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 108

Trp His Glu Pro His Gln Phe Ser Gly Glu Asn Thr Asp Tyr Ser Ser
1               5                   10                  15

Ser Met Gly Thr
            20

<210> SEQ ID NO 109
<211> LENGTH: 20
<212> TYPE: PRT
<213> ORGANISM: Artificial Sequence
<220> FEATURE:
<223> OTHER INFORMATION: Synthetic oral-surface binding peptide

<400> SEQUENCE: 109

Thr His Gly Asn Lys His Gln Ser Trp Thr Tyr Pro Ser Glu Ile Asn
1               5                   10                  15

His Lys Asn Tyr
            20

<210> SEQ ID NO 110
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 110

Asp Gly Tyr Lys Leu Gln Thr Ser Leu Asp Trp Gln Met Trp Asn Pro
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 111

Phe Pro Ser Lys Trp Tyr Asn His His Arg His Ile Thr Gly His Val
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 112
```

Gly Gly Met Gly Ala Leu Glu Ser Tyr Arg Gln Trp Asn His Leu Ala
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 113

Gly Ile Asn Lys Gly Gln Arg Pro Pro Trp Glu Ser Trp His Glu Asn
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 114

Gly Tyr Gly Gln Tyr Val Ser Gln Gln Thr Trp Ala His Ser Asn Lys
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 115

His Asp His Leu Ser Trp Trp Gly Gln Phe Asp Arg Gln Asn Leu Leu
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 116

Met Pro Gly His Gln Glu Ser Ile Lys Val Gln Asn Trp Asn Arg Val
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 117

Asn Leu His Ser Pro Trp Pro Ser His Ala Ala His His Trp Ser Thr
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 118

Asn Gln Gln Met Lys Leu Val Pro Gln His Trp His Arg Ala Gln Pro

<210> SEQ ID NO 119
<211> LENGTH: 16
<212> TYPE: PRT
<213> ORGANISM: Artificial Sequence
<220> FEATURE:
<223> OTHER INFORMATION: Synthetic oral-surface binding peptide

<400> SEQUENCE: 119

Ser Glu Lys Trp Phe Asn Pro Gly Pro Trp Pro Lys Leu Ala Thr Gln
1               5                   10                  15

<210> SEQ ID NO 120
<211> LENGTH: 25
<212> TYPE: PRT
<213> ORGANISM: Artificial Sequence
<220> FEATURE:
<223> OTHER INFORMATION: synthetic construct

<400> SEQUENCE: 120

Ser Ser Arg Pro Asn Gly Asn Asn His Thr Asp Ile Pro Asn Arg Ser
1               5                   10                  15

Ser Tyr Thr Gly Gly Ser Phe Ala Lys
            20                  25

<210> SEQ ID NO 121
<211> LENGTH: 25
<212> TYPE: PRT
<213> ORGANISM: Artificial Sequence
<220> FEATURE:
<223> OTHER INFORMATION: synthetic construct

<400> SEQUENCE: 121

Ser Ser Arg Pro Thr Met Thr Asn His Val Tyr Asn Ser Tyr Thr Glu
1               5                   10                  15

Lys His Ser Ser Thr His Arg Ser Lys
            20                  25

<210> SEQ ID NO 122
<211> LENGTH: 25
<212> TYPE: PRT
<213> ORGANISM: Artificial Sequence
<220> FEATURE:
<223> OTHER INFORMATION: synthetic construct

<400> SEQUENCE: 122

Ser Ser Arg Pro Thr Thr Tyr His Tyr Lys Asn Ile Tyr Gln Glu Ser
1               5                   10                  15

Tyr Gln Gln Arg Asn Pro Ala Val Lys
            20                  25

<210> SEQ ID NO 123
<211> LENGTH: 25
<212> TYPE: PRT
<213> ORGANISM: Artificial Sequence
<220> FEATURE:
<223> OTHER INFORMATION: synthetic construct

<400> SEQUENCE: 123

Ser Ser Arg Pro Val Glu Pro Ala Thr Lys Asn Met Arg Glu Ala Arg
1               5                   10                  15

Ser Ser Thr Gln Met Arg Arg Ile Lys
            20                  25

```
<210> SEQ ID NO 124
<211> LENGTH: 25
<212> TYPE: PRT
<213> ORGANISM: Artificial Sequence
<220> FEATURE:
<223> OTHER INFORMATION: synthetic construct

<400> SEQUENCE: 124

Ser Ser Arg Pro Tyr Leu Leu Pro Lys Asp Gln Thr Thr Ala Pro Gln
1               5                   10                  15

Val Thr Pro Ile Val Gln His Lys Lys
            20                  25

<210> SEQ ID NO 125
<211> LENGTH: 23
<212> TYPE: PRT
<213> ORGANISM: Artificial Sequence
<220> FEATURE:
<223> OTHER INFORMATION: synthetic construct

<400> SEQUENCE: 125

Ser Ser Arg Pro Glu Phe Pro Tyr Tyr Asn Asp Asn Pro Pro Asn Pro
1               5                   10                  15

Glu Arg His Thr Leu Arg Lys
            20

<210> SEQ ID NO 126
<211> LENGTH: 20
<212> TYPE: PRT
<213> ORGANISM: Artificial Sequence
<220> FEATURE:
<223> OTHER INFORMATION: synthetic construct

<400> SEQUENCE: 126

Ser Ser Arg Pro Asp Leu Gly Thr Phe Pro Asn Arg Thr Leu Lys Met
1               5                   10                  15

Ala Ala His Lys
            20

<210> SEQ ID NO 127
<211> LENGTH: 20
<212> TYPE: PRT
<213> ORGANISM: Artificial Sequence
<220> FEATURE:
<223> OTHER INFORMATION: synthetic construct

<400> SEQUENCE: 127

Ser Ser Arg Pro Phe Asp Gly Ile Gly Leu Gly Thr Ala Thr Arg His
1               5                   10                  15

Gln Asn Arg Lys
            20

<210> SEQ ID NO 128
<211> LENGTH: 20
<212> TYPE: PRT
<213> ORGANISM: Artificial Sequence
<220> FEATURE:
<223> OTHER INFORMATION: synthetic construct

<400> SEQUENCE: 128

Ser Ser Arg Pro Gln Ala Ala Gln Val His Met Met Gln His Ser Arg
1               5                   10                  15

Pro Thr Thr Lys
            20
```

<210> SEQ ID NO 129
<211> LENGTH: 23
<212> TYPE: PRT
<213> ORGANISM: Artificial Sequence
<220> FEATURE:
<223> OTHER INFORMATION: synthetic construct

<400> SEQUENCE: 129

Ser Ser Arg Pro Ser Glu Ala Arg Ala Arg Thr Phe Asn Asp His Thr
1               5                   10                  15

Thr Pro Met Pro Ile Ile Lys
            20

<210> SEQ ID NO 130
<211> LENGTH: 23
<212> TYPE: PRT
<213> ORGANISM: Artificial Sequence
<220> FEATURE:
<223> OTHER INFORMATION: synthetic construct

<400> SEQUENCE: 130

Ser Ser Arg Pro Glu Leu Asp His Asp Ser Arg His Tyr Met Asn Gly
1               5                   10                  15

Leu Gln Arg Lys Val Thr Lys
            20

<210> SEQ ID NO 131
<211> LENGTH: 23
<212> TYPE: PRT
<213> ORGANISM: Artificial Sequence
<220> FEATURE:
<223> OTHER INFORMATION: synthetic construct

<400> SEQUENCE: 131

Ser Ser Arg Pro Gly Pro Gln His Val Leu Met Gln Asp Thr His Gln
1               5                   10                  15

Gly Tyr Ala Phe Asp Asn Lys
            20

<210> SEQ ID NO 132
<211> LENGTH: 25
<212> TYPE: PRT
<213> ORGANISM: Artificial Sequence
<220> FEATURE:
<223> OTHER INFORMATION: synthetic construct

<400> SEQUENCE: 132

Ser Ser Arg Pro Thr Thr Gly Ser Ser Gln Ala Asp Thr Ser Ala
1               5                   10                  15

Ser Met Ser Ile Val Pro Ala His Lys
            20                  25

<210> SEQ ID NO 133
<211> LENGTH: 23
<212> TYPE: PRT
<213> ORGANISM: Artificial Sequence
<220> FEATURE:
<223> OTHER INFORMATION: synthetic construct

<400> SEQUENCE: 133

Ser Ser Arg Pro Thr Tyr Gln Gly Val Pro Ser Trp Pro Ala Val Ile
1               5                   10                  15

Asp Asp Ala Ile Arg Arg Lys

```
                 20

<210> SEQ ID NO 134
<211> LENGTH: 23
<212> TYPE: PRT
<213> ORGANISM: Artificial Sequence
<220> FEATURE:
<223> OTHER INFORMATION: synthetic construct

<400> SEQUENCE: 134

Ser Ser Arg Pro Val Asn Pro Asn Trp Val Glu Thr Gln Ala Leu His
1               5                   10                  15

Gln Pro Pro Gly Asn Thr Lys
            20

<210> SEQ ID NO 135
<211> LENGTH: 23
<212> TYPE: PRT
<213> ORGANISM: Artificial Sequence
<220> FEATURE:
<223> OTHER INFORMATION: synthetic construct

<400> SEQUENCE: 135

Ser Ser Arg Pro Ile Tyr Pro Asn Glu Ser Met Ser Thr Ser Asn Val
1               5                   10                  15

Arg Gly Pro Tyr His Pro Lys
            20

<210> SEQ ID NO 136
<211> LENGTH: 25
<212> TYPE: PRT
<213> ORGANISM: Artificial Sequence
<220> FEATURE:
<223> OTHER INFORMATION: synthetic construct

<400> SEQUENCE: 136

Ser Ser Arg Pro His Asp Pro Asn His Leu Thr His Gln Ala Arg Thr
1               5                   10                  15

Ile Tyr Arg Asn Ala Asn His Thr Lys
            20                  25

<210> SEQ ID NO 137
<211> LENGTH: 25
<212> TYPE: PRT
<213> ORGANISM: Artificial Sequence
<220> FEATURE:
<223> OTHER INFORMATION: synthetic construct

<400> SEQUENCE: 137

Ser Ser Arg Pro Ala Pro Pro Thr Tyr Gln Thr Ala Ser Tyr Pro His
1               5                   10                  15

Asn Leu Pro Ser Lys Arg Lys Met Lys
            20                  25

<210> SEQ ID NO 138
<211> LENGTH: 25
<212> TYPE: PRT
<213> ORGANISM: Artificial Sequence
<220> FEATURE:
<223> OTHER INFORMATION: synthetic construct

<400> SEQUENCE: 138

Ser Ser Arg Pro Gln Val Pro Asp Tyr Leu Ser Pro Thr His Gln Lys
1               5                   10                  15
```

Lys Ala Phe Leu Glu Ile Pro Thr Lys
            20                  25

<210> SEQ ID NO 139
<211> LENGTH: 25
<212> TYPE: PRT
<213> ORGANISM: Artificial Sequence
<220> FEATURE:
<223> OTHER INFORMATION: synthetic construct

<400> SEQUENCE: 139

Ser Ser Arg Pro His Lys Asn Glu Asn Ile Met Gln Tyr Asn Val Asn
1               5                   10                  15

Asp Arg Trp His Ile Thr Pro Ala Lys
            20                  25

<210> SEQ ID NO 140
<211> LENGTH: 15
<212> TYPE: PRT
<213> ORGANISM: artificial sequence
<220> FEATURE:
<223> OTHER INFORMATION: synthetic construct

<400> SEQUENCE: 140

Ser Asn Ala Thr Met Tyr Asn Ile Gln Ser His Ser His His Gln
1               5                   10                  15

<210> SEQ ID NO 141
<211> LENGTH: 15
<212> TYPE: PRT
<213> ORGANISM: artificial sequence
<220> FEATURE:
<223> OTHER INFORMATION: synthetic construct

<400> SEQUENCE: 141

Gln Ala Ala Gln Val His Met Met Gln His Ser Arg Pro Thr Thr
1               5                   10                  15

<210> SEQ ID NO 142
<211> LENGTH: 15
<212> TYPE: PRT
<213> ORGANISM: artificial sequence
<220> FEATURE:
<223> OTHER INFORMATION: synthetic construct

<400> SEQUENCE: 142

His Asp Pro Tyr Thr Met Lys Ser Ala Leu Arg Gln Ser Thr Ser
1               5                   10                  15

<210> SEQ ID NO 143
<211> LENGTH: 15
<212> TYPE: PRT
<213> ORGANISM: artificial sequence
<220> FEATURE:
<223> OTHER INFORMATION: synthetic construct

<400> SEQUENCE: 143

Asp Leu Gly Thr Phe Pro Asn Arg Thr Leu Lys Met Ala Ala His
1               5                   10                  15

<210> SEQ ID NO 144
<211> LENGTH: 15
<212> TYPE: PRT
<213> ORGANISM: artificial sequence
<220> FEATURE:
<223> OTHER INFORMATION: synthetic construct

```
<400> SEQUENCE: 144

Asp Thr Ile His Pro Asn Lys Met Lys Ser Pro Ser Ser Pro Leu
1               5                   10                  15

<210> SEQ ID NO 145
<211> LENGTH: 15
<212> TYPE: PRT
<213> ORGANISM: artificial sequence
<220> FEATURE:
<223> OTHER INFORMATION: synthetic construct

<400> SEQUENCE: 145

Gly Ser Asn Asn His Leu Pro Ser Thr Val Pro Arg Leu Thr Val
1               5                   10                  15

<210> SEQ ID NO 146
<211> LENGTH: 18
<212> TYPE: PRT
<213> ORGANISM: artificial sequence
<220> FEATURE:
<223> OTHER INFORMATION: synthetic construct

<400> SEQUENCE: 146

Ser Asn Pro Ile Pro Asn Phe Ala His Asp Leu Arg His Ser Lys Tyr
1               5                   10                  15

Asn Ser

<210> SEQ ID NO 147
<211> LENGTH: 18
<212> TYPE: PRT
<213> ORGANISM: artificial sequence
<220> FEATURE:
<223> OTHER INFORMATION: synthetic construct

<400> SEQUENCE: 147

Thr Lys Pro Pro Arg Thr Pro Thr Ala Asn Thr Ser Arg Pro His His
1               5                   10                  15

Asn Phe

<210> SEQ ID NO 148
<211> LENGTH: 20
<212> TYPE: PRT
<213> ORGANISM: artificial sequence
<220> FEATURE:
<223> OTHER INFORMATION: synthetic construct

<400> SEQUENCE: 148

Ala Asn Ser Gly Phe Pro Ile Trp Leu Gln Lys Tyr Pro Trp Ser Glu
1               5                   10                  15

Val Gln Gln Glu
            20

<210> SEQ ID NO 149
<211> LENGTH: 19
<212> TYPE: PRT
<213> ORGANISM: artificial sequence
<220> FEATURE:
<223> OTHER INFORMATION: synthetic construct

<400> SEQUENCE: 149

Ala Thr Pro Arg Leu Thr Pro Glu Ala His His Lys Ala Gly Asn Trp
1               5                   10                  15

Tyr Ala Ser
```

```
<210> SEQ ID NO 150
<211> LENGTH: 20
<212> TYPE: PRT
<213> ORGANISM: artificial sequence
<220> FEATURE:
<223> OTHER INFORMATION: synthetic construct

<400> SEQUENCE: 150

Ala Thr Pro Ser Gln His Arg Tyr Gly Leu Met Gln Asn His Ala Pro
1               5                   10                  15

Asn Gly Ile Glu
            20

<210> SEQ ID NO 151
<211> LENGTH: 16
<212> TYPE: PRT
<213> ORGANISM: artificial sequence
<220> FEATURE:
<223> OTHER INFORMATION: synthetic construct

<400> SEQUENCE: 151

Gly Met Gly Ser Glu Val Leu Ser Gln Tyr Pro Gln Ala Pro Val Gly
1               5                   10                  15

<210> SEQ ID NO 152
<211> LENGTH: 21
<212> TYPE: PRT
<213> ORGANISM: artificial sequence
<220> FEATURE:
<223> OTHER INFORMATION: synthetic construct

<400> SEQUENCE: 152

Thr Thr Tyr His Tyr Lys Asn Ile Tyr Gln Glu Ser Tyr Gln Gln Arg
1               5                   10                  15

Asn Pro Ala Val Lys
            20

<210> SEQ ID NO 153
<211> LENGTH: 16
<212> TYPE: PRT
<213> ORGANISM: artificial sequence
<220> FEATURE:
<223> OTHER INFORMATION: synthetic construct

<400> SEQUENCE: 153

Ser Asn Ala Thr Met Tyr Asn Ile Gln Ser His Ser His Gln Lys
1               5                   10                  15

<210> SEQ ID NO 154
<211> LENGTH: 16
<212> TYPE: PRT
<213> ORGANISM: artificial sequence
<220> FEATURE:
<223> OTHER INFORMATION: synthetic construct

<400> SEQUENCE: 154

Gln Ala Ala Gln Val His Met Met Gln His Ser Arg Pro Thr Thr Lys
1               5                   10                  15

<210> SEQ ID NO 155
<211> LENGTH: 16
<212> TYPE: PRT
<213> ORGANISM: artificial sequence
<220> FEATURE:
<223> OTHER INFORMATION: synthetic construct
```

```
<400> SEQUENCE: 155

His Asp Pro Tyr Thr Met Lys Ser Ala Leu Arg Gln Ser Thr Ser Lys
1               5                   10                  15

<210> SEQ ID NO 156
<211> LENGTH: 16
<212> TYPE: PRT
<213> ORGANISM: artificial sequence
<220> FEATURE:
<223> OTHER INFORMATION: synthetic construct

<400> SEQUENCE: 156

Asp Leu Gly Thr Phe Pro Asn Arg Thr Leu Lys Met Ala Ala His Lys
1               5                   10                  15

<210> SEQ ID NO 157
<211> LENGTH: 16
<212> TYPE: PRT
<213> ORGANISM: artificial sequence
<220> FEATURE:
<223> OTHER INFORMATION: synthetic construct

<400> SEQUENCE: 157

Asp Thr Ile His Pro Asn Lys Met Lys Ser Pro Ser Ser Pro Leu Lys
1               5                   10                  15

<210> SEQ ID NO 158
<211> LENGTH: 16
<212> TYPE: PRT
<213> ORGANISM: artificial sequence
<220> FEATURE:
<223> OTHER INFORMATION: synthetic construct

<400> SEQUENCE: 158

Gly Ser Asn Asn His Leu Pro Ser Thr Val Pro Arg Leu Thr Val Lys
1               5                   10                  15

<210> SEQ ID NO 159
<211> LENGTH: 19
<212> TYPE: PRT
<213> ORGANISM: artificial sequence
<220> FEATURE:
<223> OTHER INFORMATION: synthetic construct

<400> SEQUENCE: 159

Ser Asn Pro Ile Pro Asn Phe Ala His Asp Leu Arg His Ser Lys Tyr
1               5                   10                  15

Asn Ser Lys

<210> SEQ ID NO 160
<211> LENGTH: 19
<212> TYPE: PRT
<213> ORGANISM: artificial sequence
<220> FEATURE:
<223> OTHER INFORMATION: synthetic construct

<400> SEQUENCE: 160

Thr Lys Pro Pro Arg Thr Pro Thr Ala Asn Thr Ser Arg Pro His His
1               5                   10                  15

Asn Phe Lys

<210> SEQ ID NO 161
<211> LENGTH: 21
<212> TYPE: PRT
<213> ORGANISM: artificial sequence
```

```
<220> FEATURE:
<223> OTHER INFORMATION: synthetic construct

<400> SEQUENCE: 161

Ala Asn Ser Gly Phe Pro Ile Trp Leu Gln Lys Tyr Pro Trp Ser Glu
1               5                   10                  15

Val Gln Gln Glu Lys
            20

<210> SEQ ID NO 162
<211> LENGTH: 21
<212> TYPE: PRT
<213> ORGANISM: artificial sequence
<220> FEATURE:
<223> OTHER INFORMATION: synthetic construct

<400> SEQUENCE: 162

Ala Thr Pro Ser Gln His Arg Tyr Gly Leu Met Gln Asn His Ala Pro
1               5                   10                  15

Asn Gly Ile Glu Lys
            20

<210> SEQ ID NO 163
<211> LENGTH: 17
<212> TYPE: PRT
<213> ORGANISM: artificial sequence
<220> FEATURE:
<223> OTHER INFORMATION: synthetic construct

<400> SEQUENCE: 163

Gly Met Gly Ser Glu Val Leu Ser Gln Tyr Pro Gln Ala Pro Val Gly
1               5                   10                  15

Lys

<210> SEQ ID NO 164
<211> LENGTH: 8
<212> TYPE: PRT
<213> ORGANISM: Artificial Sequence
<220> FEATURE:
<223> OTHER INFORMATION: Synthetic construct - caspace 3 cleavable
      linker

<400> SEQUENCE: 164

Leu Glu Ser Gly Asp Glu Val Asp
1               5

<210> SEQ ID NO 165
<211> LENGTH: 37
<212> TYPE: PRT
<213> ORGANISM: Artificial Sequence
<220> FEATURE:
<223> OTHER INFORMATION: synthetic construct

<400> SEQUENCE: 165

Thr Ser Thr Ser Lys Ala Ser Thr Thr Thr Ser Ser Lys Thr Thr
1               5                   10                  15

Thr Thr Ser Ser Lys Thr Thr Thr Thr Thr Ser Lys Thr Ser Thr Thr
            20                  25                  30

Ser Ser Ser Ser Thr
        35

<210> SEQ ID NO 166
<211> LENGTH: 22
<212> TYPE: PRT
```

```
<213> ORGANISM: Artificial Sequence
<220> FEATURE:
<223> OTHER INFORMATION: synthetic construct

<400> SEQUENCE: 166

Gly Gln Gly Gly Tyr Gly Gly Leu Gly Ser Gln Gly Ala Gly Arg Gly
1               5                   10                  15

Gly Leu Gly Gly Gln Gly
            20

<210> SEQ ID NO 167
<211> LENGTH: 10
<212> TYPE: PRT
<213> ORGANISM: Artificial Sequence
<220> FEATURE:
<223> OTHER INFORMATION: synthetic construct

<400> SEQUENCE: 167

Gly Pro Gly Gly Tyr Gly Pro Gly Gln Gln
1               5                   10

<210> SEQ ID NO 168
<211> LENGTH: 9
<212> TYPE: PRT
<213> ORGANISM: Artificial Sequence
<220> FEATURE:
<223> OTHER INFORMATION: synthetic construct

<400> SEQUENCE: 168

Gly Gly Ser Gly Pro Gly Ser Gly Gly
1               5

<210> SEQ ID NO 169
<211> LENGTH: 5
<212> TYPE: PRT
<213> ORGANISM: Artificial Sequence
<220> FEATURE:
<223> OTHER INFORMATION: synthetic construct

<400> SEQUENCE: 169

Gly Gly Pro Lys Lys
1               5

<210> SEQ ID NO 170
<211> LENGTH: 5
<212> TYPE: PRT
<213> ORGANISM: Artificial Sequence
<220> FEATURE:
<223> OTHER INFORMATION: synthetic construct

<400> SEQUENCE: 170

Gly Pro Gly Val Gly
1               5

<210> SEQ ID NO 171
<211> LENGTH: 7
<212> TYPE: PRT
<213> ORGANISM: Artificial Sequence
<220> FEATURE:
<223> OTHER INFORMATION: synthetic construct

<400> SEQUENCE: 171

Gly Gly Gly Cys Gly Gly Gly
1               5

<210> SEQ ID NO 172
```

-continued

```
<211> LENGTH: 4
<212> TYPE: PRT
<213> ORGANISM: Artificial Sequence
<220> FEATURE:
<223> OTHER INFORMATION: synthetic construct

<400> SEQUENCE: 172

Gly Gly Gly Cys
1

<210> SEQ ID NO 173
<211> LENGTH: 14
<212> TYPE: PRT
<213> ORGANISM: Artificial Sequence
<220> FEATURE:
<223> OTHER INFORMATION: synthetic construct

<400> SEQUENCE: 173

Pro His Met Ala Ser Met Thr Gly Gly Gln Gln Met Gly Ser
1               5                   10

<210> SEQ ID NO 174
<211> LENGTH: 16
<212> TYPE: PRT
<213> ORGANISM: Artificial Sequence
<220> FEATURE:
<223> OTHER INFORMATION: synthetic construct

<400> SEQUENCE: 174

Gly Pro Glu Glu Ala Ala Lys Lys Glu Glu Ala Ala Lys Lys Pro Ala
1               5                   10                  15

<210> SEQ ID NO 175
<211> LENGTH: 14
<212> TYPE: PRT
<213> ORGANISM: Artificial Sequence
<220> FEATURE:
<223> OTHER INFORMATION: synthetic construct

<400> SEQUENCE: 175

Gly Ser Gly Gly Gly Gly Ser Gly Ser Gly Gly Gly Gly Ser
1               5                   10

<210> SEQ ID NO 176
<211> LENGTH: 37
<212> TYPE: PRT
<213> ORGANISM: Artificial Sequence
<220> FEATURE:
<223> OTHER INFORMATION: synthetic construct

<400> SEQUENCE: 176

Gly Pro Glu Pro Glu Pro Glu Pro Glu Pro Ile Pro Glu Pro Pro Lys
1               5                   10                  15

Glu Ala Pro Val Val Ile Glu Lys Pro Lys Pro Lys Pro Lys Pro Lys
            20                  25                  30

Pro Lys Pro Pro Ala
        35

<210> SEQ ID NO 177
<211> LENGTH: 18
<212> TYPE: PRT
<213> ORGANISM: artificial sequence
<220> FEATURE:
<223> OTHER INFORMATION: synthetic construct

<400> SEQUENCE: 177
```

Gly Pro Gly Ser Gly Ala Gly Ser Pro Gly Ser Ala Gly Gly Pro
1               5                   10                  15

Gly Ser

<210> SEQ ID NO 178
<211> LENGTH: 431
<212> TYPE: PRT
<213> ORGANISM: artificial sequence
<220> FEATURE:
<223> OTHER INFORMATION: synthetic construct

<400> SEQUENCE: 178

Met Ala Phe Phe Asp Leu Pro Leu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
                325                 330                 335

Ser Ala Gly Gly Pro Gly Ser Pro Ser Ala Gln Ser Gln Leu Pro Asp

```
                        340                 345                 350
Lys His Ser Gly Leu His Glu Arg Ala Pro Gln Arg Tyr Gly Pro Glu
                355                 360                 365
Pro Glu Pro Glu Pro Glu Pro Ile Pro Glu Pro Pro Lys Glu Ala Pro
        370                 375                 380
Val Val Ile Glu Lys Pro Lys Pro Lys Pro Lys Pro Lys Pro Lys Pro
385                 390                 395                 400
Pro Ala His Asp His Lys Asn Gln Lys Glu Thr His Gln Arg His Ala
                405                 410                 415
Ala Gly Ser Gly Gly Gly Gly Ser Pro His His His His His His
            420                 425                 430

<210> SEQ ID NO 179
<211> LENGTH: 353
<212> TYPE: PRT
<213> ORGANISM: artificial sequence
<220> FEATURE:
<223> OTHER INFORMATION: synthetic construct

<400> SEQUENCE: 179

Met Ala Phe Phe Asp Leu Pro Leu Glu Glu Leu Lys Lys Tyr Arg Pro
1               5                   10                  15
Glu Arg Tyr Glu Glu Lys Asp Phe Asp Glu Phe Trp Glu Glu Thr Leu
                20                  25                  30
Ala Glu Ser Glu Lys Phe Pro Leu Asp Pro Val Phe Glu Arg Met Glu
                35                  40                  45
Ser His Leu Lys Thr Val Glu Ala Tyr Asp Val Thr Phe Ser Gly Tyr
            50                  55                  60
Arg Gly Gln Arg Ile Lys Gly Trp Leu Leu Val Pro Lys Leu Glu Glu
65                  70                  75                  80
Glu Lys Leu Pro Cys Val Val Gln Tyr Ile Gly Tyr Asn Gly Gly Arg
                85                  90                  95
Gly Phe Pro His Asp Trp Leu Phe Trp Pro Ser Met Gly Tyr Ile Cys
                100                 105                 110
Phe Val Met Asp Thr Arg Gly Gln Gly Ser Gly Trp Leu Lys Gly Asp
            115                 120                 125
Thr Pro Asp Tyr Pro Glu Gly Pro Val Asp Pro Gln Tyr Pro Gly Phe
        130                 135                 140
Met Thr Arg Gly Ile Leu Asp Pro Arg Thr Tyr Tyr Arg Arg Val
145                 150                 155                 160
Phe Thr Asp Ala Val Arg Ala Val Glu Ala Ala Ser Phe Pro Gln
                165                 170                 175
Val Asp Gln Glu Arg Ile Val Ile Ala Gly Gly Ser Gln Gly Gly Gly
            180                 185                 190
Ile Ala Leu Ala Val Ser Ala Leu Ser Lys Lys Ala Lys Ala Leu Leu
        195                 200                 205
Cys Asp Val Pro Phe Leu Cys His Phe Arg Arg Ala Val Gln Leu Val
    210                 215                 220
Asp Thr His Pro Tyr Ala Glu Ile Thr Asn Phe Leu Lys Thr His Arg
225                 230                 235                 240
Asp Lys Glu Glu Ile Val Phe Arg Thr Leu Ser Tyr Phe Asp Gly Val
                245                 250                 255
Asn Phe Ala Ala Arg Ala Lys Ile Pro Ala Leu Phe Ser Val Gly Leu
            260                 265                 270
Met Asp Asn Ile Ser Pro Pro Ser Thr Val Phe Ala Ala Tyr Asn Tyr
```

```
            275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
                325                 330                 335

Ser Ala Gly Gly Pro Gly Ser Gly Lys Gly Lys Gly Lys Gly Lys Gly
                340                 345                 350

Lys

<210> SEQ ID NO 180
<211> LENGTH: 359
<212> TYPE: PRT
<213> ORGANISM: artificial sequence
<220> FEATURE:
<223> OTHER INFORMATION: synthetic construct

<400> SEQUENCE: 180

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285
```

-continued

```
Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly Pro Gly Ser Gly Gly Ala Gly Ser Pro Gly
                325                 330                 335

Ser Ala Gly Gly Pro Gly Ser Gly Lys Gly Lys Gly Lys Gly Lys Gly
            340                 345                 350

Lys His His His His His His
            355
```

<210> SEQ ID NO 181
<211> LENGTH: 375
<212> TYPE: PRT
<213> ORGANISM: artificial sequence
<220> FEATURE:
<223> OTHER INFORMATION: synthetic construct

<400> SEQUENCE: 181

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
        50                  55                  60

Arg Gly Gln Arg Ile Lys Gly Trp Leu Leu Val Pro Lys Leu Glu Glu
65              70                  75                  80

Glu Lys Leu Pro Cys Val Val Gln Tyr Ile Gly Tyr Asn Gly Gly Arg
            85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
            130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
            165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
            245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
            275                 280                 285
```

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Gly Ala Gly Ser Pro Gly
                325                 330                 335

Ser Ala Gly Gly Pro Gly Ser Thr Lys Pro Pro Arg Thr Pro Thr Ala
            340                 345                 350

Asn Thr Ser Arg Pro His His Asn Phe Gly Ser Gly Gly Gly Gly Ser
            355                 360                 365

Pro His His His His His His
      370                 375

<210> SEQ ID NO 182
<211> LENGTH: 431
<212> TYPE: PRT
<213> ORGANISM: artificial sequence
<220> FEATURE:
<223> OTHER INFORMATION: synthetic construct

<400> SEQUENCE: 182

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

```
Met Asp Asn Ile Thr Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Pro Gly Ser Gly Ala Gly Ser Pro Gly
                325                 330                 335

Ser Ala Gly Gly Pro Gly Ser Pro Ser Ala Gln Ser Gln Leu Pro Asp
                340                 345                 350

Lys His Ser Gly Leu His Glu Arg Ala Pro Gln Arg Tyr Gly Pro Glu
            355                 360                 365

Pro Glu Pro Glu Pro Glu Pro Ile Pro Glu Pro Pro Lys Glu Ala Pro
            370                 375                 380

Val Val Ile Glu Lys Pro Lys Pro Lys Pro Lys Pro Lys Pro Lys Pro
385                 390                 395                 400

Pro Ala His Asp His Lys Asn Gln Lys Glu Thr His Gln Arg His Ala
                405                 410                 415

Ala Gly Ser Gly Gly Gly Gly Ser Pro His His His His His His
                420                 425                 430

<210> SEQ ID NO 183
<211> LENGTH: 359
<212> TYPE: PRT
<213> ORGANISM: artificial sequence
<220> FEATURE:
<223> OTHER INFORMATION: synthetic construct

<400> SEQUENCE: 183

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
                35                  40                  45

Ser His Leu Lys Thr Val Glu Ala Tyr Asp Val Thr Phe Ser Gly Tyr
        50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
            195                 200                 205
```

-continued

```
Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Thr Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Gly Pro Gly Ser Gly Ala Gly Ser Pro Gly
                325                 330                 335

Ser Ala Gly Gly Pro Gly Ser Gly Lys Gly Lys Gly Lys Gly
            340                 345                 350

Lys His His His His His His
        355

<210> SEQ ID NO 184
<211> LENGTH: 386
<212> TYPE: PRT
<213> ORGANISM: artificial sequence
<220> FEATURE:
<223> OTHER INFORMATION: synthetic construct

<400> SEQUENCE: 184

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
            35                  40                  45

Ser His Leu Lys Thr Val Glu Ala Tyr Asp Val Thr Phe Ser Gly Tyr
        50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205
```

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Pro Glu Gly Pro Gly Ser Gly Gly
                325                 330                 335

Ala Gly Ser Pro Gly Ser Ala Gly Gly Pro Gly Ser Glu Pro Glu Pro
            340                 345                 350

Glu Trp Lys Thr Lys Lys Ile Leu Leu Ser Arg Thr Arg Arg Ile Met
            355                 360                 365

Arg Gln Val Val Arg Ser Val Met His Lys Ile Trp His His His His
    370                 375                 380

His His
385

<210> SEQ ID NO 185
<211> LENGTH: 387
<212> TYPE: PRT
<213> ORGANISM: artificial sequence
<220> FEATURE:
<223> OTHER INFORMATION: synthetic construct

<400> SEQUENCE: 185

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

```
Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Pro Glu Pro Glu Pro Glu Pro Glu
                325                 330                 335

Gly Pro Gly Ser Gly Gly Ala Gly Ser Pro Gly Ser Ala Gly Gly Pro
            340                 345                 350

Gly Ser Trp Lys Thr Lys Lys Ile Leu Leu Ser Arg Thr Arg Arg Ile
        355                 360                 365

Met Arg Gln Val Val Arg Ser Val Met His Lys Ile Trp His His His
370                 375                 380

His His His
385

<210> SEQ ID NO 186
<211> LENGTH: 386
<212> TYPE: PRT
<213> ORGANISM: artificial sequence
<220> FEATURE:
<223> OTHER INFORMATION: synthetic construct

<400> SEQUENCE: 186

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140
```

```
Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gly Gly Gly
            180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
                210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
                260                 265                 270

Met Asp Asn Ile Ser Pro Pro Ser Thr Val Phe Ala Ala Tyr Asn Tyr
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Val Gln Val Lys Phe Leu Lys Lys
305                 310                 315                 320

Leu Phe Glu Lys Gly Glu Pro Glu Pro Glu Gly Pro Gly Ser Gly Gly
                325                 330                 335

Ala Gly Ser Pro Gly Ser Ala Gly Gly Pro Gly Ser Glu Pro Glu Pro
                340                 345                 350

Glu Pro Leu Trp Arg Arg Ile Thr Lys Arg Lys Leu Val Arg Pro Val
                355                 360                 365

Ala Thr Leu Met Trp Tyr Trp Phe Thr Ser Lys Arg His His His
                370                 375                 380

His His
385

<210> SEQ ID NO 187
<211> LENGTH: 387
<212> TYPE: PRT
<213> ORGANISM: artificial sequence
<220> FEATURE:
<223> OTHER INFORMATION: synthetic construct

<400> SEQUENCE: 187

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
                35                  40                  45

Ser His Leu Lys Thr Val Glu Ala Tyr Asp Val Thr Phe Ser Gly Tyr
                50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
                100                 105                 110
```

```
Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
        130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
                180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
            210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
            290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Pro Glu Pro Glu Pro Glu Pro Glu
                325                 330                 335

Gly Pro Gly Ser Gly Gly Ala Gly Ser Pro Gly Ser Ala Gly Gly Pro
            340                 345                 350

Gly Ser Pro Leu Trp Arg Arg Ile Thr Lys Arg Lys Leu Val Arg Pro
            355                 360                 365

Val Ala Thr Leu Met Trp Tyr Trp Phe Thr Ser Lys Arg His His His
            370                 375                 380

His His His
385

<210> SEQ ID NO 188
<211> LENGTH: 382
<212> TYPE: PRT
<213> ORGANISM: artificial sequence
<220> FEATURE:
<223> OTHER INFORMATION: synthetic construct

<400> SEQUENCE: 188

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Gly Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80
```

-continued

```
Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Gly Pro Gly Ser Gly Gly Ala Gly
                325                 330                 335

Ser Pro Gly Ser Ala Gly Gly Pro Gly Ser Glu Pro Glu Arg Met Leu
            340                 345                 350

Ser Arg Ile Leu Arg Met Phe Val Arg Ile Leu Lys Arg Glu Arg Leu
        355                 360                 365

Ser Gln Val Arg Gly Leu Phe Val His His His His His
    370                 375                 380
```

<210> SEQ ID NO 189
<211> LENGTH: 383
<212> TYPE: PRT
<213> ORGANISM: artificial sequence
<220> FEATURE:
<223> OTHER INFORMATION: synthetic construct

<400> SEQUENCE: 189

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60
```

```
Arg Gly Gln Arg Ile Lys Gly Trp Leu Leu Val Pro Lys Leu Glu Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Pro Glu Pro Glu Pro Glu Gly Pro Gly Ser
                325                 330                 335

Gly Gly Ala Gly Ser Pro Gly Ser Ala Gly Gly Pro Gly Ser Arg Met
            340                 345                 350

Leu Ser Arg Ile Leu Arg Met Phe Val Arg Ile Leu Lys Arg Glu Arg
        355                 360                 365

Leu Ser Gln Val Arg Gly Leu Phe Val His His His His His His
    370                 375                 380

<210> SEQ ID NO 190
<211> LENGTH: 390
<212> TYPE: PRT
<213> ORGANISM: artificial sequence
<220> FEATURE:
<223> OTHER INFORMATION: synthetic construct

<400> SEQUENCE: 190

Met Ala Phe Phe Asp Leu Pro Leu Glu Glu Leu Lys Lys Tyr Arg Pro
 1               5                  10                  15

Glu Arg Tyr Glu Glu Lys Asp Phe Asp Glu Phe Trp Glu Glu Thr Leu
                20                  25                  30

Ala Glu Ser Glu Lys Phe Pro Leu Asp Pro Val Phe Glu Arg Met Glu
            35                  40                  45
```

Ser His Leu Lys Thr Val Glu Ala Tyr Asp Val Thr Phe Ser Gly Tyr
        50                  55                  60

Arg Gly Gln Arg Ile Lys Gly Trp Leu Leu Val Pro Lys Leu Glu Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
        130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
        210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
        290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Pro Glu Pro Glu Gly Pro Gly Ser
                325                 330                 335

Gly Gly Ala Gly Ser Pro Gly Ser Ala Gly Gly Pro Gly Ser Glu Pro
            340                 345                 350

Glu Pro Glu Pro Glu Leu Arg Phe Leu Ala Arg Arg Phe Leu Lys Leu
        355                 360                 365

Arg Arg Ala Arg Lys Trp Trp Asn Ala Trp Lys Val Trp Val Thr Arg
370                 375                 380

His His His His His His
385                 390

<210> SEQ ID NO 191
<211> LENGTH: 391
<212> TYPE: PRT
<213> ORGANISM: artificial sequence
<220> FEATURE:
<223> OTHER INFORMATION: synthetic construct

<400> SEQUENCE: 191

Met Ala Phe Phe Asp Leu Pro Leu Glu Glu Leu Lys Lys Tyr Arg Pro
 1               5                  10                  15

```
Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Leu Lys Gly Asp
            115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly
            180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Ser Pro Pro Ser Thr Val Phe Ala Ala Tyr Asn Tyr
            275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly Glu Pro Glu Pro Glu Pro Glu Pro Glu Pro Glu
                325                 330                 335

Pro Glu Pro Glu Gly Pro Gly Ser Gly Gly Ala Gly Ser Pro Gly Ser
            340                 345                 350

Ala Gly Gly Pro Gly Ser Leu Arg Phe Leu Ala Arg Arg Phe Leu Lys
            355                 360                 365

Leu Arg Arg Ala Arg Lys Trp Trp Asn Ala Trp Lys Val Trp Val Thr
            370                 375                 380

Arg His His His His His
385                 390

<210> SEQ ID NO 192
<211> LENGTH: 426
<212> TYPE: PRT
<213> ORGANISM: artificial sequence
<220> FEATURE:
```

<223> OTHER INFORMATION: synthetic construct

<400> SEQUENCE: 192

```
Met Gln Leu Phe Asp Leu Ser Leu Glu Glu Leu Lys Lys Tyr Lys Pro
1               5                   10                  15

Lys Lys Thr Ala Arg Pro Asp Phe Ser Asp Phe Trp Lys Lys Ser Leu
            20                  25                  30

Glu Glu Leu Arg Gln Val Glu Ala Glu Pro Thr Leu Glu Ser Tyr Asp
        35                  40                  45

Tyr Pro Val Lys Gly Val Lys Val Tyr Arg Leu Thr Tyr Gln Ser Phe
    50                  55                  60

Gly His Ser Lys Ile Glu Gly Phe Tyr Ala Val Pro Asp Gln Thr Gly
65                  70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
            100                 105                 110

Phe Gly Met Leu Val Arg Gly Gln Gly Gly Ser Glu Asp Thr Ser Val
        115                 120                 125

Thr Pro Gly Gly His Ala Leu Gly Trp Met Thr Lys Gly Ile Leu Ser
    130                 135                 140

Lys Asp Thr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
                165                 170                 175

Val Ile Gly Gly Ser Gln Gly Gly Ala Leu Ala Ile Ala Ala Ala
            180                 185                 190

Leu Ser Asp Ile Pro Lys Val Val Ala Asp Tyr Pro Tyr Leu Ser
    195                 200                 205

Asn Phe Glu Arg Ala Val Asp Val Ala Leu Glu Gln Pro Tyr Leu Glu
    210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp
                245                 250                 255

Val Lys Gln Pro Thr Leu Met Ala Ile Gly Leu Ile Asp Lys Ile Thr
            260                 265                 270

Pro Pro Ser Thr Val Phe Ala Ala Tyr Asn His Leu Glu Thr Asp Lys
        275                 280                 285

Asp Leu Lys Val Tyr Arg Tyr Phe Gly His Glu Phe Ile Pro Ala Phe
    290                 295                 300

Gln Thr Glu Lys Leu Ser Phe Leu Gln Lys His Leu Leu Ser Thr
305                 310                 315                 320

Gly Pro Gly Ser Gly Gly Ala Gly Ser Pro Gly Ser Ala Gly Gly Pro
                325                 330                 335

Gly Ser Pro Ser Ala Gln Ser Gln Leu Pro Asp Lys His Ser Gly Leu
            340                 345                 350

His Glu Arg Ala Pro Gln Arg Tyr Gly Pro Glu Pro Glu Pro Glu Pro
        355                 360                 365

Glu Pro Ile Pro Glu Pro Pro Lys Glu Ala Pro Val Val Ile Glu Lys
    370                 375                 380

Pro Lys Pro Lys Pro Lys Pro Lys Pro Lys Pro Ala His Asp His
385                 390                 395                 400
```

Lys Asn Gln Lys Glu Thr His Gln Arg His Ala Ala Gly Ser Gly Gly
                405                 410                 415

Gly Gly Ser Pro His His His His His His
            420             425

<210> SEQ ID NO 193
<211> LENGTH: 372
<212> TYPE: PRT
<213> ORGANISM: artificial sequence
<220> FEATURE:
<223> OTHER INFORMATION: synthetic construct

<400> SEQUENCE: 193

Met Gln Leu Phe Asp Leu Ser Leu Glu Glu Leu Lys Lys Tyr Lys Pro
1               5                   10                  15

Lys Lys Thr Ala Arg Pro Asp Phe Ser Asp Phe Trp Lys Lys Ser Leu
            20                  25                  30

Glu Glu Leu Arg Gln Val Glu Ala Glu Pro Thr Leu Glu Ser Tyr Asp
        35                  40                  45

Tyr Pro Val Lys Gly Val Lys Val Tyr Arg Leu Thr Tyr Gln Ser Phe
    50                  55                  60

Gly His Ser Lys Ile Glu Gly Phe Tyr Ala Val Pro Asp Gln Thr Gly
65                  70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
            100                 105                 110

Phe Gly Met Leu Val Arg Gly Gln Gly Ser Glu Asp Thr Ser Val
        115                 120                 125

Thr Pro Gly Gly His Ala Leu Gly Trp Met Thr Lys Gly Ile Leu Ser
130                 135                 140

Lys Asp Thr Tyr Tyr Tyr Arg Gly Val Tyr Leu Asp Ala Val Arg Ala
145                 150                 155                 160

Leu Glu Val Ile Gln Ser Phe Pro Glu Val Asp His Arg Ile Gly
                165                 170                 175

Val Ile Gly Gly Ser Gln Gly Gly Ala Leu Ala Ile Ala Ala Ala
            180                 185                 190

Leu Ser Asp Ile Pro Lys Val Val Ala Asp Tyr Pro Tyr Leu Ser
        195                 200                 205

Asn Phe Glu Arg Ala Val Asp Val Ala Leu Glu Gln Pro Tyr Leu Glu
    210                 215                 220

Ile Asn Ser Tyr Phe Arg Arg Asn Ser Asp Pro Lys Val Glu Glu Lys
225                 230                 235                 240

Ala Phe Glu Thr Leu Ser Tyr Phe Asp Leu Ile Asn Leu Ala Gly Trp
                245                 250                 255

Val Lys Gln Pro Thr Leu Met Ala Ile Gly Leu Ile Asp Lys Ile Thr
            260                 265                 270

Pro Pro Ser Thr Val Phe Ala Ala Tyr Asn His Leu Glu Thr Asp Lys
        275                 280                 285

Asp Leu Lys Val Tyr Arg Tyr Phe Gly His Glu Phe Ile Pro Ala Phe
    290                 295                 300

Gln Thr Glu Lys Leu Ser Phe Leu Gln Lys His Leu Leu Ser Thr
305                 310                 315                 320

Gly Pro Gly Ser Gly Gly Ala Gly Ser Pro Gly Ser Ala Gly Gly Pro
                325                 330                 335

```
Gly Ser Asp Pro Thr Lys Pro Pro Arg Thr Pro Thr Ala Asn Thr Ser
            340                 345                 350

Arg Pro His His Asn Phe Gly Ser Gly Gly Gly Ser Pro His His
            355                 360                 365

His His His His
    370

<210> SEQ ID NO 194
<211> LENGTH: 429
<212> TYPE: PRT
<213> ORGANISM: artificial sequence
<220> FEATURE:
<223> OTHER INFORMATION: synthetic construct

<400> SEQUENCE: 194

Met Pro Phe Pro Asp Leu Ile Gln Pro Glu Leu Gly Ala Tyr Val Ser
1               5                   10                  15

Ser Val Gly Met Pro Asp Asp Phe Ala Gln Phe Trp Thr Ser Thr Ile
            20                  25                  30

Ala Glu Ala Arg Gln Ala Gly Gly Glu Val Ser Ile Val Gln Ala Gln
        35                  40                  45

Thr Thr Leu Lys Ala Val Gln Ser Phe Asp Val Thr Phe Pro Gly Tyr
    50                  55                  60

Gly Gly His Pro Ile Lys Gly Trp Leu Ile Leu Pro Thr His His Lys
65                  70                  75                  80

Gly Arg Leu Pro Leu Val Val Gln Tyr Ile Gly Tyr Gly Gly Gly Arg
                85                  90                  95

Gly Leu Ala His Glu Gln Leu His Trp Ala Ala Ser Gly Phe Ala Tyr
            100                 105                 110

Phe Arg Met Asp Thr Arg Gly Gln Gly Ser Asp Trp Ser Val Gly Glu
        115                 120                 125

Thr Ala Asp Pro Val Gly Ser Thr Ser Ser Ile Pro Gly Phe Met Thr
    130                 135                 140

Arg Gly Val Leu Asp Lys Asn Asp Tyr Tyr Tyr Arg Arg Leu Phe Thr
145                 150                 155                 160

Asp Ala Val Arg Ala Ile Asp Ala Leu Leu Gly Leu Asp Phe Val Asp
                165                 170                 175

Pro Glu Arg Ile Ala Val Cys Gly Asp Ser Gln Gly Gly Gly Ile Ser
            180                 185                 190

Leu Ala Val Gly Gly Ile Asp Pro Arg Val Lys Ala Val Met Pro Asp
        195                 200                 205

Val Pro Phe Leu Cys Asp Phe Pro Arg Ala Val Gln Thr Ala Val Arg
    210                 215                 220

Asp Pro Tyr Leu Glu Ile Val Arg Phe Leu Ala Gln His Arg Glu Lys
225                 230                 235                 240

Lys Ala Ala Val Phe Glu Thr Leu Asn Tyr Phe Asp Cys Val Asn Phe
                245                 250                 255

Ala Arg Arg Ser Lys Ala Pro Ala Leu Phe Ser Val Ala Leu Met Asp
            260                 265                 270

Glu Val Cys Pro Pro Ser Thr Val Tyr Gly Ala Phe Asn Ala Tyr Ala
        275                 280                 285

Gly Glu Lys Thr Ile Thr Glu Tyr Glu Phe Asn Asn His Glu Gly Gly
    290                 295                 300

Gln Gly Tyr Gln Glu Arg Gln Gln Met Thr Trp Leu Ser Arg Leu Phe
305                 310                 315                 320
```

```
Gly Val Gly Gly Pro Gly Ser Gly Gly Ala Gly Ser Pro Gly Ser Ala
            325                 330                 335

Gly Gly Pro Gly Ser Pro Ser Ala Gln Ser Gln Leu Pro Asp Lys His
            340                 345                 350

Ser Gly Leu His Glu Arg Ala Pro Gln Arg Tyr Gly Pro Glu Pro Glu
            355                 360                 365

Pro Glu Pro Glu Pro Ile Pro Glu Pro Pro Lys Glu Ala Pro Val Val
            370                 375                 380

Ile Glu Lys Pro Lys Pro Lys Pro Lys Pro Lys Pro Lys Pro Pro Ala
385                 390                 395                 400

His Asp His Lys Asn Gln Lys Glu Thr His Gln Arg His Ala Ala Gly
            405                 410                 415

Ser Gly Gly Gly Ser Pro His His His His His
            420                 425

<210> SEQ ID NO 195
<211> LENGTH: 375
<212> TYPE: PRT
<213> ORGANISM: artificial sequence
<220> FEATURE:
<223> OTHER INFORMATION: synthetic construct

<400> SEQUENCE: 195

Met Pro Phe Pro Asp Leu Ile Gln Pro Glu Leu Gly Ala Tyr Val Ser
1               5                   10                  15

Ser Val Gly Met Pro Asp Asp Phe Ala Gln Phe Trp Thr Ser Thr Ile
            20                  25                  30

Ala Glu Ala Arg Gln Ala Gly Glu Val Ser Ile Val Gln Ala Gln
        35                  40                  45

Thr Thr Leu Lys Ala Val Gln Ser Phe Asp Val Thr Phe Pro Gly Tyr
    50                  55                  60

Gly Gly His Pro Ile Lys Gly Trp Leu Ile Leu Pro Thr His His Lys
65                  70                  75                  80

Gly Arg Leu Pro Leu Val Val Gln Tyr Ile Gly Tyr Gly Gly Gly Arg
                85                  90                  95

Gly Leu Ala His Glu Gln Leu His Trp Ala Ala Ser Gly Phe Ala Tyr
            100                 105                 110

Phe Arg Met Asp Thr Arg Gly Gln Gly Ser Asp Trp Ser Val Gly Glu
        115                 120                 125

Thr Ala Asp Pro Val Gly Ser Thr Ser Ser Ile Pro Gly Phe Met Thr
    130                 135                 140

Arg Gly Val Leu Asp Lys Asn Asp Tyr Tyr Arg Arg Leu Phe Thr
145                 150                 155                 160

Asp Ala Val Arg Ala Ile Asp Ala Leu Leu Gly Leu Asp Phe Val Asp
                165                 170                 175

Pro Glu Arg Ile Ala Val Cys Gly Asp Ser Gln Gly Gly Gly Ile Ser
            180                 185                 190

Leu Ala Val Gly Gly Ile Asp Pro Arg Val Lys Ala Val Met Pro Asp
        195                 200                 205

Val Pro Phe Leu Cys Asp Phe Pro Arg Ala Val Gln Thr Ala Val Arg
    210                 215                 220

Asp Pro Tyr Leu Glu Ile Val Arg Phe Leu Ala Gln His Arg Glu Lys
225                 230                 235                 240

Lys Ala Ala Val Phe Glu Thr Leu Asn Tyr Phe Asp Cys Val Asn Phe
                245                 250                 255
```

```
Ala Arg Arg Ser Lys Ala Pro Ala Leu Phe Ser Val Ala Leu Met Asp
            260                 265                 270

Glu Val Cys Pro Pro Ser Thr Val Tyr Gly Ala Phe Asn Ala Tyr Ala
        275                 280                 285

Gly Glu Lys Thr Ile Thr Glu Tyr Glu Phe Asn Asn His Glu Gly Gly
    290                 295                 300

Gln Gly Tyr Gln Glu Arg Gln Gln Met Thr Trp Leu Ser Arg Leu Phe
305                 310                 315                 320

Gly Val Gly Gly Pro Gly Ser Gly Gly Ala Gly Ser Pro Gly Ser Ala
                325                 330                 335

Gly Gly Pro Gly Ser Asp Pro Thr Lys Pro Pro Arg Thr Pro Thr Ala
            340                 345                 350

Asn Thr Ser Arg Pro His His Asn Phe Gly Ser Gly Gly Gly Gly Ser
            355                 360                 365

Pro His His His His His His
    370                 375

<210> SEQ ID NO 196
<211> LENGTH: 418
<212> TYPE: PRT
<213> ORGANISM: artificial sequence
<220> FEATURE:
<223> OTHER INFORMATION: synthetic construct

<400> SEQUENCE: 196

Met Thr Lys Ile Asn Asn Trp Gln Asp Tyr Gln Gly Ser Ser Leu Lys
1               5                   10                  15

Pro Glu Asp Phe Asp Lys Phe Trp Asp Glu Lys Ile Asn Leu Val Ser
            20                  25                  30

Asn His Gln Phe Glu Phe Glu Leu Ile Glu Lys Asn Leu Ser Ser Lys
        35                  40                  45

Val Val Asn Phe Tyr His Leu Trp Phe Thr Ala Ile Asp Gly Ala Lys
    50                  55                  60

Ile His Ala Gln Leu Ile Val Pro Lys Asn Leu Lys Glu Lys Tyr Pro
65                  70                  75                  80

Ala Ile Leu Gln Phe His Gly Tyr His Cys Asp Ser Gly Asp Trp Val
                85                  90                  95

Asp Lys Ile Gly Ile Val Ala Glu Gly Asn Val Val Leu Ala Leu Asp
            100                 105                 110

Cys Arg Gly Gln Gly Gly Leu Ser Gln Asp Asn Ile Gln Thr Met Gly
        115                 120                 125

Met Thr Met Lys Gly Leu Ile Val Arg Gly Ile Asp Glu Gly Tyr Glu
130                 135                 140

Asn Leu Tyr Tyr Val Arg Gln Phe Met Asp Leu Ile Thr Ala Thr Lys
145                 150                 155                 160

Ile Leu Ser Glu Phe Asp Phe Val Asp Glu Thr Asn Ile Ser Ala Gln
                165                 170                 175

Gly Ala Ser Gln Gly Gly Ala Leu Ala Val Ala Cys Ala Ala Leu Ser
            180                 185                 190

Pro Leu Ile Lys Lys Val Thr Ala Thr Tyr Pro Phe Leu Ser Asp Tyr
        195                 200                 205

Arg Lys Ala Tyr Glu Leu Gly Ala Glu Glu Ser Ala Phe Glu Glu Leu
210                 215                 220

Pro Tyr Trp Phe Gln Phe Lys Asp Pro Leu His Leu Arg Glu Asp Trp
225                 230                 235                 240
```

```
Phe Phe Asn Gln Leu Glu Tyr Ile Asp Ile Gln Asn Leu Ala Pro Arg
                245                 250                 255

Ile Lys Ala Glu Val Ile Trp Ile Leu Gly Gly Lys Asp Thr Val Val
            260                 265                 270

Pro Pro Ile Thr Gln Met Ala Ala Tyr Asn Lys Ile Gln Ser Lys Lys
        275                 280                 285

Ser Leu Tyr Val Leu Pro Glu Tyr Gly His Glu Tyr Leu Pro Lys Ile
    290                 295                 300

Ser Asp Trp Leu Arg Glu Asn Gln Gly Pro Ser Gly Gly Ala Gly
305                 310                 315                 320

Ser Pro Gly Ser Ala Gly Gly Pro Gly Ser Pro Ser Ala Gln Ser Gln
                325                 330                 335

Leu Pro Asp Lys His Ser Gly Leu His Glu Arg Ala Pro Gln Arg Tyr
            340                 345                 350

Gly Pro Glu Pro Glu Pro Glu Pro Ile Pro Glu Pro Pro Lys
        355                 360                 365

Glu Ala Pro Val Val Ile Glu Lys Pro Lys Pro Lys Pro Lys Pro Lys
    370                 375                 380

Pro Lys Pro Pro Ala His Asp His Lys Asn Gln Lys Glu Thr His Gln
385                 390                 395                 400

Arg His Ala Ala Gly Ser Gly Gly Gly Ser Pro His His His His
                405                 410                 415

His His

<210> SEQ ID NO 197
<211> LENGTH: 363
<212> TYPE: PRT
<213> ORGANISM: artificial sequence
<220> FEATURE:
<223> OTHER INFORMATION: synthetic construct

<400> SEQUENCE: 197

Met Thr Lys Ile Asn Asn Trp Gln Asp Tyr Gln Gly Ser Ser Leu Lys
1               5                   10                  15

Pro Glu Asp Phe Asp Lys Phe Trp Asp Glu Lys Ile Asn Leu Val Ser
            20                  25                  30

Asn His Gln Phe Glu Phe Glu Leu Ile Glu Lys Asn Leu Ser Ser Lys
        35                  40                  45

Val Val Asn Phe Tyr His Leu Trp Phe Thr Ala Ile Asp Gly Ala Lys
    50                  55                  60

Ile His Ala Gln Leu Ile Val Pro Lys Asn Leu Lys Glu Lys Tyr Pro
65                  70                  75                  80

Ala Ile Leu Gln Phe His Gly Tyr His Cys Asp Ser Gly Asp Trp Val
                85                  90                  95

Asp Lys Ile Gly Ile Val Ala Glu Gly Asn Val Val Leu Ala Leu Asp
            100                 105                 110

Cys Arg Gly Gln Gly Gly Leu Ser Gln Asp Asn Ile Gln Thr Met Gly
        115                 120                 125

Met Thr Met Lys Gly Leu Ile Val Arg Gly Ile Asp Glu Gly Tyr Glu
    130                 135                 140

Asn Leu Tyr Tyr Val Arg Gln Phe Met Asp Leu Ile Thr Ala Thr Lys
145                 150                 155                 160

Ile Leu Ser Glu Phe Asp Phe Val Asp Glu Thr Asn Ile Ser Ala Gln
                165                 170                 175

Gly Ala Ser Gln Gly Gly Ala Leu Ala Val Ala Cys Ala Ala Leu Ser
```

```
                180             185             190
Pro Leu Ile Lys Lys Val Thr Ala Thr Tyr Pro Phe Leu Ser Asp Tyr
            195             200             205

Arg Lys Ala Tyr Glu Leu Gly Ala Glu Glu Ser Ala Phe Glu Glu Leu
            210             215             220

Pro Tyr Trp Phe Gln Phe Lys Asp Pro Leu His Leu Arg Glu Asp Trp
225             230             235             240

Phe Phe Asn Gln Leu Glu Tyr Ile Asp Ile Gln Asn Leu Ala Pro Arg
            245             250             255

Ile Lys Ala Glu Val Ile Trp Ile Leu Gly Gly Lys Asp Thr Val Val
            260             265             270

Pro Pro Ile Thr Gln Met Ala Ala Tyr Asn Lys Ile Gln Ser Lys Lys
            275             280             285

Ser Leu Tyr Val Leu Pro Glu Tyr Gly His Glu Tyr Leu Pro Lys Ile
            290             295             300

Ser Asp Trp Leu Arg Glu Asn Gln Gly Pro Gly Ser Gly Gly Ala Gly
305             310             315             320

Ser Pro Gly Ser Ala Gly Gly Pro Gly Ser Asp Pro Thr Lys Pro Pro
            325             330             335

Arg Thr Pro Thr Ala Asn Thr Ser Arg Pro His His Asn Phe Gly Ser
            340             345             350

Gly Gly Gly Gly Ser Pro His His His His His His
            355             360
```

PERACID-GENERATING COMPOSITIONS

CROSS-REFERENCE TO RELATED APPLICATIONS

This application is a U.S. National Stage Application under 35 U.S.C. 371 of International Application PCT/US2012/070371, filed Dec. 18, 2012, which claims priority to U.S. Provisional Application No. 61/577,499, filed on 19 Dec. 2011, which is hereby incorporated by reference in its entirety.

BACKGROUND

There exists a need for whitening strips suitable for home use, having reduced total levels of peroxide, yet providing enhanced whitening activity.

SUMMARY

The invention provides whitening strips comprising a granular bleaching ingredient in combination with an enzyme having perhydrolytic activity ("perhydrolase") which comprises the conserved structural motif of the carbohydrate esterase family 7 and an acyl donor, such that upon use, the peroxide released by the granular bleaching ingredient reacts with the acyl donor in the presence of the perhydrolase to form a peracid, in direct proximity to the teeth, without substantial dilution from formulation excipients, thereby permitting enhanced bleaching of the teeth with much lower total amounts of peroxide.

The strips comprise an adhesive film, either single layer or multiple layers (e.g., two layers), which when hydrated with water or saliva becomes sufficiently adhesive to stick to teeth. Granular bleaching ingredient is attached to the side of the film to be placed in contact with the teeth. Upon application, the bleaching ingredient is placed directly on the teeth (that is, between the teeth and the adhesive layer). The granules then release peroxide by rapidly dissolving in water. The bleaching ingredient can be optionally coated by a quickly dissolving material, such as sodium sulfate, cornstarch or gum Arabic. Optionally, the strips provide a second layer in the film is present to prolong the exposure time. This second layer can be insoluble in water, which would require the user to remove the strip after treatment, or erodible in water, which would cause the strip to dissolve after sufficient treatment. The strip further comprises a perhydrolase (an enzyme capable of catalyzing the reaction of carboxylic acid ester and hydrogen peroxide to form a peracid), which may also be provided in granular form on the surface of the film, and an acyl donor, e.g., selected from carboxylic acids and acyl compounds, for example, triacetin or sorbitol hexaacetate, wherein the acyl donor reacts with the peroxide source in the strip in the presence of the perhydrolase to form a peracid, which enhances the bleaching action of the strip.

Some embodiments of the present invention provide a tooth whitening strip comprising a hydratable adhesive film with a first side and a second side, the first side having a granular bleaching ingredient attached thereto, wherein the tooth whitening strip further comprises, in or on the film or in the form of granules attached to the first side of the film;

a) an enzyme having perhydrolytic activity, said enzyme having a carbohydrate esterase family 7 (CE-7) signature motif that aligns with a reference sequence SEQ ID NO: 1, said signature motif comprising:
i) an RGQ motif at positions corresponding to positions 118-120 of SEQ ID NO: 1;
ii) a GXSQG motif at positions corresponding to positions 186-190 of SEQ ID NO:1; and
iii) an HE motif at positions corresponding to positions 303-304 of SEQ ID NO:1; and (b) at least one acyl donor substrate, said substrate selected from the group consisting of:
i) esters having the structure

wherein X=an ester group of the formula $R_6C(O)O$
$R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
$R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;
M is an integer ranging from 1 to the number of carbon atoms in $R_5$; and
wherein said esters have solubility in water of at least 5 ppm at 25° C.;
ii) glycerides having the structure

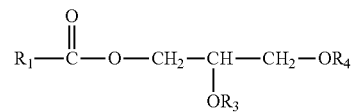

wherein $R_1$=C1 to C7 straight chain or branched chain alkyl optionally substituted with an hydroxyl or a C1 to C4 alkoxy group and $R_3$ and $R_4$ are individually H or $R_1C(O)$;
iii) one or more esters of the formula

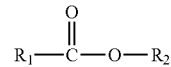

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10; and
iv) acetylated saccharides selected from the group consisting of acetylated monosaccharides, acetylated disaccharides, and acetylated polysaccharide; wherein upon hydration of the hydratable adhesive film hydrogen peroxide is released from the granular bleaching ingredient and said enzyme catalyzes the formation of an effective amount of a peracid.

Other embodiments provide of the present invention provide a method of whitening teeth comprising providing a packaging system comprising the tooth whitening strip according to any foregoing claim; removing the tooth whitening strip form the packaging system; and contacting the tooth whitening strip directly to the teeth for a period of time sufficient time whiten the teeth; wherein the tooth whitening strip is hydrated by moisture present in the oral cavity or on the tooth surface or is hydrated after step (b) but prior to step (c).

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE BIOLOGICAL SEQUENCES

The following sequences comply with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO: 1 is the amino acid sequence of *Thermotoga maritima* C277S variant perhydrolase.

SEQ ID NO: 2 is the amino acid sequence of fusion protein comprising the *Thermotoga maritima* C277S variant perhydrolase coupled to a tooth binding domain (also known as "EZ-7" in International Patent Application Publication No. WO2012/087970A2 to Butterick et al.).

SEQ ID NO: 3 is the nucleic acid sequence encoding a cephalosporin C deacetylase from *Bacillus subtilis* ATCC® 31954™.

SEQ ID NO: 4 is the amino acid sequence of a cephalosporin C deacetylase from *Bacillus subtilis* ATCC® 31954™.

SEQ ID NO: 5 is the amino acid sequence of a cephalosporin C deacetylase from *Bacillus subtilis* subsp. *subtilis* strain 168.

SEQ ID NO: 6 is the amino acid sequence of a cephalosporin C deacetylase from *B. subtilis* ATCC® 6633™.

SEQ ID NO: 7 is the amino acid sequence of a cephalosporin C deacetylase from *B. licheniformis* ATCC® 14580™.

SEQ ID NO: 8 is the amino acid sequence of an acetyl xylan esterase from *B. pumilus* PS213.

SEQ ID NO: 9 is the amino acid sequence of an acetyl xylan esterase from *Clostridium thermocellum* ATCC® 27405™.

SEQ ID NO: 10 is the amino acid sequence of an acetyl xylan esterase from *Thermotoga neapolitana*.

SEQ ID NO: 11 is the amino acid sequence of an acetyl xylan esterase from *Thermotoga maritima* MSB8.

SEQ ID NO: 12 is the amino acid sequence of an acetyl xylan esterase from *Thermoanaerobacterium* sp. JW/SL YS485.

SEQ ID NO: 13 is the amino acid sequence of a cephalosporin C deacetylase from *Bacillus halodurans* C-125.

SEQ ID NO: 14 is the amino acid sequence of a cephalosporin C deacetylase from *Bacillus clausii* KSM-K16.

SEQ ID NO: 15 is the amino acid sequence of a *Thermotoga neapolitana* acetyl xylan esterase variant from U.S. Patent Application Publication No. 2010-0087529 (incorporated herein by reference in its entirety), where the Xaa residue at position 277 is Ala, Val, Ser, or Thr.

SEQ ID NO: 16 is the amino acid sequence of a *Thermotoga maritima* MSB8 acetyl xylan esterase variant from U.S. Patent Application Publication No. 2010-0087529, where the Xaa residue at position 277 is Ala, Val, Ser, or Thr.

SEQ ID NO: 17 is the deduced amino acid sequence of a *Thermotoga lettingae* acetyl xylan esterase variant from U.S. Patent Application Publication No. 2010-0087529, where the Xaa residue at position 277 is Ala, Val, Ser, or Thr.

SEQ ID NO: 18 is the amino acid sequence of a *Thermotoga petrophila* acetyl xylan esterase variant from U.S. Patent Application Publication No. 2010-0087529, where the Xaa residue at position 277 is Ala, Val, Ser, or Thr.

SEQ ID NO: 19 is the amino acid sequence of a *Thermotoga* sp. RQ2 acetyl xylan esterase variant derived from "RQ2(a)" from U.S. Patent Application Publication No. 2010-0087529, where the Xaa residue at position 277 is Ala, Val, Ser, or Thr.

SEQ ID NO: 20 is the amino acid sequence of a *Thermotoga* sp. RQ2 acetyl xylan esterase variant derived from "RQ2(b)" from U.S. Patent Application Publication No. 2010-0087529, where the Xaa residue at position 278 is Ala, Val, Ser, or Thr.

SEQ ID NO: 21 is the amino acid sequence of a *Thermotoga lettingae* acetyl xylan esterase.

SEQ ID NO: 22 is the amino acid sequence of a *Thermotoga petrophila* acetyl xylan esterase.

SEQ ID NO: 23 is the amino acid sequence of a first acetyl xylan esterase from *Thermotoga* sp. RQ2 described as "RQ2(a)".

SEQ ID NO: 24 is the amino acid sequence of a second acetyl xylan esterase from *Thermotoga* sp. RQ2 described as "RQ2(b)".

SEQ ID NO: 25 is the amino acid sequence of a *Thermoanaerobacterium saccharolyticum* cephalosporin C deacetylase.

SEQ ID NO: 26 is the amino acid sequence of the acetyl xylan esterase from *Lactococcus lactis* (GENBANK® accession number ABX75634.1).

SEQ ID NO: 27 is the amino acid sequence of the acetyl xylan esterase from *Mesorhizobium loti* (GENBANK® accession number BAB53179.1).

SEQ ID NO: 28 is the amino acid sequence of the acetyl xylan esterase from *Geobacillus stearothermophilus* (GENBANK® accession number AAF70202.1).

SEQ ID NOs 29-163 are the amino acid sequences of peptides having affinity to an oral cavity surface.

SEQ ID NOs: 164-177 are the amino acid sequences of peptide linkers/spacers. SEQ ID NOs: 178-197 are the amino acid sequences of various targeted perhydrolase fusion constructs comprising a perhydrolytic enzyme couple via a peptide linker to a binding domain having affinity for an oral surface (see International Patent Application Publication No. WO2012/087970A2 to Butterick et al.).

DETAILED DESCRIPTION

The following description of the preferred embodiment(s) is merely exemplary in nature and is in no way intended to limit the invention, its application, or uses.

As used herein, the articles "a", "an", and "the" preceding an element or component of the invention are intended to be nonrestrictive regarding the number of instances (i.e., occurrences) of the element or component. Therefore "a", "an", and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the terms "substrate", "suitable substrate", "acyl donor", and "carboxylic acid ester substrate" interchangeably refer specifically to:

(a) one or more esters having the structure $[X]_m R_5$ wherein

X is an ester group of the formula $R_6C(O)O$;

$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety or a cyclic five-membered heteroaromatic or six-membered cyclic aromatic or heteroaromatic moiety optionally substituted with a hydroxyl group; wherein each carbon atom in $R_5$ individually comprises no more than one hydroxyl group or no more than one ester group, and wherein $R_5$ optionally comprises one or more ether linkages;

m is an integer ranging from 1 to the number of carbon atoms in $R_5$, said one or more esters having solubility in water of at least 5 ppm at 25° C.; or (b) one or more glycerides having the structure

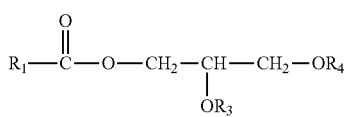

wherein $R_1$ is a C1 to C7 straight chain or branched chain alkyl optionally substituted with an hydroxyl or a C1 to C4 alkoxy group and $R_3$ and $R_4$ are individually H or $R_1C(O)$; or (c) one or more esters of the formula

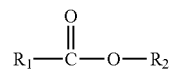

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10; or (d) one or more acetylated monosaccharides, acetylated disaccharides, or acetylated polysaccharides; or (e) any combination of (a) through (d).

As used herein, the term "peracid" is synonymous with peroxyacid, peroxycarboxylic acid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate, 1,2,3-triacetoxypropane; 1,2,3-propanetriol triacetate and all other synonyms of CAS Registry Number 102-76-1.

As used herein, the terms "acetylated sugar" and "acetylated saccharide" refer to mono-, di- and polysaccharides comprising at least one acetyl group. Examples include, but are not limited to glucose pentaacetate; xylose tetraacetate; acetylated xylan; acetylated xylan fragments; β-D-ribofuranose-1,2,3,5-tetraacetate; tri-O-acetyl-D-galactal; and tri-O-acetyl-glucal.

As used herein, the terms "hydrocarbyl", "hydrocarbyl group", and "hydrocarbyl moiety" is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In a preferred embodiment, the hydrocarbyl moiety is a straight chain, branched or cyclic arrangement of carbon atoms connected by single carbon to carbon bonds and/or by ether linkages, and substituted accordingly with hydrogen atoms.

As used herein, the terms "monoesters" and "diesters" of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,5-pentanediol; 1,6-pentanediol; 1,2-hexanediol; 2,5-hexanediol; 1,6-hexanediol; and mixtures thereof, refer to said compounds comprising at least one ester group of the formula RC(O)O, wherein R is a C1 to C7 linear hydrocarbyl moiety. In one embodiment, the carboxylic acid ester substrate is selected from the group consisting of propylene glycol diacetate (PGDA), ethylene glycol diacetate (EDGA), and mixtures thereof.

As used herein, the term "propylene glycol diacetate" is synonymous with 1,2-diacetoxypropane, propylene diacetate, 1,2-propanediol diacetate, and all other synonyms of CAS Registry Number 623-84-7.

As used herein, the term "ethylene glycol diacetate" is synonymous with 1,2-diacetoxyethane, ethylene diacetate, glycol diacetate, and all other synonyms of CAS Registry Number 111-55-7.

As used herein, the terms "suitable enzymatic reaction mixture", "components suitable for in situ generation of a peracid", "suitable reaction components", "suitable aqueous reaction mixture", "reaction mixture", and "peracid-generating components" refer to the materials and water (from saliva and/or applied by the user to the hydratable adhesive film prior to use) in which the reactants and the perhydrolytic enzyme catalyst come into contact. The peracid-generating components will include at least enzyme having perhydrolytic activity, preferably wherein the perhydrolytic enzyme is at least one CE-7 perhydrolase (optionally in the form of a fusion protein targeted to a body surface), at least one suitable carboxylic acid ester substrate, a source of peroxygen, and water (from saliva and/or applied by the user to the hydratable adhesive film prior to use).

As used herein, the term "perhydrolysis" is defined as the reaction of a selected substrate with peroxide to form a peracid. Typically, inorganic peroxide is reacted with the selected substrate in the presence of a catalyst to produce the peroxycarboxylic acid. As used herein, the term "chemical perhydrolysis" includes perhydrolysis reactions in which a substrate (a peroxycarboxylic acid precursor) is combined with a source of hydrogen peroxide wherein peroxycarboxylic acid is formed in the absence of an enzyme catalyst. As used herein, the term "enzymatic perhydrolysis" includes perhydrolysis reactions in which a carboxylic acid ester substrate (a peracid precursor; the "acyl donor") is combined with a source of hydrogen peroxide and water whereby the enzyme catalyst catalyzes the formation of peracid.

As used herein, the term "perhydrolase activity" refers to the catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 μmol of peroxycarboxylic acid product per minute at a specified temperature.

As used herein, the terms "enzyme catalyst" and "perhydrolase catalyst" refer to a catalyst comprising an enzyme having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (such as by pegylation or by reaction with cross-linking reagents). The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. In one embodiment, the perhydrolase catalyst may be immobilized non-covalently in or on an oral care strip (e.g., a whitening strip) or dental tray. In a further embodiment, the non-covalent immobilization to the strip or dental tray may be through the use of a peptidic binding domain having strong affinity for a material in or on the strip or tray (e.g., a fusion protein comprising a perhydrolytic enzyme coupled through an optional peptide spacer to a peptidic binding domain). In another embodiment, the dental tray is deformable tray. In yet a further embodiment, the perhydrolase catalyst is immobilized in or on the deformable tray after the formation of the dental impression.

As used herein, "acetyl xylan esterases" refers to an enzyme (E.C. 3.1.1.72; AXEs) that catalyzes the deacetylation of acetylated xylans and other acetylated saccharides.

As used herein, the terms "cephalosporin C deacetylase" and "cephalosporin C acetyl hydrolase" refer to an enzyme (E.C. 3.1.1.41) that catalyzes the deacetylation of cephalosporins such as cephalosporin C and 7-aminocephalosporanic acid (Mitsushima et al., (1995) *Appl. Env. Microbiol.* 61(6):2224-2229). The amino acid sequences of several cephalosporin C deacetylases having significant perhydrolytic activity are provided herein.

As used herein, the term "*Bacillus subtilis* ATCC® 31954™" refers to a bacterial cell deposited to the American Type Culture Collection (ATCC) having international depository accession number ATCC® 31954™. As described herein, an enzyme having significant perhydrolase activity from *B. subtilis* ATCC® 31954™ is provided as SEQ ID NO: 4 (see United States Patent Application Publication No. 2010-0041752).

As used herein, the term "*Thermotoga maritima* MSB8" refers to a bacterial cell reported to have acetyl xylan esterase activity (GENBANK® NP_227893.1; see U.S. Patent Application Publication No. 2008-0176299). The amino acid sequence of the enzyme having perhydrolase activity from *Thermotoga maritima* MSB8 is provided as SEQ ID NO: 11. Variants of the *Thermotoga maritima* MSB8 perhydrolase are provided as SEQ ID NOs: 1 and 16.

As used herein, an "isolated nucleic acid molecule", "isolated polynucleotide", and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

As used herein, the term "about" modifying the quantity of an ingredient or reactant employed refers to variation in the numerical quantity that can occur, for example, through typical measuring and liquid handling procedures used for making concentrates or As used herein, the terms "signature motif" and "diagnostic motif" refer to conserved structures shared among a family of enzymes having a defined activity. The signature motif can be used to define and/or identify the family of structurally-related enzymes having similar enzymatic activity for a defined family of substrates. The signature motif can be a single contiguous amino acid sequence or a collection of discontiguous, conserved motifs that together form the signature motif. Typically, the conserved motif(s) is represented by an amino acid sequence. In one embodiment, the perhydrolytic enzymes used in the present compositions and methods comprise a CE-7 carbohydrate esterase signature motif.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Accelrys Software Corp., San Diego, Calif.), BLASTP, BLASTN, BLASTX (Altschul et al., *J. Mol. Biol.* 215:403-410 (1990)), and DNASTAR (DNASTAR, Inc. 1228 S. Park St. Madison, Wis. 53715 USA), CLUSTALW (for example, version 1.83; Thompson et al., *Nucleic Acids Research*, 22(22):4673-4680 (1994)), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

The term "body surface" refers to any surface of the human body that may serve as the target for a benefit agent, such as a peracid benefit agent. The present methods and compositions are directed to oral care applications and products. As such, the body surface comprises an oral cavity material/surface. In one embodiment, the oral cavity material comprises tooth enamel.

As used herein, the terms "tooth whitening" and "tooth bleaching" are used interchangeably, to refer to improving the brightness (e.g., whitening) of a tooth or teeth. Whitening strips are described herein comprising ingredients suitable to enzymatically generate an efficacious amount of a peracid to whiten teeth when hydrated.

As used in herein, "intrinsic stains" in teeth refer to the resulting color from chromogens within the enamel and underlying dentin. The intrinsic color of human teeth tends to become more yellow with aging, due to the thinning of the enamel and darkening of the underlying yellow dentin. Removal of intrinsic stain usually requires the use of peroxides or other oxidizing chemicals, which penetrate the enamel and decolorize the internal chromogens.

In contrast to intrinsic stains, "extrinsic stains" form on the surface of the teeth when exogenous chromogenic materials bind to the enamel, usually within the pellicle naturally coating the teeth. Most people accumulate some degree of unsightly extrinsic stains on their teeth over time. This staining process is promoted by such factors as: (1) the ingestion of tannin-containing foods and beverages such as coffee, tea, or red wine; (2) the use of tobacco products; and/or (3) exposure to certain cationic substances (e.g., tin, iron, and chlorhexidine). These substances tend to adhere to the enamel's hydroxyapatite structure, which leads to tooth discoloration and a concomitant reduction in tooth whiteness. Over a period of years, extrinsic stains may penetrate the enamel layer and result in intrinsic stains.

As used herein, the term "destain" or "destaining" refers to the process of removing a stain from an oral cavity surface. The stain(s) may be intrinsic stains, extrinsic stains, or a combination thereof.

As used herein, "effective amount of perhydrolase enzyme" refers to the quantity of perhydrolase enzyme necessary to achieve the enzymatic activity required in the specific application. Such effective amounts are readily ascertained by one of ordinary skill in the art and are based on many factors, such as the particular enzyme variant used.

As used herein, the terms "peroxygen source" and "source of peroxygen" refer to compounds capable of providing hydrogen peroxide at a concentration of about 1 mM or more when in an aqueous solution including, but not limited to, hydrogen peroxide, hydrogen peroxide adducts (e.g., urea-hydrogen peroxide adduct (carbamide peroxide)), perborates, and percarbonates. As described herein, the peroxygen source in the present whitening strips is in the form of granular particles, wherein the user hydrates the granular peroxide particles to release an effective amount of hydrogen peroxide. As described herein, the concentration of the hydrogen peroxide provided by the peroxygen compound in the aqueous reaction formulation is initially at least 0.1 mM or more upon combining the reaction components. In one embodiment, the hydrogen peroxide concentration in the aqueous reaction formulation is at least 0.5 mM. In one embodiment, the hydrogen peroxide concentration in the aqueous reaction formulation is at least 1 mM. In another embodiment, the hydrogen peroxide concentration in the aqueous reaction formulation is at least 10 mM. In another embodiment, the hydrogen peroxide concentration in the aqueous reaction formulation is at least 100 mM. In another embodiment, the hydrogen peroxide concentration in the aqueous reaction formulation is at least 200 mM. In another embodiment, the hydrogen peroxide concentration in the aqueous reaction formulation is 500 mM or more. In yet another embodiment, the hydrogen peroxide concentration in the aqueous reaction formulation is 1000 mM or more. The molar ratio of the hydrogen peroxide to enzyme substrate, e.g., triglyceride, ($H_2O_2$:substrate) in the formulation may be from about 0.002 to 20, preferably about 0.1 to 10, and most preferably about 0.5 to 5.

As used herein, the term "oligosaccharide" refers to compounds containing between 2 and at least 24 monosaccharide units linked by glycosidic linkages. The term "monosaccharide" refers to a compound of empirical formula $(CH_2O)_n$, where n≥3, the carbon skeleton is unbranched, each carbon atom except one contains a hydroxyl group, and the remaining carbon atom is an aldehyde or ketone at carbon atom 1. The term "monosaccharide" also refers to intracellular cyclic hemiacetal or hemiketal forms.

As used herein, the term "hydratable adhesive" will refer to an adhesive material capable of being hydrated. The hydratable adhesive is substantially dry and non-adhesive until hydrated. Upon hydration, the hydratable adhesive becomes sufficiently adhesive to bind the tooth whitening strip/film to the surface of a tooth. The hydratable adhesive film also comprises a granular bleaching ingredient whereby upon hydration and effective amount of hydrogen peroxide is released to be used in the enzymatic formation of a peracid bleaching agent. The whitening strip/film is typically thin (typically less than 2 mm), shaped and sized to fit within the oral cavity, and sufficiently flexible such that the film and be applied and placed in contact with a plurality of teeth whereby the hydrated adhesive helps to hold the film/strip on the tooth surface and provide a sufficient amount of time for the peracid bleaching agent to whiten the teeth.

As used herein, the term "effective amount" will refer to the amount of material necessary to achieve the desired effect.

As used herein, the term "substantially non-adhesive until hydrated" will refer to the lack of adhesive strength sufficient to adhere the tooth whitening film to the surface of a plurality of teeth prior to hydration. As such, the hydratable adhesive film will be easy to handle and manipulate prior to application/hydration by the user.

By "sequence identity" is meant amino acid identity using a sequence alignment program, e.g., ClustalW or BLAST, e.g., generally as described in Altschul S F, Gish W, Miller W, Myers E W, Lipman D J, "Basic local alignment search tool", J Mol Biol (1990) 215 (3): 403-410, and Goujon M, McWilliam H, Li W, Valentin F, Squizzato S, Paern J, Lopez R, Nucleic Acids Research (2010) 38 Suppl: W695-9.

Acyl donors for use in the present invention, for example, to form peracids upon reaction with peroxide, are selected from one or more of (i) $C_{2-18}$ carboxylic acids, e.g $C_{2-6}$ carboxylic acids (e.g., acetic acid), including lower linear or branched alkyl carboxylic acids, optionally substituted with hydroxy and/or $C_{1-4}$ alkoxy; (ii) hydrolysable and acceptable esters thereof (e.g. mono-, di-, and tri-glycerides and acylated saccharides) and (iii) mixtures thereof. For example, acyl donors include 1,2,3-triacetoxypropane (sometimes referred to herein as triacetin or glycerin triacetate) and acylated saccharides, e.g. acetylated saccharides. In a particular embodiment, esters for this use may, for example, be esters having solubility in water of at least 5 ppm at 25° C.

The acyl donors and/or enzymes may optionally be encapsulated. There are a variety of encapsulation options well-known to the art, both natural and synthetic. Modified starches and gum Arabic are particularly well-suited since they are food grade, relatively inexpensive, quick to dissolve, and can adsorb fairly high levels of liquid oils. Any impact on the final viscosity needs to be considered.

In some embodiments, the granules comprise an antisensitivity agent capable of desensitizing the nerves or occluding dentine tubules. In some embodiments, the antisensitivity agent is selected from a potassium ion source, a silicate, a stannous ion source, a basic amino acid, a clay, and a combination thereof. In some embodiments, the potassium ion source is an orally-acceptable potassium salt and is present in an amount effective to reduce dentinal sensitivity. In some embodiments, the potassium ion source is selected from potassium chloride, potassium nitrate and a combination thereof. In some embodiments, the basic amino acid is arginine. In some embodiments, the basic amino acid is selected from arginine phosphate, arginine bicarbonate, and arginine hydrochloride. In some embodiments, the silicate is calcium silicate.

CE-7 Perhydrolases

The present compositions and method comprise enzymes having perhydrolytic activity that are structurally classified as members of the carbohydrate family esterase family 7 (CE-7 family) of enzymes (see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12.). The CE-7 family of enzymes has been demonstrated to be particularly effective for producing peroxycarboxylic acids from a variety of carboxylic acid ester substrates when combined with a source of peroxygen (U.S. Pat. Nos. 7,794,378; 7,951,566; 7,723,083; and 7,964,378 and U.S. Patent Application Publication Nos. 2008-0176299, 2010-0087529, 2011-0081693, and 2011-0236335 to DiCosimo et al.; each incorporated herein by reference).

Members of the CE-7 family include cephalosporin C deacetylases (CAHs; E.C. 3.1.1.41) and acetyl xylan esterases (AXEs; E.C. 3.1.1.72). Members of the CE-7 esterase family share a conserved signature motif (Vincent et al., *J. Mol. Biol.*, 330:593-606 (2003)). Perhydrolases comprising the CE-7 signature motif ("CE-7 perhydrolases") and/or a substantially similar structure are suitable for use in the compositions and methods described herein. Means to identify substantially similar biological molecules are well known in the art (e.g., sequence alignment protocols, nucleic acid hybridizations and/or the presence of a conserved signature motif). In one aspect, the perhydrolase includes an enzyme comprising the CE-7 signature motif and at least 20%, preferably at least 30%, more preferably at least 33%, more preferably at least 40%, more preferably at least 42%, more preferably at least 50%, more preferably at least 60%, more preferably at least 70%, more preferably at least 80%, more preferably at least 90%, and most preferably at least 90%, 91%, 92%, 93%, 94%, 95%, 96%, 97%, 98%, or 99% amino acid identity to one of the sequences provided herein.

As used herein, the phrase "enzyme is structurally classified as a CE-7 enzyme", "CE-7 perhydrolase" or "structurally classified as a carbohydrate esterase family 7 enzyme" will be used to refer to enzymes having perhydrolytic activity which are structurally classified as a CE-7 carbohydrate esterase. This family of enzymes can be defined by the presence of a signature motif (Vincent et al., supra). The signature motif for CE-7 esterases comprises three conserved motifs (residue position numbering relative to reference sequence SEQ ID NO: 1; a C277S variant of the *Thermotoga maritima* perhydrolase).

Arg118-Gly119-Gln120;
Gly186-Xaa187-Ser188-Gln189-Gly190; and
His303-Glu304.

Typically, the Xaa at amino acid residue position 187 is glycine, alanine, proline, tryptophan, or threonine. Two of the three amino acid residues belonging to the catalytic triad are in bold. In one embodiment, the Xaa at amino acid residue position 187 is selected from the group consisting of glycine, alanine, proline, tryptophan, and threonine.

Further analysis of the conserved motifs within the CE-7 carbohydrate esterase family indicates the presence of an additional conserved motif (LXD at amino acid positions 272-274 of SEQ ID NO: 1) that may be used to further define a perhydrolase belonging to the CE-7 carbohydrate esterase family. In a further embodiment, the signature motif defined above may include an additional (fourth) conserved motif defined as:

Leu272-Xaa273-Asp274.

The Xaa at amino acid residue position 273 is typically isoleucine, valine, or methionine. The fourth motif includes the aspartic acid residue (bold) belonging to the catalytic triad (Ser188-Asp274-His303).

The CE-7 perhydrolases may be in the form of fusion proteins having at least one peptidic component having affinity for at least one body surface. In one embodiment, all alignments used to determine if a targeted perhydrolase (fusion protein) comprises the CE-7 signature motif will be based on the amino acid sequence of the perhydrolytic enzyme without the peptidic component having the affinity for a body surface.

A number of well-known global alignment algorithms (i.e., sequence analysis software) may be used to align two or more amino acid sequences representing enzymes having perhydrolase activity to determine if the enzyme is comprised of the present signature motif. The aligned sequence(s) are compared to the reference sequence (SEQ ID NO: 1) to determine the existence of the signature motif. In one embodiment, a CLUSTAL alignment (such as CLUSTALW) using a reference amino acid sequence (as used herein the perhydrolase sequence (SEQ ID NO: 1)) is used to identify perhydrolases belonging to the CE-7 esterase family. The relative numbering of the conserved amino acid residues is based on the residue numbering of the reference amino acid sequence to account for small insertions or deletions (for example, typically five amino acids of less) within the aligned sequence.

Examples of other suitable algorithms that may be used to identify sequences comprising the present signature motif (when compared to the reference sequence) include, but are not limited to, Needleman and Wunsch (*J. Mol. Biol.* 48, 443-453 (1970); a global alignment tool) and Smith-Waterman (*J. Mol. Biol.* 147:195-197 (1981); a local alignment tool). In one embodiment, a Smith-Waterman alignment is implemented using default parameters. An example of suitable default parameters include the use of a BLOSUM62 scoring matrix with GAP open penalty=10 and a GAP extension penalty=0.5.

In one embodiment, suitable perhydrolases include enzymes comprising the CE-7 signature motif and at least 20%, preferably at least 30%, 33%, 40%, 50%, 60%, 70%, 80%, 85%, 90%, 91%, 92%, 93%, 94%, 95%, 96%, 97%, 98%, or 99% amino acid identity to SEQ ID NO: 1.

Examples of suitable CE-7 carbohydrate esterases having perhydrolytic activity include, but are not limited to, enzymes having an amino acid sequence such as SEQ ID NOs: 1, and 4-28. In one embodiment, the enzyme comprises an amino acid sequence selected from the group consisting of 1, 10, 11, 15, and 16.

As used herein, the term "CE-7 variant", "variant perhydrolase" or "variant" will refer to CE-7 perhydrolases having a genetic modification that results in at least one amino acid addition, deletion, and/or substitution when compared to the corresponding enzyme (typically the wild type enzyme) from which the variant was derived; so long as the CE-7 signature motif and the associated perhydrolytic activity are maintained. CE-7 variant perhydrolases may also be used in the present compositions and methods. Examples of CE-7 variants are provided as SEQ ID NOs: 1, 15, 16, 17, 18, 19, and 20. In one embodiment, the variants may include SEQ ID NOs: 1 and 16.

The skilled artisan recognizes that substantially similar CE-7 perhydrolase sequences (retaining the signature motifs) may also be used in the present compositions and methods. In one embodiment, substantially similar sequences are defined by their ability to hybridize, under highly stringent conditions with the nucleic acid molecules associated with sequences exemplified herein. In another embodiment, sequence alignment algorithms may be used to define substantially similar enzymes based on the percent identity to the DNA or amino acid sequences provided herein.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of highly stringent hybridization conditions is 0.1×SSC, 0.1% SDS, 65° C. and washed with 2×SSC, 0.1% SDS followed by a final wash of 0.1×SSC, 0.1% SDS, 65° C.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook and Russell, supra). For hybridizations with shorter nucleic acids, i.e., oligonucleotides, the position of mismatches becomes more important, and the length of the oligonucleotide determines its specificity (Sambrook and Russell, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6):276-277 (2000)). Multiple alignment of the sequences can be performed using the CLUSTAL method (such as CLUSTALW; for example version 1.83) of alignment (Higgins and Sharp, *CABIOS*, 5:151-153 (1989); Higgins et al., *Nucleic Acids Res.* 22:4673-4680 (1994); and Chenna et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g., Gonnet250), protein ENDGAP=−1, protein GAPDIST=4, and KTUPLE=1. In one embodiment, a fast or slow alignment is used with the default settings where a slow alignment is preferred. Alternatively, the parameters using the CLUSTALW method (e.g., version 1.83) may be modified to also use KTUPLE=1, GAP PENALTY=10, GAP extension=1, matrix=BLOSUM (e.g., BLOSUM64), WINDOW=5, and TOP DIAGONALS SAVED=5.

In one aspect, suitable isolated nucleic acid molecules encode a polypeptide having an amino acid sequence that is at least about 20%, preferably at least 30%, 33%, 40%, 50%, 60%, 70%, 80%, 85%, 90%, 91%, 92%, 93%, 94%, 95%, 96%, 97%, 98%, or 99% identical to the amino acid sequences reported herein. In another aspect, suitable isolated nucleic acid molecules encode a polypeptide having an amino acid sequence that is at least about 20%, preferably at least 30%, 33%, 40%, 50%, 60%, 70%, 80%, 85%, 90%, 91%, 92%, 93%, 94%, 95%, 96%, 97%, 98%, or 99% identical to the amino acid sequences reported herein. Suitable nucleic acid molecules not only have the above homologies, but also typically encode a polypeptide having about 210 to 340 amino acids in length, about 300 to about 340 amino acids, preferably about 310 to about 330 amino acids, and most preferably about 318 to about 325 amino acids in length wherein each polypeptide is characterized as having perhydrolytic activity.

Targeted Perhydrolases

As used herein, the term "targeted perhydrolase" and "targeted enzyme having perhydrolytic activity" will refer to a fusion proteins comprising at least one perhydrolytic enzyme (wild type or variant thereof) fused/coupled to at least one peptidic component having affinity for a target surface, preferably a targeted body surface. The perhydrolytic enzyme within the targeted perhydrolase may be any CE-7 carbohydrate esterase having perhydrolytic activity. The CE-7 perhydrolase may be identified by the presence of the CE-7 signature motif that aligns with a reference sequence SEQ ID NO: 1, said signature motif comprising:
  i) an RGQ motif at positions corresponding to positions 118-120 of SEQ ID NO: 1;
  ii) a GXSQG motif at positions corresponding to positions 186-190 of SEQ ID NO:1; and
  iii) an HE motif at positions corresponding to positions 303-304 of SEQ ID NO:1; and In one embodiment, perhydrolytic enzymes may be those having an amino acid sequence that is at least about 20%, preferably at least 30%, 33%, 40%, 50%, 60%, 70%, 80%, 85%, 90%, 91%, 92%, 93%, 94%, 95%, 96%, 97%, 98%, or 99% identical to any of the amino acid sequences reported herein (i.e., SEQ ID NOs 1, and 4-28).

In another embodiment, the fusion protein comprises a perhydrolytic enzyme having an amino acid sequence selected from the group consisting of SEQ ID NOs: 1, and 4-28.

As used herein the terms "peptidic component", "peptidic component having affinity for an oral cavity surface", "oral cavity binding domain", and "OCBD" will refer to component of the fusion protein that is not part of the perhydrolytic enzyme comprising at least one polymer of two or more amino acids joined by a peptide bond; wherein the component has affinity for the target oral cavity surface. In a preferred aspect, the OCBD has affinity for tooth enamel.

In one embodiment, the peptidic component having affinity for a body surface may be an antibody, an Fab antibody fragment, a single chain variable fragment (scFv) antibody, a Camelidae antibody (Muyldermans, S., *Rev. Mol. Biotechnol.* (2001) 74:277-302), a non-antibody scaffold display protein (Hosse et al., *Prot. Sci.* (2006) 15(1): 14-27 and Binz, H. et al. (2005) *Nature Biotechnology* 23, 1257-1268 for a review of various scaffold-assisted approaches) or a single chain polypeptide lacking an immunoglobulin fold. In another aspect, the peptidic component having affinity for the oral cavity tissue/surface (such as tooth enamel) is a single chain peptide lacking an immunoglobulin fold.

The peptidic component having affinity for an oral cavity surface may be separated from the perhydrolytic enzyme by an optional peptide linker. Certain peptide linkers/spacers are from 1 to 100 or 1 to 50 amino acids in length. In some embodiments, the peptide spacers are about 1 to about 25, 3 to about 40, or 3 to about 30 amino acids in length. In other embodiments are spacers that are about 5 to about 20 amino acids in length. Multiple peptide linkers may be used. In one embodiment, at least one peptide linker is present and may be repeated up to 10 times.

In one embodiment, the fusion peptide comprises at least one oral cavity surface-binding peptide selected from the group consisting of SEQ ID NOs: 178-197.

In another embodiment the target surface is a material that is part of the packaging, such as the whitening strip or polymeric backing layer (when using a polymeric backing layer to which the hydratable adhesive is applied) and/or method of delivery to the oral cavity. The peptidic component is selected for it affinity to a material or materials in use such as polymers, plastics and films. The targeted perhydrolase fusion protein design allows for the controlled delivery and removal of the perhydrolase from the user by maintaining it on a removable device such as, but not limited to, a mouth tray or strip.

The peptidic component having affinity for an oral cavity surface may be separated from the CE-7 perhydrolase by an optional peptide linker. Certain peptide linkers/spacers are from 1 to 100 or 1 to 50 amino acids in length. In some embodiments, the peptide spacers are about 1 to about 25, 3 to about 40, or 3 to about 30 amino acids in length. In other embodiments are spacers that are about 5 to about 20 amino acids in length. Multiple peptide linkers may be used. Examples of peptide linkers are provided as SEQ ID NOs: 164-177.

As such, examples of targeted CE-7 perhydrolases may include, but are not limited to, any of the CE-7 perhydrolases having an amino acid sequence selected from the group consisting of SEQ ID NOs 1, and 4-28 coupled to a peptidic component having affinity for an oral cavity surface. In a preferred embodiment, examples of targeted perhydrolases may include, but are not limited to, any of CE-7 perhydrolases having an amino acid sequence selected from the group consisting of SEQ ID NOs 1, 4, 5, 6, 7, 8, 9, 10, 11, 12, 13, 14, 15, 16, 17, 18, 19, 20, 21, 22, 23, 24, 25, 26, 27, and 28 coupled to one or more body surface-binding peptides having affinity for an oral cavity surface (optionally through a peptide spacer). In a preferred embodiment, the targeted perhydrolase includes a CE-7 perhydrolase having an amino acid sequence selected from the group consisting of SEQ ID NOs: 1 and 16.

In one embodiment, the perhydrolase is a CE-7 perhydrolase in the form of a fusion protein having the following general structure:

PAH-[L]y-OCBD or OCBD-[L]y-PAH wherein PAH is the enzyme having perhydrolytic activity, e.g., having a CE-7 signature motif, e.g., SEQ ID NO:1, and OCBD is a peptidic component having affinity for an oral cavity surface; and L is an optional linker; and y is an integer ranging from 0 to 10. In one embodiment, the linker (L) is present and is a peptide linker ranging from 1 to 100 amino acids in length.

For example SEQ ID NO: 2 is a fusion protein having a perhydrolase sequence of SEQ ID NO: 1 coupled to a C-terminal targeting domain with an affinity for oral tissues.

The perhydrolases for use in the products and methods of the invention may be in free, protected (e.g., acetylated), or salt form.

In another embodiment, the target surface is a material that is part of the packaging and or delivery to the oral cavity. The peptidic component is selected for it affinity to a material or materials in use such as polymers, plastics and films. The targeted CE-7 perhydrolase fusion protein design allows for the controlled delivery and removal of the perhydrolase from the user by maintaining it on a removable device such as a mouth tray or strip.

Binding Affinity

The peptidic component having affinity for the oral cavity surface comprises a binding affinity for an oral cavity surface of $10^{-5}$ molar (M) or less. In certain embodiments, the peptidic component is one or more oral cavity surface-binding peptides and/or binding domain(s) having a binding affinity of $10^{-5}$ molar (M) or less for tooth enamel. In some embodiments, the binding peptides or domains will have a binding affinity value of $10^{-5}$ M or less in the presence of at least about 50-500 mM salt. The term "binding affinity" refers to the strength of the interaction of a binding peptide with its respective substrate. Binding affinity can be defined or measured in terms of the binding peptide's dissociation constant ("$K_D$"), or "$MB_{50}$."

"$K_D$" corresponds to the concentration of peptide at which the binding site on the target is half occupied, i.e., when the concentration of target with peptide bound (bound target material) equals the concentration of target with no peptide bound. The smaller the dissociation constant, the more tightly the peptide is bound. For example, a peptide with a nanomolar (nM) dissociation constant binds more tightly than a peptide with a micromolar (µM) dissociation constant. Certain embodiments of the invention will have a $K_D$ value of $10^{-5}$ or less.

"$MB_{50}$" refers to the concentration of the binding peptide that gives a signal that is 50% of the maximum signal obtained in an ELISA-based binding assay. See, e.g., Example 3 of U.S. Patent Application Publication 2005/0022683; hereby incorporated by reference. The $MB_{50}$ provides an indication of the strength of the binding interaction or affinity of the components of the complex. The lower the value of $MB_{50}$, the stronger, i.e., "better," the interaction of the peptide with its corresponding substrate. For example, a peptide with a nanomolar (nM) $MB_{50}$ binds more tightly than a peptide with a micromolar (µM) $MB_{50}$. Certain embodiments of the invention will have a $MB_{50}$ value of $10^{-5}$ M or less.

In some embodiments, the peptidic component having affinity for an oral cavity surface may have a binding affinity, as measured by $K_D$ or $MB_{50}$ values, of less than or equal to about $10^{-5}$ M, less than or equal to about $10^{-6}$ M, less than or equal to about $10^{-7}$ M, less than or equal to about $10^{-8}$ M, less than or equal to about $10^{-9}$ M, or less than or equal to about $10^{-10}$ M.

In some embodiments, the oral cavity surface-binding peptides and/or oral cavity surface-binding domains may have a binding affinity, as measured by $K_D$ or $MB_{50}$ values, of less than or equal to about $10^{-5}$ M, less than or equal to about $10^{-6}$ M, less than or equal to about $10^{-7}$ M, less than or equal to about $10^{-8}$ M, less than or equal to about $10^{-9}$ M, or less than or equal to about $10^{-10}$ M.

As used herein, the term "strong affinity" will refer to a binding affinity having a $K_D$ or $MB_{50}$ value of less than or equal to about $10^{-5}$ M, preferably less than or equal to about $10^{-6}$ M, more preferably less than or equal to about $10^{-7}$ M, more preferably less than or equal to about $10^{-8}$ M, less than or equal to about $10^{-9}$ M, or most preferably less than or equal to about $10^{-10}$ M.

Enzyme Powders

In some embodiments, the personal care compositions may use an enzyme catalyst in form of a stabilized enzyme powder. Methods to make and stabilize formulations comprising an enzyme powder are described in U.S. Patent Application Publication Nos. 2010-0086534 and 2010-0086535.

In one embodiment, the enzyme may be in the enzyme powder in an amount in a range of from about 0.5 weight percent (wt %) to about 75 wt %, e.g., 1 wt % to about 60 wt %, based on the dry weight of the enzyme powder. A preferred weight percent range of the enzyme in the enzyme powder/spray-dried mixture is from about 10 wt % to 50 wt %, and a more preferred weight percent range of the enzyme in the enzyme powder/spray-dried mixture is from about 20 wt % to 33 wt %.

In one embodiment, the enzyme powder may further comprise an excipient. In one aspect, the excipient is provided in an amount in a range of from about 95 wt % to about 25 wt % based on the dry weight of the enzyme powder. A preferred wt % range of excipient in the enzyme powder is from about 90 wt % to 50 wt %, and a more preferred wt % range of excipient in the enzyme powder is from about 80 wt % to 67 wt %.

In one embodiment, the excipient used to prepare an enzyme powder may be an oligosaccharide excipient. In one embodiment, the oligosaccharide excipient has a number average molecular weight of at least about 1250 and a weight average molecular weight of at least about 9000. In some embodiments, the oligosaccharide excipient has a number average molecular weight of at least about 1700 and a weight average molecular weight of at least about 15000. Specific oligosaccharides may include, but are not limited to, maltodextrin, xylan, mannan, fucoidan, galactomannan, chitosan, raffinose, stachyose, pectin, insulin, levan, graminan, amylopectin, sucrose, lactulose, lactose, maltose, trehalose, cellobiose, nigerotriose, maltotriose, melezitose, maltotriulose, raffinose, kestose, and mixtures thereof. In a preferred embodiment, the oligosaccharide excipient is maltodextrin. Oligosaccharide-based excipients may also include, but are not limited to, water-soluble non-ionic cellulose ethers, such as hydroxymethyl-cellulose and hydroxypropylmethylcellulose, and mixtures thereof. In yet a further embodiment, the excipient may be selected from, but not limited to, one or more of the following compounds: trehalose, lactose, sucrose, mannitol, sorbitol, glucose, cellobiose, α-cyclodextrin, and carboxymethylcellulose.

Suitable Ester Substrates/Acyl Donors

Suitable carboxylic acid ester substrates may include esters having the following formula:

(a) one or more esters having the structure

wherein

X is an ester group of the formula $R_6C(O)O$;

$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;

$R_5$ is a C1 to C6 linear, branched, or cyclic hydrocarbyl moiety or a five-membered cyclic heteroaromatic moiety or six-membered cyclic aromatic or heteroaromatic moiety optionally substituted with a hydroxyl group; wherein each carbon atom in $R_5$ individually comprises no more than one hydroxyl group or no more than one ester group or carboxylic acid group, and wherein $R_5$ optionally comprises one or more ether linkages;

m is an integer ranging from 1 to the number of carbon atoms in $R_5$, said one or more esters having solubility in water of at least 5 ppm at 25° C.; or (b) one or more glycerides having the structure

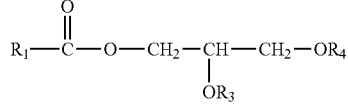

wherein $R_1$ is a C1 to C7 straight chain or branched chain alkyl optionally substituted with an hydroxyl or a C1 to C4 alkoxy group and $R_3$ and $R_4$ are individually H or $R_1C(O)$; or (c) one or more esters of the formula

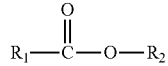

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)—O)_nH$ and n is 1 to 10; or (d) one or more acetylated monosaccharides, acetylated disaccharides, or acetylated polysaccharides; or (e) any combination of (a) through (d).

Suitable substrates may also include one or more acylated saccharides selected from the group consisting of acylated mono-, di-, and polysaccharides. In another embodiment, the acylated saccharides are selected from the group consisting of acetylated xylan; fragments of acetylated xylan; acetylated xylose (such as xylose tetraacetate); acetylated glucose (such as α-D-glucose pentaacetate; β-D-glucose pentaacetate; 1-thio-β-D-glucose-2,3,4,6-tetraacetate); β-D-galactose pentaacetate; sorbitol hexaacetate; sucrose octaacetate; β-D-ribofuranose-1,2,3,5-tetraacetate; β-D-ribofuranose-1,2,3,4-tetraacetate; tri-O-acetyl-D-galactal; tri-O-acetyl-D-glucal; β-D-xylofuranose tetraacetate, β-D-glucopyranose pentaacetate; β-D-glucopyranose-1,2,3,4-tetraacetate; β-D-glucopyranose-2,3,4,6-tetraacetate; 2-acetamido-2-deoxy-1,3,4,6-tetracetyl-β-D-glucopyranose; 2-acetamido-2-deoxy-3,4,6-triacetyl-1-chloride-α-D-glucopyranose; β-D-mannopyranose pentaacetate, and acetylated cellulose. In a preferred embodiment, the acetylated saccharide is selected from the group consisting of β-D-ribofuranose-1,2,3,5-tetraacetate; tri-O-acetyl-D-galactal; tri-O-acetyl-D-glucal; sucrose octaacetate; and acetylated cellulose.

In another embodiment, additional suitable substrates may also include 5-acetoxymethyl-2-furaldehyde; 3,4-diacetoxy-1-butene; 4-acetoxybenezoic acid; vanillin acetate; propylene glycol methyl ether acetate; methyl lactate; ethyl lactate; methyl glycolate; ethyl glycolate; methyl methoxyacetate; ethyl methoxyacetate; methyl 3-hydroxybutyrate; ethyl 3-hydroxybutyrate; and triethyl 2-acetyl citrate.

In another embodiment, suitable substrates are selected from the group consisting of: monoacetin; diacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-D-glucal; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,5-pentanediol; 1,6-pentanediol; 1,2-hexanediol; 2,5-hexanediol; 1,6-hexanediol; and mixtures thereof. In another embodiment, the substrate is a C1 to C6 polyol comprising one or more ester groups. In a preferred embodiment, one or more of the hydroxyl groups on the C1 to C6 polyol are substituted with one or more acetoxy groups (such as 1,3-propanediol diacetate; 1,2-propanediol diacetate; 1,4-butanediol diacetate; 1,5-pentanediol diacetate, etc.). In a further embodiment, the substrate is propylene glycol diacetate (PGDA), ethylene glycol diacetate (EGDA), or a mixture thereof.

In a further embodiment, suitable substrates are selected from the group consisting of monoacetin, diacetin, triacetin, monopropionin, dipropionin, tripropionin, monobutyrin, dibutyrin, and tributyrin. In yet another aspect, the substrate is selected from the group consisting of diacetin and triacetin. In a most preferred embodiment, the suitable substrate comprises triacetin.

The carboxylic acid ester is present at a concentration sufficient to produce the desired concentration of peroxycarboxylic acid upon enzyme-catalyzed perhydrolysis. The carboxylic acid ester need not be completely soluble in the reaction formulation, but has sufficient solubility to permit conversion of the ester by the perhydrolase catalyst to the corresponding peroxycarboxylic acid. The carboxylic acid ester is present in the reaction formulation at a concentration of 0.05 wt % to 40 wt % of the reaction formulation, preferably at a concentration of 0.1 wt % to 20 wt % of the reaction formulation, and more preferably at a concentration of 0.5 wt % to 10 wt % of the reaction formulation.

The peroxygen source is provided as granules deposited in or on the hydratable adhesive film and may include hydrogen peroxide adducts (e.g., urea-hydrogen peroxide adduct (carbamide peroxide)) perborate salts, percarbonate salts and peroxide salts. The concentration of peroxygen compound in the reaction formulation may range from 0.0033 wt % to about 50 wt %, preferably from 0.033 wt % to about 40 wt %, more preferably from 0.1 wt % to about 30 wt %.

Many perhydrolase catalysts (whole cells, permeabilized whole cells, and partially purified whole cell extracts) have been reported to have catalase activity (EC 1.11.1.6). Catalases catalyze the conversion of hydrogen peroxide into oxygen and water. In one aspect, the perhydrolysis catalyst lacks catalase activity. In another aspect, a catalase inhibitor may be added to the reaction formulation. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM.

In another embodiment, the enzyme catalyst lacks significant catalase activity or may be engineered to decrease or eliminate catalase activity. The catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis.

The concentration of peroxycarboxylic acid generated (e.g. peracetic acid) by the perhydrolysis of at least one carboxylic acid ester is at least about 0.1 ppm, preferably at least 0.5 ppm, 1 ppm, 5 ppm, 10 ppm, 20 ppm, 100 ppm, 200 ppm, 300 ppm, 500 ppm, 700 ppm, 1000 ppm, 2000 ppm, 5000 ppm or 10,000 ppm of peracid within 10 minutes, preferably within 5 minutes, of initiating the perhydrolysis reaction. Clearly one of skill in the art can adjust the reaction components to achieve the desired peracid concentration.

In one aspect, the reaction time required to produce the desired concentration of peracid is not greater than about two hours, preferably not greater than about 30 minutes, more preferably not greater than about 10 minutes, and most preferably in about 5 minutes or less. In other aspects, an oral cavity surface is contacted with the peroxycarboxylic acid formed in accordance with the processes described herein within 5 minutes of hydrating and combining the reaction components. In one embodiment, the tooth enamel is contacted with the peroxycarboxylic acid produced with the processes and compositions described herein within about 5 minutes to about 24 hours or within about 5 minutes to 2 hours of combining (via user hydration) said reaction components present in or on the whitening strip/film.

HPLC Assay Method for Determining the Concentration of Peroxycarboxylic Acid and Hydrogen Peroxide A variety of analytical methods can be used to analyze the reactants and products including, but not limited to, titration, high performance liquid chromatography (HPLC), gas chromatography (GC), mass spectroscopy (MS), capillary electrophoresis (CE), the analytical procedure described by U. Pinkernell et al., (*Anal. Chem.*, 69(17):3623-3627 (1997)), and the 2,2'-azino-bis β-ethylbenzothazoline)-6-sulfonate (ABTS) assay (U. Pinkernell et. al. *Analyst*, 122: 567-571 (1997) and Dinu et. al. *Adv. Funct. Mater.*, 20: 392-398 (2010)) as described in the present examples.

EXEMPLARY EMBODIMENTS

Embodiment 1

A tooth whitening strip (Strip 1) comprising a hydratable adhesive film with a first side and a second side, the first side having a granular bleaching ingredient attached thereto, wherein the strip comprises, in or on the film or in granules attached to the first side of the film, (i) a protein having perhydrolytic activity which contains the signature motif of a member of the carbohydrate esterase family 7;

(ii) an acyl donor, e.g., selected from carboxylic acid esters and acyl compounds, Embodiment 2

Strip 1 wherein the protein having perhydrolase activity comprises an amino acid sequence selected from:

(SEQ ID NO: 1)
a) MAFFDLPLEELKKYRPERYEEKDFDEFWEETLAESEKFPLDPVFERM

ESHLKTVEAYDVTFSGYRGQRIKGWLLVPKLEEEKLPCVVQYIGYNGGRG

FPHDWLFWPSMGYICFVMDTRGQGSGWLKGDTPDYPEGPVDPQYPGFMTR

GILDPRTYYYRRVFTDAVRAVEAAASFPQVDQERIVIAGGSQGGGIALAV

SALSKKAKALLCDVPFLCHFRRAVQLVDTHPYAEITNFLKTHRDKEEIVF

RTLSYFDGVNFAARAKIPALFSVGLMDNISPPSTVFAAYNYYAGPKEIRI

YPYNNHEGGGSFQAVEQVKFLKKLFEKG, b) an amino acid sequence having i) an RGQ motif at positions corresponding to positions 118-120 of SEQ ID NO: 1; ii) a GXSQG motif at positions corresponding to positions 186-190 of SEQ ID NO: 1; and iii) an HE motif at positions corresponding to positions 303-304 of SEQ ID NO: 1; and c) an amino acid sequence having at least 80% sequence identity to SEQ ID NO: 1.

Embodiment 3

Embodiment 1 or 2 wherein the protein having perhydrolytic activity comprises an amino acid sequence which has affinity to, e.g., binds to or complexes with oral surfaces or alternatively has affinity, e.g., binds to or complexes with, one or more components of the whitening strip.

Embodiment 4

Any of the foregoing strips comprising a protein having perhydrolase activity which binds to or complexes with oral surfaces (e.g., tooth pellicle or enamel) comprising an amino acid sequence selected from (SEQ ID NO: 2)
a) MAFFDLPLEELKKYRPERYEEKDFDEFWEETLAESEKFPLDPVFERM

ESHLKTVEAYDVTFSGYRGQRIKGWLLVPKLEEEKLPCVVQYIGYNGGRG

FPHDWLFWPSMGYICFVMDTRGQGSGWLKGDTPDYPEGPVDPQYPGFMTR

GILDPRTYYYRRVFTDAVRAVEAAASFPQVDQERIVIAGGSQGGGIALAV

SALSKKAKALLCDVPFLCHFRRAVQLVDTHPYAEITNFLKTHRDKEEIVF

RTLSYFDGVNFAARAKIPALFSVGLMDNISPPSTVFAAYNYYAGPKEIRI

YPYNNHEGGGSFQAVEQVKFLKKLFEKGGPGSGGAGSPGSAGGPGSTKPP

RTPTANTSRPHHNFGSGGGGSPHHHHHH,
and b) an amino acid sequence having at least 80% sequence identity to SEQ ID NO: 2.

Embodiment 5

Any of the foregoing strips wherein the protein having perhydrolytic activity is provided in granular form on the first surface of the film.

Embodiment 6

Any of the foregoing strips wherein the second side of the hydratable adhesive film is attached to a layer which inhibits dissolution of the hydratable adhesive film.

Embodiment 7

Any of the foregoing strips wherein the granular bleaching ingredient is coated with a quickly dissolving material, such as cornstarch, sodium sulfate gum arabic, and combinations thereof.

Embodiment 8

Any of the foregoing strips wherein the granular bleaching ingredient is selected from granules comprising organic and/or inorganic oxidizers, e.g., selected from hydrogen peroxide, urea peroxide, percarbonates, perborates, peroxymonophosphates, peroxydisulfates, peroxyacids, and peracetic acid.

Embodiment 9

Any of the foregoing strips wherein the granular bleaching ingredient is selected from solid peroxides and solid peroxide donors, e.g., selected from peroxide salts or complexes (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate); hypochlorites; urea peroxide; hydrogen peroxide polymer complexes such as hydrogen peroxide-polyvinyl pyrrolidone polymer complexes; metal peroxides e.g. zinc peroxide and calcium peroxide; peracids, and combinations thereof.

Embodiment 10

Any of the foregoing strips wherein the granular bleaching ingredient comprises urea peroxide, a hydrogen peroxide-polyvinyl pyrrolidone polymer complex, sodium percarbonate, or a combination of two or more thereof.

Embodiment 11

Any of the foregoing strips where the particle size ($D_{50}$) of the granules on the first surface of the film, e.g., the granular bleaching ingredient, or perhydrolase or acyl donor in granular form, is 0.1-300 microns, e.g. 10-275 microns, e.g., 100-250 microns.

Embodiment 12

Any of the foregoing strips wherein the granular bleaching ingredient comprises greater than 0.01%, e.g. 0.01-0.1%, e.g. 0.02-0.08%, of the total weight of the hydratable adhesive film and a granular bleaching ingredient attached thereto.

Embodiment 13

Any of the foregoing strips wherein the amount of granular bleaching agent on the first side of the hydratable adhesive film is 0.001-10 mg/cm$^2$, e.g., 0.001-1 mg/cm$^2$, for example 0.005-0.015 mg/cm$^2$.

Embodiment 14

Any of the foregoing strips wherein the acyl donor is selected from (i) one or more $C_{2-18}$ carboxylic acid esters, e.g $C_{2-6}$ carboxylic acid esters (e.g., acetyl esters), including lower linear or branched alkyl carboxylic acid esters, optionally substituted with hydroxy and/or $C_{1-4}$ alkoxy; (ii) one or more acylated glycerides (e.g. mono-, di-, and tri-glycerides), (iii) acylated saccharides, and (iv) mixtures thereof.

Embodiment 15

Any of the foregoing strips the acyl donor is selected from 1,2,3-triacetoxypropane (sometimes referred to herein as triacetin or glycerin triacetate) and acylated saccharides, e.g. acylated saccharides.

Embodiment 16

Any of the foregoing strips comprising an acyl donor which comprises an ester compound having solubility in water of at least 5 ppm at 25° C.

Embodiment 17

Any of the foregoing strips which comprises a peracid or which generates a peracid upon use.

Embodiment 18

Any of the foregoing strips wherein the ingredients are present in amounts sufficient to provide, upon mixing, a bleaching agent in an amount and concentration effective to whiten teeth.

Embodiment 19

Any of the foregoing strips wherein the hydratable adhesive film comprises one or more water-soluble polymers selected from hydrophilic cellulose ethers (e.g. carboxymethyl cellulose, hydroxypropyl cellulose, hydroxypropyl methylcellulose), polyvinyl acetates, carbomers (e.g., CARBOPOL® 971P), polysaccharide gums (e.g. xanthan gum), modified food starches, gelatin (e.g. animal or fish-based gelatin), cross-linked carboxyvinyl copolymers, cross-linked polyvinylpyrrolidones, polyethylene oxide (e.g, POLYOX™), polyacrylic acids and polyacrylates, polyvinyl alcohols, alginate, casein, pullulan, and combinations thereof.

Embodiment 20

Any of the foregoing strips wherein the hydratable adhesive film comprises one or more water-soluble polymers selected from hydrophilic cellulose ethers (e.g. hydroxypropylmethyl cellulose or hydroxypropyl cellulose), polyethylene oxide, polyvinyl acetates, and carbomers (e.g., CARBOPOL® 971P); and combinations thereof.

Embodiment 21

Any of the foregoing strips wherein the hydratable adhesive film comprises hydroxypropylmethyl cellulose, polyvinyl acetates, and a carbomer, for example, in a dry weight ratio of 10-20 HPMC:2-10 PVAc:1 carbomer.

Embodiment 22

Any of the foregoing strips wherein the hydratable adhesive film further comprises a plasticizer, e.g. propylene glycol, polyethylene glycol or triacetin.

Embodiment 23

Any of the foregoing strips wherein the first side of the hydratable adhesive film is covered by a protective cover prior to use.

Embodiment 24

Any of the foregoing strips wherein the hydratable adhesive film has a viscosity of at least 100,000 cps upon activation, e.g., viscosity of 100,000 to 200,000 cps.

Embodiment 25

Any of the foregoing strips wherein the hydratable adhesive film is substantially dry prior to application.

Embodiment 26

Any of the foregoing strips wherein the thickness of the hydratable adhesive film is 0.1-5 mm, e.g., 0.5-5 mm.

Embodiment 27

Any of the foregoing strips wherein the approximate overall dimensions are 2-10 cm long×0.5-2 cm wide×0.1-10 mm thick, e.g., 1-10 mm thick, for example a strip wherein the surface area of one side is 5-20 $cm^2$, e.g., about 5-15 $cm^2$, e.g., about 10 $cm^2$.

Embodiment 28

Any of the foregoing strips comprising coated granules of a hydrogen peroxide-polyvinyl pyrrolidone polymer complex, urea peroxide and/or sodium percarbonate and granules of perhydrolase on the first surface of the film, with triacetin dispersed in the film.

Embodiment 29

Any of the foregoing strips, further comprising granules of an antisensitivity agent, e.g. potassium nitrate or arginine.

Embodiment 30

A method (Method 2) of whitening teeth comprising applying the first side of a strip as hereinbefore described, e.g. Strip 1 et seq. directly to the teeth, and leaving it on for a sufficient time, e.g., at least 5 minutes, for example 10-60 minutes, e.g., 10-30 minutes, to whiten the teeth.

Embodiment 31

A method (Method 3) of making a strip for tooth whitening, e.g., a strip as hereinbefore described, according to Strip 1 et seq., comprising providing a semi-dry hydratable adhesive film, e.g., as hereinbefore described, e.g., which film has been cast from water and not fully dried, or which film has been moistened, adding to one surface of the film granules of a granular bleaching ingredient, e.g., as hereinbefore described, and drying the film with the granules added to one surface.

For example, the strips may be made by first making the hydratable adhesive film, using conventional means and then adding the granulated whitening ingredient to one surface. The hydratable adhesive film strips can be cast from water in a variety of ways known in the art, such as by extrusion, or by casting from a water suspension (for example at a solids level of 10-30%) onto a heated belt, from which the water is evaporated. Alternatively, the film is dried, but then remoistened. The granules can be added to the surface of this film while the film is semi-dry, i.e. just moist enough to be tacky, so that the granules stick to the surface of the film. Once the film is fully dry and cooled to room temperature, the granules continue to adhere to the surface of the film. Prior to use, therefore, the hydratable adhesive film and the strip as a whole are substantially dry. Because the peroxide is on the surface of the film only, a relatively small quantity of granules are required to provide an effective concentration at the surface.

Preferred Embodiments

When exposed to saliva or other sources of water (such as tap water), the granules dissolve and release the reaction components to enzymatically produce the desired peracid. Hydration of the hydratable adhesive layer increases the tackiness of the film, enabling the whitening film/strip to bind to the target surface (i.e., tooth enamel).

The hydratable adhesive film comprises one or more water soluble, orally acceptable polymers selected from hydrophilic cellulose ethers (e.g., carboxymethyl cellulose, hydroxypropyl cellulose, hydroxypropyl methylcellulose), polyvinyl acetates, carbomers (e.g., CARBOPOL® 971P), polysaccharide gums (e.g., xanthan gum), modified food starches, gelatin (e.g., animal or fish-based gelatin), cross-linked carboxyvinyl copolymers, cross-linked polyvinylpyrrolidones, polyethylene oxide (e.g., POLYOX™), polyacrylic acids and polyacrylates, polyvinyl alcohols, alginate, casein, pullulan, and combinations thereof. Adhesive gel formulations for use with tooth whitening agents are known in the art, for example, as described in U.S. Pat. Nos. 7,862,801; 5,746,598; 6,730,316; and 7,128,899; each incorporated by reference in its entirety. The adhesive film allows the peracid bleaching agent to stay in contact with the teeth for extended periods of time and protects soft tissues, and thus should provide a high viscosity, for example, a viscosity upon application of at least 100,000 centipoise (cps) (about 100 Pascal-second (Pa·s)), preferable 100,000 to 200,000 cps (100 to 200 Pa·s).

Where a second film layer is used to protect the hydratable adhesive film from rapid degradation or dissolution, the carrier or backing material may be made from textiles, cloth, wood composite, resin, elastomer, paper, insoluble or less soluble cellulose derivatives such as ethyl cellulose and cellulose acetate, polyvinyl chloride, wax, PARAFILM™, polyethylene, polyvinyl alcohol, TEFLON™, polyvinyl chloride, polyvinyl acetate and their derivatives.

The granular bleaching ingredient may be a solid peroxide or solid peroxide donor selected from peroxide salts or complexes (such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), hypochlorites; urea peroxide; hydrogen peroxide polymer complexes such as hydrogen peroxide-polyvinyl pyrrolidone polymer complexes, and metal peroxides, for example, zinc peroxide and calcium peroxide; a solid peracid; and combinations thereof. In particular embodiments, the granular bleaching ingredient is urea peroxide or a hydrogen peroxide polyvinylpyrrolidone polymer complex. The granular bleaching ingredient may be optionally coated to provide improved storage stability (for example, coated with sodium sulfate, corn starch or gum arabic).

Listing of the Preferred Embodiments

Preferred Embodiment 1

A tooth whitening strip comprising a hydratable adhesive film with a first side and a second side, the first side having a granular bleaching ingredient attached thereto, wherein the tooth whitening strip further comprises, in or on the film or in the form of granules attached to the first side of the film;
  a) an enzyme having perhydrolytic activity, said enzyme having a carbohydrate esterase family 7 (CE-7) signature motif that aligns with a reference sequence SEQ ID NO: 1, said signature motif comprising:
    i) an RGQ motif at positions corresponding to positions 118-120 of SEQ ID NO: 1;
    ii) a GXSQG motif at positions corresponding to positions 186-190 of SEQ ID NO:1; and
    iii) an HE motif at positions corresponding to positions 303-304 of SEQ ID NO:1; and
  (b) at least one acyl donor substrate, said substrate selected from the group consisting of:
    i) esters having the structure $[X]_m R_5$ 

wherein X=an ester group of the formula $R_6C(O)O$
    $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;
    $R_5$=a C1 to C6 linear, branched, or cyclic hydrocarbyl moiety or a five-membered cyclic heteroaromatic moiety or six-membered cyclic aromatic or heteroaromatic moiety optionally substituted with hydroxyl groups; wherein each carbon atom in $R_5$ individually comprises no more than one hydroxyl group or no more than one ester group or carboxylic acid group; wherein $R_5$ optionally comprises one or more ether linkages;
    M is an integer ranging from 1 to the number of carbon atoms in $R_5$; and
    wherein said esters have solubility in water of at least 5 ppm at 25° C.;
    ii) glycerides having the structure

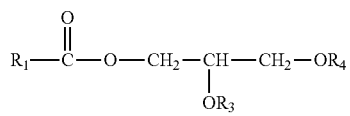

wherein $R_1$=C1 to C7 straight chain or branched chain alkyl optionally substituted with an hydroxyl or a C1 to C4 alkoxy group and $R_3$ and $R_4$ are individually H or $R_1C(O)$;
    iii) one or more esters of the formula

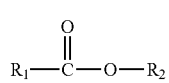

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10; and
    iv) acetylated saccharides selected from the group consisting of acetylated monosaccharides, acetylated disaccharides, and acetylated polysaccharide; wherein upon hydration of the hydratable adhesive film hydrogen peroxide is released from the granular bleaching ingredient and said enzyme catalyzes the formation of an effective amount of a peracid.

Preferred Embodiment 2

The tooth whitening strip according to preferred embodiment 1 wherein the enzyme having perhydrolytic activity comprises an amino acid sequence selected from:
  a) SEQ ID NO: 1; and
  b) an amino acid sequence having at least 80% amino acid sequence identity to SEQ ID NO: 1.

Preferred Embodiment 3

The tooth whitening strip according to Preferred Embodiment 1 wherein the enzyme having perhydrolytic activity further comprises a binding domain fused to the N- or C-terminus of the enzyme, said binding domain having affinity for an oral tissue or for the tooth whitening strip.

Preferred Embodiment 4

The tooth whitening strip according to Preferred Embodiment 3 wherein the binding domain having affinity for an oral tissue comprises an amino acid sequence selected from the group consisting of SEQ ID NOs: 178-197.

Preferred Embodiment 5

The tooth whitening strip according to any of the above preferred embodiments wherein the enzyme having perhydrolytic activity has affinity for an oral tissue and comprises an amino acid sequence selected from
  a) SEQ ID NO: 2, and
  b) an amino acid sequence having at least 80% amino acid sequence identity to SEQ ID NO: 2.

Preferred Embodiment 6

The tooth whitening strip according to any of the above preferred embodiments further comprising a backing layer attached to said second side of the hydratable adhesive film, said backing layer capable of inhibiting dissolution of the hydratable adhesive film.

Preferred Embodiment 7

The tooth whitening strip according to any of the above preferred embodiments wherein the granular bleaching ingredient is coated with a water soluble coating capable of dissolving upon hydration.

Preferred Embodiment 8

The tooth whitening strip according to any of the above preferred embodiments wherein the granular bleaching ingredient is selected from solid peroxides and solid peroxide donors.

Preferred Embodiment 9

The tooth whitening strip according to any of the above preferred embodiments wherein the granular bleaching ingredient is selected from peroxide salts, peroxide complexes, peroxyphosphate, peroxycarbonate, perborate, peroxysilicate, persulphate salts, calcium peroxyphosphate, sodium perborate, sodium carbonate peroxide, sodium peroxyphosphate, potassium persulfate, hypochlorites, urea peroxide, hydrogen peroxide polymer complexes, hydrogen peroxide-polyvinyl pyrrolidone polymer complexes, metal peroxides, zinc peroxide, calcium peroxide, and combinations thereof.

Preferred Embodiment 10

The tooth whitening strip according to any of the above preferred embodiments wherein the granular bleaching ingredient comprises urea peroxide. In some embodiments, the granular bleaching ingredient comprises a hydrogen peroxide-polyvinyl pyrrolidone polymer complex. In some embodiments, the hydrogen peroxide-polyvinyl pyrrolidone polymer complex is a hydrogen peroxide-crosslinked polyvinyl pyrrolidone polymer complex.

Preferred Embodiment 11

The tooth whitening strip according to any of the above preferred embodiments wherein the particle size median diameter (D50) of the granular bleaching ingredient ranged from 10 microns to 300 microns, e.g., 10 microns to 200 microns.

Preferred Embodiment 12

The tooth whitening strip according to any of the above preferred embodiments wherein the tooth whitening strip comprises from about 0.01 wt % to about 0.1 wt % of a peracid. In some embodiments, the granular bleaching ingredient comprises from about 0.1 wt % to about 30 wt % of a peroxygen source.

Preferred Embodiment 13

The tooth whitening strip according to any of the above preferred embodiments wherein the amount of granular bleaching agent on the first side of the hydratable adhesive film ranges from 0.001 mg/cm$^2$ to 10 mg/cm$^2$, e.g., 0.001 mg/cm$^2$ to 1 mg/cm$^2$.

Preferred Embodiment 14

The tooth whitening strip according to any of the above preferred embodiments wherein the acyl donor substrate is 1,2,3-triacetoxypropane.

Preferred Embodiment 15

The tooth whitening strip according to any of the above preferred embodiments wherein the hydratable adhesive film comprises one or more water-soluble polymers selected from a hydrophilic cellulose ether, carboxymethyl cellulose, hydroxypropyl cellulose, hydroxypropyl methylcellulose, a polyvinyl acetate, a carbomer, a polysaccharide gum, xanthan gum, a modified food starch, gelatin, animal or fish-based gelatin, a cross-linked carboxyvinyl copolymer, a cross-linked polyvinylpyrrolidone, polyethylene oxide, a polyacrylic acid, a polyacrylate, a polyvinyl alcohol, alginate, casein, pullulan, and a combination of two or more thereof.

Preferred Embodiment 16

The tooth whitening strip according to any of the above preferred embodiments wherein the hydratable adhesive film comprises one or more water-soluble polymers selected from a hydrophilic cellulose ether, a polyvinyl acetate, a carbomer, and a combination of two or more thereof.

Preferred Embodiment 17

The tooth whitening strip according to any of the above preferred embodiments wherein the hydratable adhesive film comprises hydroxypropylmethyl cellulose (HPMC), polyvinyl acetate (PVAc), and a carbomer in a dry weight ratio for HMPC:PVAc:carbomer of 10-20:2-10:1.

Preferred Embodiment 18

The tooth whitening strip according to any of the above preferred embodiments wherein the hydratable adhesive film further comprises a plasticizer.

Preferred Embodiment 19

The tooth whitening strip according to any of the above preferred embodiments further comprising propylene glycol.

Preferred Embodiment 20

A method of whitening teeth comprising
a) providing a packaging system comprising the tooth whitening strip according to any of the above preferred embodiments;
b) removing the tooth whitening strip from the packaging system; and
c) contacting the tooth whitening strip directly to the teeth for a period of time sufficient to whiten the teeth; wherein the tooth whitening strip is hydrated by moisture present in the oral cavity or on the tooth surface or is hydrated after step (b) but prior to step (c).

Preferred Embodiment 21

The method of Preferred Embodiment 20 wherein the whitening strip further comprises a backing layer attached to said second side of the hydratable adhesive film, said backing layer capable of inhibiting dissolution of the hydratable adhesive film.

Preferred Embodiment 22

The method according to any of the above preferred embodiments wherein the particle size median diameter (D50) of the granular bleaching ingredient ranged from 10 microns to 200 microns.

Preferred Embodiment 23

The method according to any of the above preferred embodiments wherein the granular bleaching ingredient comprises greater than 0.01 wt % of the total weight of the hydratable adhesive film and a granular bleaching ingredient attached thereto. In some embodiments, the granular bleaching ingredient comprises greater than 0.05 wt % of the total weight of the hydratable adhesive film and a granular bleaching ingredient attached thereto. In some embodiments, the granular bleaching ingredient comprises from about 0.01 wt % to about 0.1 wt % of the total weight of the hydratable adhesive film and a granular bleaching ingredient attached thereto.

Preferred Embodiment 24

The method according to any of the above preferred embodiments wherein the amount of granular bleaching agent on the first side of the hydratable adhesive film ranges from 0.001 mg/cm$^2$ to 1 mg/cm$^2$.

Preferred Embodiment 25

The method according to any of the above preferred embodiments wherein the acyl donor substrate is 1,2,3-triacetoxypropane.

Preferred Embodiment 26

The method according to any of the above preferred embodiments wherein the hydratable adhesive film comprises one or more water-soluble polymers selected from a hydrophilic cellulose ether, carboxymethyl cellulose, hydroxypropyl cellulose, hydroxypropyl methylcellulose, a polyvinyl acetate, a carbomer, a polysaccharide gum, xanthan gum, a modified food starch, gelatin, animal or fish-based gelatin, a cross-linked carboxyvinyl copolymer, a cross-linked polyvinylpyrrolidone, polyethylene oxide, a polyacrylic acid, a polyacrylate, a polyvinyl alcohol, alginate, casein, pullulan, and a combination of two or more thereof.

Preferred Embodiment 27

The method according to any of the above preferred embodiments wherein the hydratable adhesive film comprises one or more water-soluble polymers selected from a hydrophilic cellulose ether, a polyvinyl acetate, a carbomer, and a combination of two or more thereof.

Preferred Embodiment 28

The method according to any of the above preferred embodiments wherein the hydratable adhesive film comprises hydroxypropylmethyl cellulose (HPMC), polyvinyl acetate (PVAc), and a carbomer in a dry weight ratio for HMPC:PVAc:carbomer of 10-20:2-10:1.

Preferred Embodiment 29

The method according to any of the above preferred embodiments wherein the hydratable adhesive film further comprises a plasticizer.

Preferred Embodiment 30

The method according to any of the above preferred embodiments wherein the hydratable adhesive film further comprises propylene glycol.

Preferred Embodiment 31

The method according to any of the above preferred embodiments wherein the granular bleaching ingredient is coated with a water soluble coating capable of dissolving upon hydration.

Preferred Embodiment 32

A method of making a tooth whitening strip comprising:
a) providing a semi-dry hydratable adhesive film,
b) applying to one surface of the film granules of a granular bleaching ingredient whereby the granules adhere to the surface, and
c) drying the film.

In some embodiments, the particle size median diameter (D50) of the granular bleaching ingredient is from 10 microns to 300 microns. In some embodiments, the particle size median diameter (D50) of the granular bleaching ingredient is from 25 microns to 200 microns. In some embodiments, the particle size median diameter (D50) of the granular bleaching ingredient is from 35 microns to 150 microns. In some embodiments, the particle size median diameter (D50) of the granular bleaching ingredient is from 50 microns to 125 microns. In some embodiments, the particle size median diameter (D50) of the granular bleaching ingredient is from 60 microns to 100 microns. In some embodiments, the particle size median diameter (D50) of the granular bleaching ingredient is about 64 microns. In some embodiments, the particle size median diameter (D50) of the granular bleaching ingredient is about 94 microns.

In some embodiments, the particle size median diameter (D50) of the enzyme having perhydrolytic activity is from 100 microns to 300 microns. In some embodiments, the particle size median diameter (D50) of the enzyme having perhydrolytic activity is from 150 microns to 275 microns. In some embodiments, the particle size median diameter (D50) of the enzyme having perhydrolytic activity is from 175 microns to 250 microns.

All ingredients for use in the strips described herein should be orally acceptable. By "orally acceptable" as the term is used herein is meant an ingredient which is present in a strip as described in an amount and form which does not render the strip unsafe for use in the oral cavity.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

The following examples are provided to demonstrate preferred aspects of the invention. It should be appreciated by those of skill in the art that the techniques disclosed in the examples follow techniques to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the presently disclosed methods and examples.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.), Thermo Scientific (Pierce Protein Research Products) (Rockford, Ill.) or Sigma/Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "µL" means microliter(s), "mL" means milliliter(s), "L" means liter(s), "mM" means millimolar, "M" means molar, "mmol" means millimole(s), "ppm" means part(s) per million, "wt" means weight, "wt %" means weight percent, "g" means gram(s), "mg" means milligram(s), "µg" means microgram(s), and "ng" means nanogram(s).

Example 1

A strip is prepared as described above, forming the hydratable adhesive film and then while the film is still tacky, adding the granulated whitening agent and granulated enzyme to the surface of one side, using the ingredients in Table 1. The strip will erode slowly in the mouth upon application, and so does not need to be removed.

TABLE 1

| Ingredients in Strip | Dry Strip Concentration (wt %) |
|---|---|
| Hydroxypropylmethylcellulose (HPMC) | 59 |
| Polyvinylacetate (PVAc) | 30 |
| Carbopol, 971 | 5 |
| Triacetin | 5 |
| Titanium dioxide | 1 |
| Total | 100 |

| Ingredients in Bleach Granule | Concentration (wt %) |
|---|---|
| Urea peroxide | 100 |

| Ingredients in Enzyme Granule | Concentration (wt %) |
|---|---|
| Cornstarch | 99 |
| Perhydrolase enzyme | 1 |

The strip in example 1 is cast from water by extrusion, or by casting from a water suspension (for example at a solids level of 10-30%) onto a heated belt, from which the water is evaporated. The granules are added to the surface of this film when the film is semi-dry or dry, but still tacky. Once cooled to room temperature, the granules adhere to the surface of the film. For a strip with an area of 10 cm$^2$ and a weight of 10 mg/cm$^2$, this formula delivers 5 mg triacetin. Assuming that 1.4 mg of bleach granules are distributed on the strip, along with 0.3 mg of enzyme granules, this dose is sufficient to produce enough peracetic acid directly at the tooth surface to significantly outperform a peroxide-only whitening strip. (Peroxide only strips typically have a total dose of approximately 3-10 mg peroxide.)

When exposed to saliva or other sources of water (such as tap water), the granules immediate dissolve and become active. The adhesive layer also is activated and sticks to the teeth effectively. Example 1 is designed to slowly erode in the mouth over time, so the user does not need to remove it.

Example 2

A strip is prepared as described above, forming the hydratable adhesive film and then while the strip is still tacky, adding the granulated agents to one side and the protective backing layer to the other side, using the ingredients in Table 2. Because the backing layer will not dissolve, the user should remove it after a sufficient period has passed to permit whitening to take place, typically about 10-30 minutes. The two layers can also be produced simultaneously by extrusion or solvent-based casting, then the granulated whitening agent can be added to the surface of the hydratable adhesive film.

TABLE 2

| Ingredients in Layer #1 | Dry Strip Concentration (wt %) |
|---|---|
| Ethyl cellulose | 94 |
| Propylene glycol | 5 |
| Titanium dioxide | 1 |
| Total | 100 |

| Ingredients in Layer #2 | Dry Strip Concentration (wt %) |
|---|---|
| Hydroxypropylmethylcellulose (HPMC) | 69 |
| Polyvinylacetate (PVAc) | 15 |
| Carbopol, 971 | 5 |
| Triacetin | 5 |
| Titanium dioxide | 1 |
| Flavor | 5 |
| Total | 100 |

| Ingredients in Bleach Granule | Concentration (wt %) |
|---|---|
| Gum arabic | 10 |
| Urea peroxide | 90 |

| Ingredients in Enzyme Granule | Concentration (wt %) |
|---|---|
| Cornstarch | 99 |
| Perhydrolase enzyme | 1 |

Example 3

Various particle sizes of hydrogen peroxide-polyvinylpyrrolidone complex and an enzyme having perhydrolytic activity ("enzyme") were evaluated for their ability to generate peracetic acid uniformly across the surface of a hydratable adhesive strip containing triacetin.

To evaluate the generation of peracetic acid from this product, ⅜" discs were cut from the film. Each disc was hydrated with 20 µL of 50 mM sodium phosphate buffer, pH 7.2 and incubated at 37° C. for 15 min. 380 µL of 0.1 M phosphoric acid was added to the film to quench the enzyme reaction and dilute the sample for detection. The solution was analyzed for peracetic acid with HPLC analyses for peracetic acid using the method described previously in U.S. Pat. No. 7,829,315 to DiCosimo et al. For each evaluation, a minimum of three samples were cut from the strip product across a 24 inch length of film.

Strip samples with the enzyme and hydrogen peroxide-polyvinylpyrrolidone coating were made by first incorporating the enzyme in a pullulan polymer film. The dried film containing the enzyme was milled and sieved to a particle size of 60 to 80 mesh (177 μm to 250 μm). The particulate form of enzyme was then blended with hydrogen peroxide-polyvinylpyrrolidone (PEROXYDONE™ XL-10, Ashland Inc., Wilmington, Del.). This blend was deposited onto a two-layer film structure with a hydratable adhesive layer containing primarily polyethylene oxide and triacetin and a backing layer of polyvinyl alcohol to provide a non-dissolvable support layer. The results of evaluation of peracetic acid generation for two consecutive runs are listed in Table 3. Samples were evaluated at the beginning and end of the production run and demonstrate poor consistency for peracetic acid.

TABLE 3

Peracetic acid production from hydratable adhesive strips produced with a coating of perhydrolase enzyme in pullulan and PEROXYDONE ™ XL-10.

| | Start of Run | | End of Run | |
|---|---|---|---|---|
| Sample | Avg PAA (ppm) | Std Dev (3 replicates) | Avg PAA (ppm) | Std Dev (3 replicates) |
| 1 | 304 | 27 | 110 | 5 |
| 2 | 132 | 16 | 55 | 3 |

The PEROXYDONE™ XL-10 was further processed to form larger particles with ethanol high shear granulation. After granulation the sample was sieved to a particle size of 60 to 200 mesh (75 μm to 250 μm). The particle size distribution of PEROXYDONE™ XL-10, as used to produce samples described in Table 3, and the PEROXYDONE™ XL-10 following high shear granulation and sieving are described in Table 4. The samples were measured on a Beckman Coulter LS13320 equipped with a Tornado dry feeder. The powders were analyzed directly without being dispersed in a liquid.

TABLE 4

Particle size distribution for PEROXYDONE ™ XL-10 used in deposition before and after granulation.

| PEROXYDONE ™ XL-10 Sample | Particle Size Distribution Statistics (μm) | | | |
|---|---|---|---|---|
| | Mean | Median | D10 | D90 |
| As received | 75.9 | 64.0 | 28.5 | 143.5 |
| After granulation | 100.5 | 93.8 | 49.9 | 165.1 |

Another strip production run was completed by first preparing an enzyme sample loaded into the pullulan matrix at twice the concentration of samples from Table 3. The pullulan film was milled and sieved to 60 to 80 mesh (177 μm to 250 μm) and then combined with the granulated PEROXYDONE™ XL-10. The blend was then coated onto a similar two-layer film structure as described above. The evaluation of this sample for peracetic acid generation is provided in Table 4, and demonstrated higher and more consistent production of peracetic acid throughout the production run.

TABLE 5

Peracetic acid production from hydratable adhesive strips produced with a coating of perhydrolase enzyme in pullulan and high shear granulated PEROXYDONE ™ XL-10.

| | Start of Run | | End of Run | |
|---|---|---|---|---|
| Sample | Avg PAA (ppm) | Std Dev (3 replicates) | Avg PAA (ppm) | Std Dev (3 replicates) |
| 3 | 828 | 51 | 1039 | 162 |

The invention claimed is:

1. A tooth whitening strip comprising a hydratable adhesive film with a first side and a second side, the first side having a granular bleaching ingredient attached thereto, wherein the strip comprises, in or on the film or in the form of granules attached to the first side of the film,
   (i) a granulated protein having perhydrolase activity which contains the catalytic domain of a member of the carbohydrate esterase family 7; and
   (ii) a carboxy donor,
wherein upon use, the peroxide released by the granular bleaching ingredient reacts with the carboxy donor in the presence of the perhydrolase to form a peracid;
wherein the granulated protein having perhydrolase activity comprises an amino acid sequence selected from SEQ ID NO: 1;
wherein the tooth whitening strip comprises a backing layer;
wherein the carboxy donor is 1,2,3-triacetoxypropane;
wherein the hydratable adhesive film comprises hydroxypropylmethylcellulose (HPMC); and
wherein the granules immediately dissolve and become active when exposed to saliva or other sources of water.

2. The tooth whitening strip according to claim 1, wherein the protein having perhydrolase activity has affinity for oral tissue and further comprises an amino acid sequence selected from a)

SEQ ID NO: 2
MAFFDLPLEELKKYRPERYEEKDFDEFWEETLAESEKFPLDPVFERMESH

LKTVEAYDVTFSGYRGQRIKGWLLVPKLEEEKLPCVVQYIGYNGGRGFPH

DWLFWPSMGYICFVMDTRGQGSGWLKGDTPDYPEGPVDPQYPGFMTRGIL

DPRTYYYRRVFTDAVRAVEAAASFPQVDQERIVIAGGSQGGGIALAVSAL

SKKAKALLCDVPFLCHFRRAVQLVDTHPYAEITNFLKTHRDKEEIVFRTL

SYFDGVNFAARAKIPALFSVGLMDNISPPSTVFAAYNYYAGPKEIRIYPY

NNHEGGGSFQAVEQVKFLKKLFEKGGPGSGGAGSPGSAGGPGSTKPPRTP

TANTSRPHHNFGSGGGGSPHHHHHH,
and and b) an amino acid sequence having at least 80%, sequence identity to SEQ ID NO: 2.

3. The tooth whitening strip according to claim 1 wherein the granular bleaching ingredient is coated with a quickly dissolving material.

4. The tooth whitening strip according to claim 1 wherein the granular bleaching ingredient is selected from solid peroxides and solid peroxide donors.

5. The tooth whitening strip according to claim 1 wherein the granular bleaching ingredient is selected from peroxide salts or complexes, peroxyphosphate, peroxycarbonate, perborate, peroxysilicate, persulphate salts, calcium peroxyphosphate, sodium perborate, sodium carbonate peroxide, sodium peroxyphosphate, potassium persulfate, hypochlorites, urea peroxide, hydrogen peroxide polymer complexes, hydrogen peroxide-polyvinyl pyrrolidone polymer complexes, metal peroxides, zinc peroxide, calcium peroxide, peracids, and combinations thereof.

6. The tooth whitening strip according to claim 1 wherein the granular bleaching ingredient comprises urea peroxide.

7. The tooth whitening strip according to claim 1 wherein the particle size (D50) of the granular bleaching ingredient is 10-200 microns.

8. The tooth whitening strip according to claim 7 wherein the granular bleaching ingredient comprises 0.1% or less of the total weight of the hydratable adhesive film and a granular bleaching ingredient attached thereto.

9. The tooth whitening strip according to claim 8 wherein the amount of granular bleaching agent on the first side of the hydratable adhesive film is 0.001-1 mg/cm$^2$.

10. The tooth whitening strip according to claim 1 which comprises a peracid or which generates a peracid upon use.

11. The tooth whitening strip according to claim 1 wherein the ingredients are present in amounts sufficient to provide, upon mixing, a bleaching agent in an amount and concentration effective to whiten teeth.

12. The tooth whitening strip according to claim 1 wherein the hydratable adhesive film further comprises one or more water-soluble polymers selected from a hydrophilic cellulose ether, carboxymethyl cellulose, hydroxypropyl cellulose, a polyvinyl acetate, a carbomer, a polysaccharide gum, xanthan gum, a modified food starch, gelatin, animal or fish-based gelatin, a cross-linked carboxyvinyl copolymer, a cross-linked polyvinylpyrrolidone, polyethylene oxide, a polyacrylic acid, a polyacrylate, a polyvinyl alcohol, alginate, casein, pullulan, and a combination of two or more thereof.

13. The tooth whitening strip according to claim 1, wherein the hydratable adhesive film comprises one or more water-soluble polymers selected from a hydrophilic cellulose ether, a polyvinyl alcohol, a carbomer, and a combination of two or more thereof.

14. The tooth whitening strip according to claim 1, wherein the hydratable adhesive film further comprises a plasticizer.

15. The tooth whitening strip according to claim 1, wherein the hydratable adhesive film further comprises propylene glycol.

16. The tooth whitening strip according to claim 1, wherein the granular bleaching ingredient is coated with a water soluble coating capable of dissolving upon hydration.

17. The tooth whitening strip according to claim 1, wherein an effective amount of a peracid is generated at a substantially uniform concentration across the surface of the tooth whitening strip.

18. A method of whitening teeth comprising
a) providing a packaging system comprising the tooth whitening strip according to claim 1;
b) removing the tooth whitening strip from the packaging system; and
c) contacting the tooth whitening strip directly to the teeth for a period of time sufficient to whiten the teeth; wherein the tooth whitening strip is hydrated by moisture present in the oral cavity or on the tooth surface or is hydrated after step (b) but prior to step (c).

* * * * *